(12) United States Patent
Marzabadi et al.

(10) Patent No.: US 8,222,218 B2
(45) Date of Patent: Jul. 17, 2012

(54) CYCLOPROPANATED CARBOHYDRATES

(75) Inventors: Cecilia H. Marzabadi, Ridgewood, NJ (US); Ian Jamie Talisman, Bethesda, MD (US)

(73) Assignee: Seton Hall University, South Orange, NJ (US)

( * ) Notice: Subject to any disclaimer, the term of this patent is extended or adjusted under 35 U.S.C. 154(b) by 441 days.

(21) Appl. No.: 12/383,861

(22) Filed: Mar. 27, 2009

(65) Prior Publication Data

US 2009/0281046 A1 Nov. 12, 2009

Related U.S. Application Data

(60) Provisional application No. 61/072,087, filed on Mar. 27, 2008, provisional application No. 61/125,732, filed on Apr. 28, 2008.

(51) Int. Cl.
- *A01N 43/04* (2006.01)
- *A61K 31/70* (2006.01)
- *C07H 17/00* (2006.01)

(52) U.S. Cl. .......................... 514/23; 536/1.11
(58) Field of Classification Search .................. None
See application file for complete search history.

(56) References Cited

U.S. PATENT DOCUMENTS

| | | |
|---|---|---|
| 2003/0181402 A1 | 9/2003 | Wei et al. |
| 2005/0169982 A1 | 8/2005 | Almarssoo et al. |
| 2006/0276412 A1 | 12/2006 | Tollefson |

OTHER PUBLICATIONS

Henry et al. Tetrahedron Letters, vol. 36, No. 49, 8901-8904, 1995.*
Yu et al., Organic Letters, 2003, vol. 5(26), 5099-5101.*
Yu et al., Organic Letters, 2003, vol. 5(24), 4639-4640.*
International Search Report Issued in Corresponding PCT Application PCT/US 09/02004 on Jun. 3, 2009.

* cited by examiner

*Primary Examiner* — Traviss C McIntosh, III
(74) *Attorney, Agent, or Firm* — Lerner, David, Littenberg, Krumholz & Mentlik, LLP

(57) ABSTRACT

Disclosed are cyclopropanated carbohydrate compounds of formulas I and II:

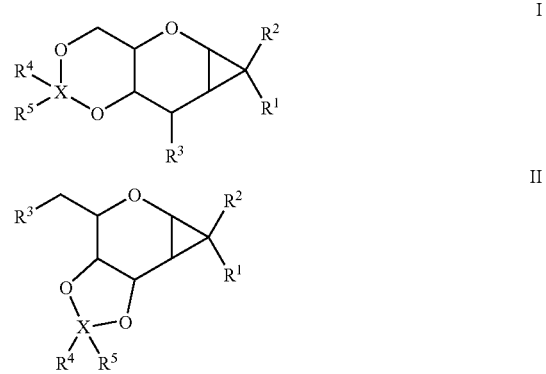

Also disclosed are methods of treating or preventing a central nervous system ailment by administering to an organism in need thereof an effective amount of a cyclopropanated carbohydrate compound of formula I or II and pharmaceutical compositions containing a cyclopropanated carbohydrate compound of formula I or II.

26 Claims, 51 Drawing Sheets

¹H NMR (500 MHz, CDCl₃)

| Compound | 5ht1a | 5ht1b | 5ht1d | 5ht1e | 5ht2a | 5ht2b | 5ht2c | 5ht3 | 5ht5a | 5ht6 | 5ht7 | Alpha1A |
|---|---|---|---|---|---|---|---|---|---|---|---|---|
| 4 | 2.5 | -18.2 | 13.7 | 3.4 | 19.4 | -9 | 4.4 | 6.1 | 27 | 26.5 | 24.9 | |
| 7 | -23 | -11.3 | 6.3 | 8.8 | 4.2 | -19.1 | -8.9 | -3.3 | 6.2 | 21.2 | 16.5 | |
| 10 | 17.7746 | 14.7 | 7.3 | 14.7 | 2 | -8.6 | 23.2 | 6 | 42.1 | 7.8 | 11.1 | -14.1 |
| 8b | 25.4226 | 24.7 | -4.4 | 24.7 | -9.8 | -27.5 | 12.3 | 0.9 | 25.6 | 18.3 | 24.5 | -15.6 |
| 9 | -8.8 | 2.9 | 5.4 | 5.3 | 22.5 | -19.9 | 2.1 | 7.9 | 13.8 | -11.5 | -14.1 | |
| 15 | -44.8 | -4.4 | 0.3 | 4.4 | 8.2 | -19.4 | 7 | 4.4 | 15 | -7.8 | -17 | |
| 3a | -3.18648 | -12.8 | 9.5 | -12.8 | 0.6 | | 10.6 | 20.6 | 35.7 | 0.1 | 12.4 | -7.7 |
| 5 | -14.6272 | -5.4 | 6.6 | -5.4 | -38.2 | 35.6 | -6.4 | 13.3 | 45.7 | 17.9 | 1 | 10.6 |
| 14 | 12.8096 | 20.5 | 6.1 | 20.5 | 2.2 | -31.6 | 21.3 | 2.9 | 38.9 | 16.3 | 12.9 | -17 |
| 14a | 6.42441 | 11.7 | 1.9 | 11.7 | 25.8 | -18.5 | 29.4 | -1 | 33.3 | 8.3 | 17.1 | -3.8 |
| 20a | -18.8 | -11 | 10.1 | 6.3 | 5.1 | 17 | 2.1 | -3.8 | 22.6 | 2 | -10.1 | |
| 16 | -26.2 | 3 | 14.5 | 11.3 | 7.2 | -16.5 | -2.8 | 3.3 | 39.2 | -4.3 | 5.5 | |
| 18 | -29.3 | -6.2 | 4.6 | 6.9 | 12.3 | -16.4 | -6.1 | 2.5 | 36.1 | -8.1 | -18.3 | |
| 19 | -39.1 | -11.4 | 4.9 | 12.6 | 10.3 | 23 | -16.9 | -8.2 | 13.7 | -9.1 | -15.6 | -8.6 |
| 17b | -17.3483 | 2.7 | 6.4 | 2.7 | 8.9 | -17.2 | 20.4 | 18.9 | 26.8 | 21.6 | 12.6 | |
| 20e | 11.7 | -10.1 | 16.3 | 14.7 | 14.7 | -15.9 | -9.6 | 0.1 | 16.1 | -16.3 | -8.9 | |
| 20c | -8.7 | -2.7 | 28.9 | 11.5 | 8.8 | -11.8 | -12.2 | -15.5 | 17.5 | 31.3 | 13.3 | -5.5 |
| 20f | -2.0321 | 14.6 | 25.1 | 14.6 | -19.4 | -19 | 37.3 | 25.3 | 42 | 10.9 | 11.5 | |
| 20d | -11.8 | -2.9 | 16.3 | 15.3 | 17.4 | | -16 | -2.2 | 21.5 | -4.1 | -14.7 | |

FIGURE 48

| Compound | Alpha1B | Alpha1D | Alpha2A | Alpha2B | Alpha2C | Beta1 | Beta2 | Beta3 | BZP Rat Brain Site | Ca+Channel |
|---|---|---|---|---|---|---|---|---|---|---|
| 4 | | | | | | -30.2 | -7 | 10.3 | | 55.7 |
| 7 | -1 | 25.1 | 28 | 41.2 | 22.6 | -10.8 | -16.9 | -11.2 | | 42.6 |
| 10 | | | -1 | | | 31.2 | -11.8 | 21 | 24.9 | -6.7 |
| 8b | -15.8 | -14.2 | -19 | -0.5 | 35.5 | 1.7 | 1.4 | 1.3 | 12.3 | 3.3 |
| 9 | | | | | | -0.1 | -2.1 | -19.1 | | 48.3 |
| 15 | | | | | | 5.6 | -7.9 | -16.6 | | 14 |
| 3a | 3.5 | 18.1 | 8.4 | 45.5 | 33.5 | 39.9 | -16.2 | 4.8 | 16.4 | 13 |
| 5 | 14.8 | -19.8 | 1.1 | 15.9 | 92.7 | 39 | -13.2 | 25.5 | -21.9 | 18.3 |
| 14 | -12.8 | -1 | -5.8 | 33.5 | 18.5 | 24.6 | -2.6 | -9 | 30.5 | -1.3 |
| 14a | -6.4 | -19 | -9.6 | 31.5 | 20 | -2.5 | 2.9 | -13.6 | 7.6 | 37.5 |
| 20a | | | | | | -2.8 | -18.3 | -12.5 | | -3.5 |
| 16 | | | | | | -3.9 | -1.5 | -6.3 | | 86.4 |
| 18 | | | | | 67.4 | 6.7 | -19.8 | -19.3 | | 2.3 |
| 19 | | | | | | -5.7 | -13.6 | | | 35.4 |
| 17b | 6.2 | -13.8 | -14 | -10.3 | | 20.9 | 7.3 | 14.2 | 8.2 | 15.1 |
| 20e | | | | | | -1.6 | -12.3 | -19.4 | | 64.3 |
| 20c | | | 30.2 | | 94.8 | -20 | -18.4 | 4.3 | | 64.8 |
| 20f | 1.8 | -0.2 | -16.3 | 17.4 | | 2.9 | -15.7 | -0.6 | 5.5 | 7.6 |
| 20d | | | | | | 6.9 | -8.3 | -18.6 | | 35.7 |

FIGURE 48 (con't)

| Compound | D1 | D2 | D3 | D4 | D5 | DAT | DOR | GabaA | H1 | H2 | H3 | H4 | KOR |
|---|---|---|---|---|---|---|---|---|---|---|---|---|---|
| 4 | 118 | -0.9 | 12.4 | 59.9 | 103.6 | 67.5 | -1.1 | -0.6 | 12.2 | 38.4 | 12.6 | -3.5 | -6.9 |
| 7 | 118 | -1.5 | 2.5 | 6.7 | 87.9 | 50 | -21.5 | 25.3 | 1.5 | 13.6 | 1.1 | -13.9 | -13.1 |
| 10 | 3.8 | 16.8 | | 30.4 | -1.3 | 2.3 | -4 | | 8 | 8.4 | | 15.4 | -3.1 |
| 8b | 7.5 | 16.3 | | 12.3 | 7.5 | 5.2 | 5.8 | | 12 | 19.4 | | 10.6 | -10.2 |
| 9 | 29.2 | 8 | 7.2 | 3.1 | 30.6 | 52.7 | -1.6 | 1.7 | -8.7 | 17.1 | 3.9 | -12.5 | -7.5 |
| 15 | -0.8 | -3.2 | 26.8 | 0.4 | -15.4 | 73.4 | 4.1 | 0 | 0.4 | 14.7 | -0.6 | -14.3 | -4.1 |
| 3a | 0.4 | 15.7 | | 21.6 | 7.9 | 23.3 | -6.3 | | 1.7 | 31.8 | | 17.1 | 6.6 |
| 5 | 21.3 | 7.5 | | 38 | -15.2 | 50.3 | -16.4 | | 11.9 | 37.5 | | 16 | 4.5 |
| 14 | -5.7 | 7.1 | | 32.5 | 16.2 | 8 | 1.3 | | -20.1 | 12.1 | | 9 | 9.7 |
| 14a | 3.2 | 0.6 | 1.4 | 11.1 | 13.6 | 11 | -2 | 7.6 | -13.6 | 12.7 | 0.4 | 9.7 | -1.5 |
| 20a | 103.8 | 0.2 | -0.6 | 6.8 | 27.9 | 23.5 | -19.5 | 4.4 | 18.7 | 20 | 11.1 | -19.1 | -0.5 |
| 16 | 78.4 | 19.8 | 5.6 | -3.4 | -6.9 | -18.2 | -11.8 | 9.3 | 0.8 | 20.9 | -4.6 | -25.5 | -4.3 |
| 18 | 5.8 | -11.7 | 3.8 | -5 | 33.9 | 77.5 | 3.5 | 1.6 | 2.2 | 17.3 | -10 | -22.5 | 0 |
| 19 | 5.5 | -3 | | -3.9 | 37.3 | 85 | -0.4 | | 9 | 16.5 | | -19 | -5.6 |
| 17b | 21.8 | 31.8 | | 25.6 | -10 | 5.5 | -5.6 | 1.2 | 3.3 | 24.8 | -5.5 | 7.2 | 9.8 |
| 20e | 18.2 | -1.2 | -2.8 | -2.4 | -0.7 | 94.2 | -13 | | 7.5 | 30.7 | | -25.1 | -4.3 |
| 20c | 118 | 2.5 | 4.5 | -3.2 | 102.8 | 72.9 | -17 | 18.4 | 8.6 | 24.7 | 8.7 | 1.2 | -2.5 |
| 20f | 7.7 | 4.8 | | 21.3 | -10.8 | 11.1 | -10.2 | | 21.2 | 26.4 | | 7.9 | 2 |
| 20d | 15 | -0.2 | 4.8 | -11.5 | 15.6 | 88.5 | -5.9 | -3.6 | 9 | 14.8 | -5.4 | -28.8 | -0.5 |

FIGURE 48 (con't)

| Compound | M1 | M2 | M3 | M4 | M5 | MOR | NET | NMDA PCP site | SERT | Sigma 1 | Sigma 2 |
|---|---|---|---|---|---|---|---|---|---|---|---|
| 4 | -10.3 | -2.9 | -13.1 | -4.4 | -17.4 | 12.5 | 43.1 | 57.2 | 7.5(AVE) | 15.2 | -142.5 |
| 7 | 7.1 | -5.7 | 0.1 | -18.4 | -6.3 | -14.6 | 48.1 | 42.7 | 6.5(AVE) | -24.5 | -7.7 |
| 10 | 34.2 | 20.5 | .8 | -1.6 | -3.1 | 7 | 84.1 | 7.8 | 6.8 | -18.9 | -8.3 |
| 8b | 14.6 | 10.6 | 7.3 | -.8 | 9.3 | -10.8 | 8.4 | 19.6 | 1.9 | 3.4 | 65.9 |
| 9 | -6.8 | -18.7 | -0.9 | -6.5 | 9.8 | 5.6 | 23.6 | 48.8 | 31.8(AVE) | 12.9 | -7.4 |
| 15 | -0.2 | -11.9 | 11.2 | 16.7 | 10.1 | 16.3 | 39.4 | 47.3 | 6.7(AVE) | 29.3 | 0.7 |
| 3a | 10.8 | 15.7 | -16.4 | -18.7 | -3 | 21.7 | 91.5 | 12.3 | 3.6 | 2 | 10.7 |
| 5 | 8.3 | 23.9 | -1 | 15.1 | 22.6 | 12.8 | | 28.7 | 12.6 | -8.8 | 39.9 |
| 14 | 24.2 | 10.3 | -4.8 | -0.3 | 2.6 | 2.5 | 86.7 | 10.3 | 4.6 | -19.5 | -15.3 |
| 14a | 17.5 | 8.9 | -1.9 | -14.9 | 15.2 | -3.2 | 59.4 | 8.2 | 10.7 | -18.7 | -14.8 |
| 20a | -12.2 | -1.8 | 5.1 | 4.4 | -3.5 | -14.2 | 56.2 | 18 | -0.0(AVE) | -7.4 | -4.1 |
| 16 | 11.6 | -3 | 16.6 | 17.5 | 18.5 | 1.2 | 36 | 66.5 | 0.640943 | 13.2 | -11.4 |
| 18 | -3.8 | -8.6 | -3.1 | 10.8 | 5.8 | 5.2 | 31.6 | 29.4 | 4.6(AVE) | 27.4 | 0.4 |
| 19 | -6.2 | -18.7 | 4.6 | 7.2 | 2.1 | 8.8 | 55.7 | 28.1 | 1.3(AVE) | 18.3 | 1.6 |
| 17b | 11 | 25.5 | -1.2 | 10.2 | 20.6 | 5.2 | 85.3 | | 12.9 | -19 | -11.1 |
| 20e | 3.2 | -13.9 | 13.8 | -1 | -6.9 | 1.8 | 72.8 | 21.5 | -2.6(AVE) | -17.9 | -1.2 |
| 20c | -4 | -12.8 | -7.5 | -1.1 | -17.4 | -10.6 | 39.9 | 44.5 | 17.4(AVE) | -8.5 | 11 |
| 20f | 8 | -0.8 | -14.4 | -4.7 | 12.8 | 1.8 | 93.8 | 5.2 | 4.5 | -2.6 | 7.8 |
| 20d | -14.2 | -19.5 | 4.4 | -4.4 | -12.2 | -0.1 | 60.3 | 21.2 | 3.2(AVE) | -3.9 | 2.7 |

FIGURE 48 (Con't)

CYCLOPROPANATED CARBOHYDRATES

CROSS REFERENCE

This application claims the benefit of the filing dates of U.S. Provisional Patent Application Nos. 61/072,087 filed Mar. 27, 2008 and 61/125,732 filed Apr. 28, 2008, the disclosures of which are hereby incorporated herein by reference.

BACKGROUND OF THE INVENTION

Although there are a wide variety of compounds available on the market for the treatment of CNS disorders, discovery chemists are still searching for new compounds with better efficacy profiles and faster onsets of action. The anticonvulsant topiramate has a very unusual structure compared to most other anticonvulsants. It is a CNS-active small-molecule carbohydrate. The compound consists of a bis-O-isopropylidene-protected fructopyranose sulfamate.

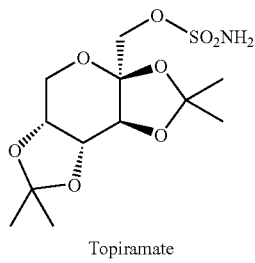

Topiramate

Topiramate is a very rare example of a CNS-active carbohydrate. A small series of carbohydrates and sulfamates were previously made and tested for anticonvulsant activity. Some analogs exhibited moderate anticonvulsant activity, including compounds A and B:

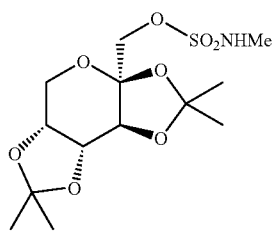

A

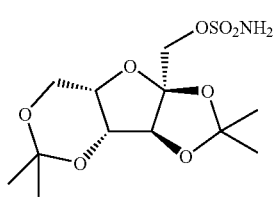

B

However, in comparison to the analogs, topiramate exhibited greater anticonvulsant activity.

Cyclopropanes have been targeted by medicinal chemists in a biological context because of their metabolic stability. This ring architecture has been successfully exploited in a variety of biological compounds. Furthermore, compounds that are structurally similar to cyclopropanated carbohydrates, such as 7-(hydroxyimino)cyclopropa[b]chromen-1a-carboxylate (Compound C), are active agonists for the metabotropic glutamate receptors, which are currently being examined for the treatment of depression.

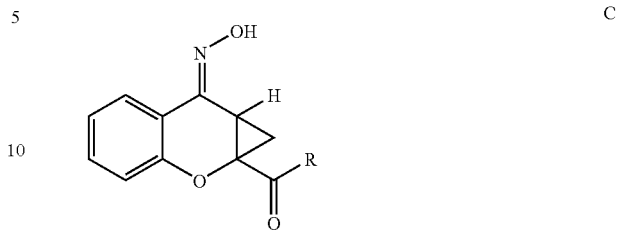

C

SUMMARY OF THE INVENTION

Accordingly, a series of novel cyclopropanated carbohydrates were made including functionalities of known successful carbohydrate-based antiepileptics. In addition successful architectural elements of topiramate derivatives were also incorporated into the compounds.

A first aspect of the present invention is directed to a compound of formula I or formula II:

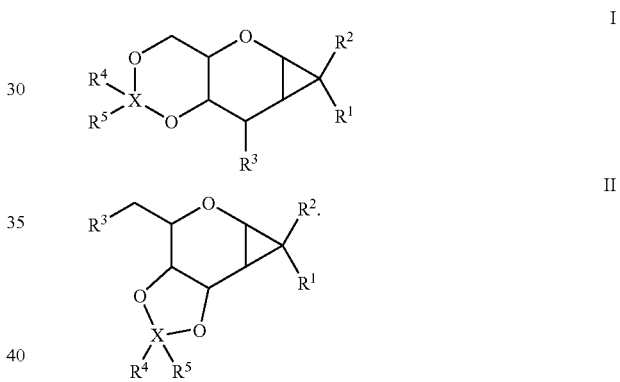

In one embodiment, $R^1$ represents hydrogen or a halogen. $R^2$ represents a halogen, an ester group or a —$CH_2R^6$ group and $R^6$ represents —OH, a halogen, a —$SR^7$ group, an amino group, or a —$NR^8R^9$ group and $R^7$, $R^8$, and $R^9$ each independently represent hydrogen, an alkyl group, an aryl group, or a heteroaryl group, provided that when $R^1$ represents hydrogen, $R^2$ is an ester group or a —$CH_2R^6$ group, and when $R^1$ represents a halogen, $R^2$ is a halogen. $R^3$ represents —OH, an ether, an oxime, or a sulfonamide. X represents a silicon or carbon, provided that when X represents a silicon, $R^4$ and $R^5$ each independently represent a substituted or unsubstituted, branched or unbranched, $C_1$-$C_4$ alkyl group, and when X represents a carbon, i) $R^4$ and $R^5$ are each independently a substituted or unsubstituted, branched or unbranched, $C_1$-$C_4$ alkyl group, or ii) $R^4$ represents H and $R^5$ represents a substituted or unsubstituted benzylidene group.

The compounds of the present invention are novel cyclopropanated carbohydrates. Certain of the compounds of the present invention have exhibited activity in CNS receptor assays. In addition, certain of the compounds of the present invention have exhibited anticonvulsant activity in mouse and rat models. Processes for making these compounds, products such as dosage forms including these compounds, and methods of their use are also contemplated.

BRIEF DESCRIPTION OF THE DRAWINGS

FIGS. 1 and 2 are NMR Spectra for Compound 14a.
FIGS. 11 and 12 are NMR Spectra for Compound 6a.
FIGS. 17 and 18 are NMR Spectra for Compound 8a.
FIG. 27 is a NMR Spectra for Compound 17a.
FIGS. 30 and 31 are NMR Spectra for Compound 20a.
FIGS. 46 and 47 are NMR Spectra for Compound 3a.
FIG. 48 is a table reporting the results of the National Institute of Mental Health's Psychoactive Drug Screening Program ("PDSP") screening of compounds of the present invention.

DETAILED DESCRIPTION OF THE INVENTION

Figure 1:
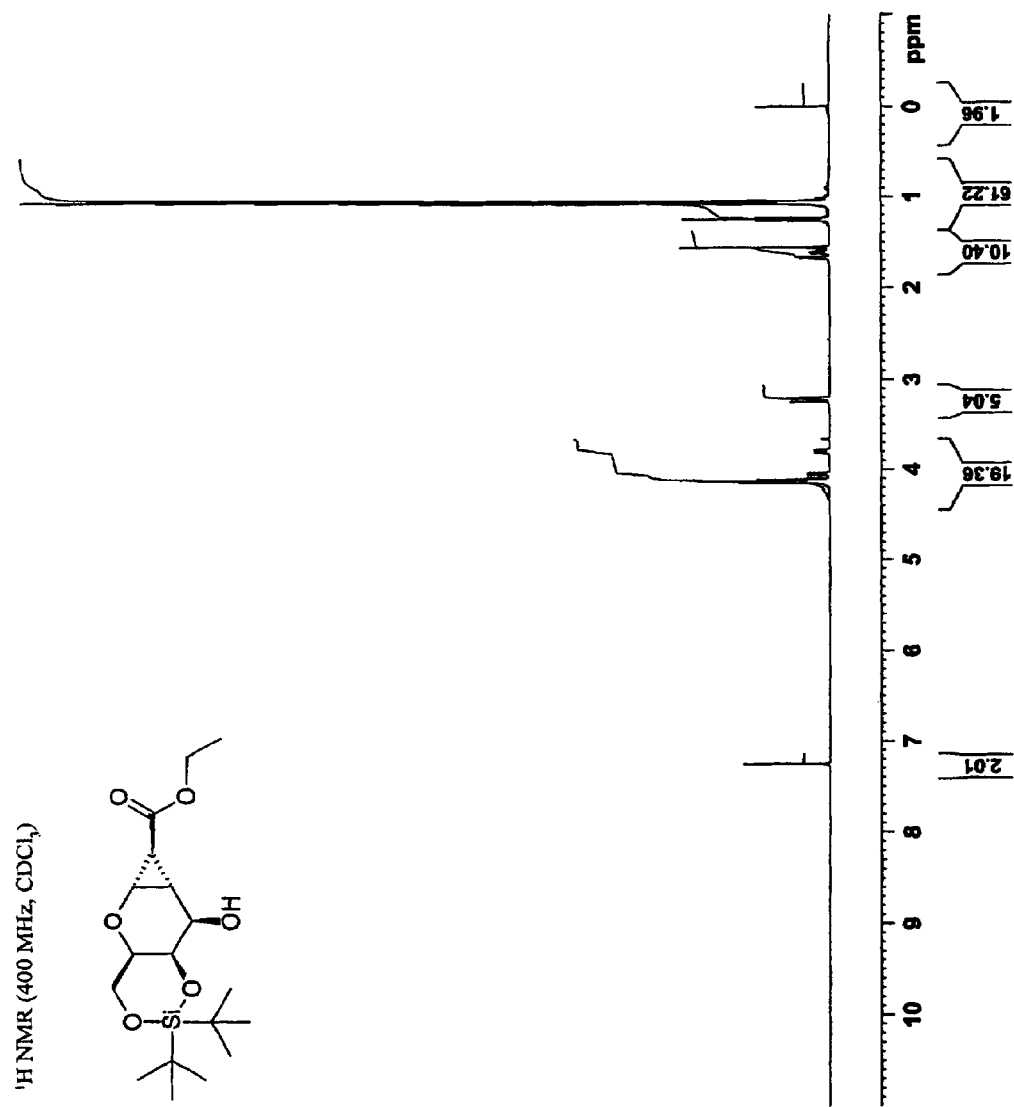

The compounds of the present invention are cyclopropanated derivatives of D-glycal, such as D-glucal or D-galactal. The compounds of the present invention are of two general formulas:

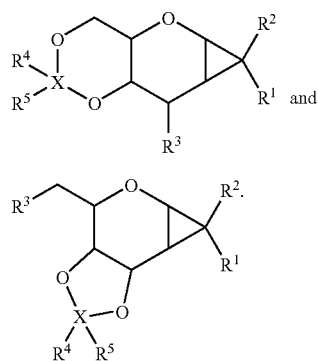

These basic formulas are derivatized to produce various cyclopropanated carbohydrate compounds.

In an embodiment of the present invention, the compound may be derivatized at $R^1$ and $R^2$ to include two halogens. In certain embodiments of the present invention, $R^1$ and $R^2$ are the same and are either chlorine or bromine. In another embodiment, $R^1$ is hydrogen and $R^2$ represents an ester group. In certain embodiments, $R^1$ is hydrogen and $R^2$ is a methyl ester group, ethyl ester group, or tert-butyl ester group. In yet another embodiment, $R^1$ is hydrogen and $R^2$ represents a —$CH_2R^6$ group in which $R^6$ represents a —$SCH_3$ group, an amino group, or a —$N(CH_3)_2$ group.

The formulas may also be derivatized at $R^3$. $R^3$ may be a hydroxide, an ether, an oxime, or a sulfonamide. In an embodiment of the present invention, the ether is methyl ether. In another embodiment, the oxime is, for example, =N—OH. In a further embodiment, the sulfonamide is a sulfonamide group (e.g., —$OSO_2NH_2$), or a N,N'-dimethyl-sulfonamide group (e.g., —$OSO_2N(CH_3)_2$).

X may be a silicon or carbon. In an embodiment of the present invention, $R^4$ and $R^5$ may each independently be a substituted or unsubstituted, branched or unbranched, $C_1$-$C_4$ alkyl group. In an embodiment of the present invention, X is silicon and $R_4$ and $R_5$ are both tert-butyl groups. In another embodiment of the present invention, X is carbon and $R_4$ and $R_5$ are both methyl groups. In yet a further embodiment, X is carbon, $R^4$ is hydrogen, and $R^5$ is a substituted or unsubstituted benzylidene group. In certain embodiments, the benzylidene group is substituted with one or more substituent selected from a methoxy group, a tert-butyl group, a trifluoromethyl group, an isopropyl group, a halogen, —OH, —$SCH_3$, and —$N(CH_3)_2$. In certain embodiments, the benzylidene group is an unsubstituted benzylidene group, a p-methoxybenzylidene group, a p-tert-butylbenzylidene group, a m-methoxybenzylidene group, a trifluoromethylbenzylidene group, a p-isopropylbenzylidene group, or a difluorobenzylidene group.

The compounds of the present invention include, without limitation, those of the following formulae:

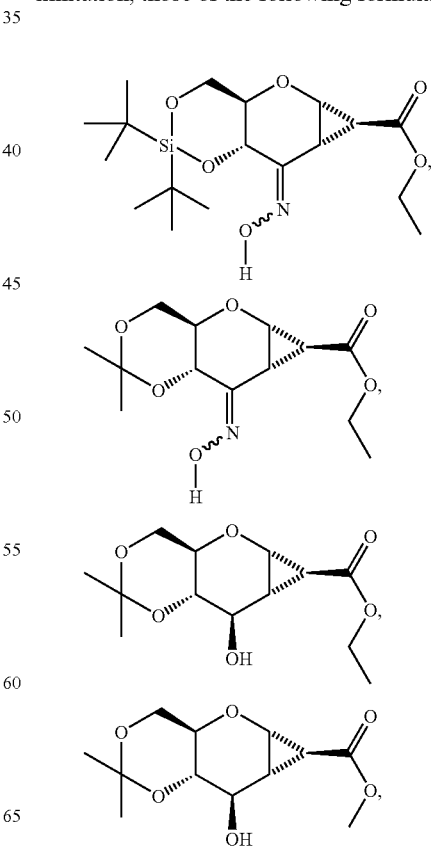

5
-continued
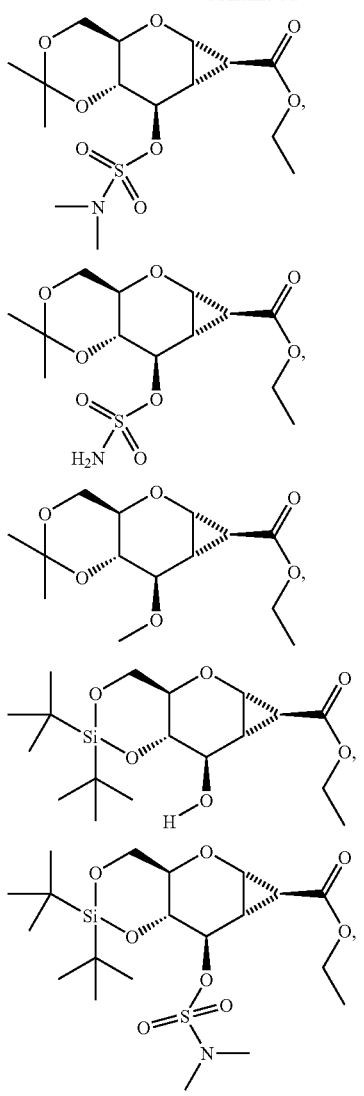
6
-continued
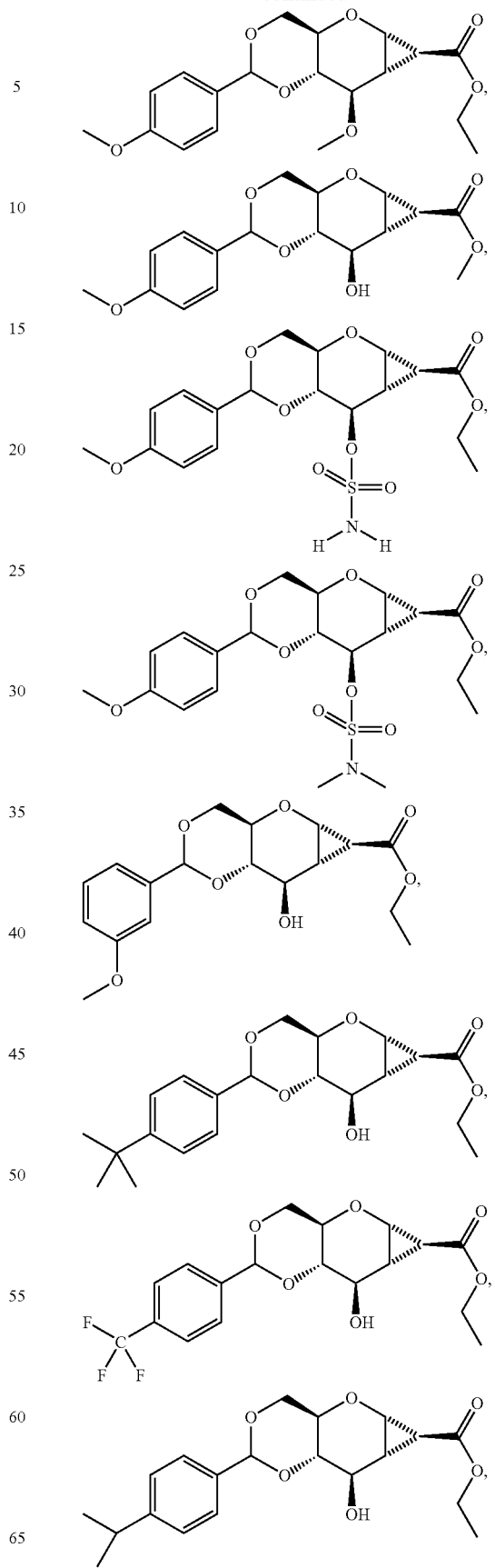

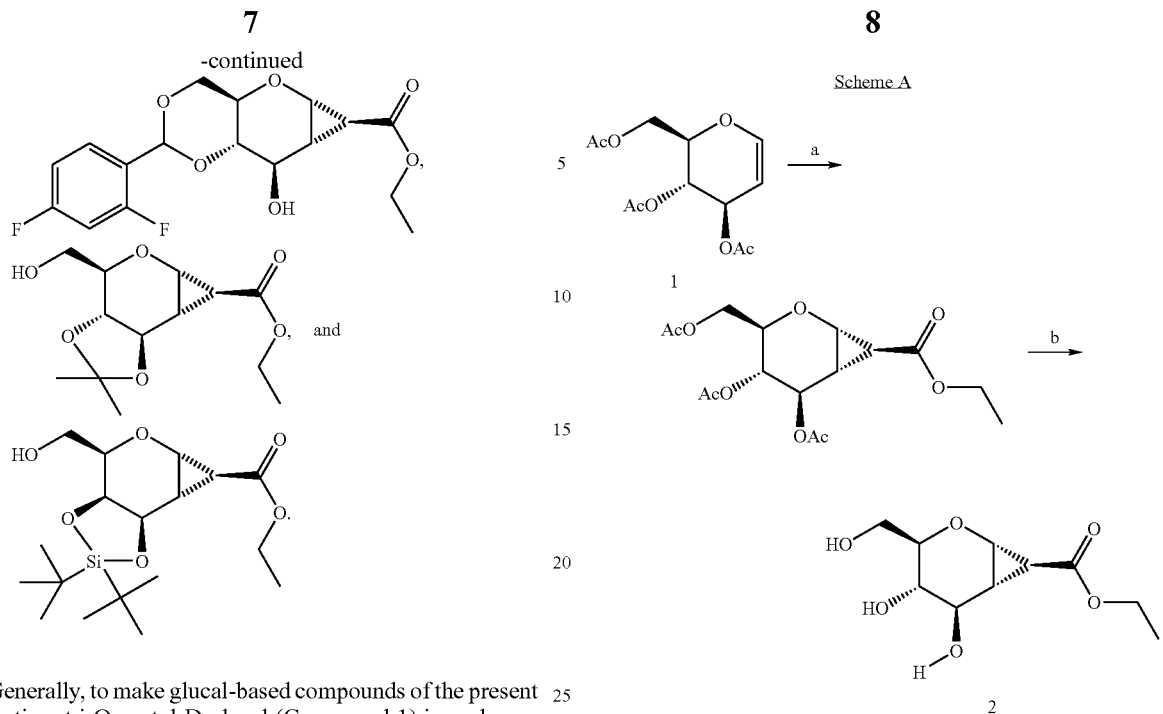

Generally, to make glucal-based compounds of the present invention, tri-O-acetyl-D-glucal (Compound 1) is cyclopropanated with rhodium acetate dimer and ethyldiazoacetate (Scheme A, reaction (a)). The product is next deacetylated with sodium ethoxide in ethanol to produce the cyclopropanated glucal (Compound 2) (Scheme A, reaction (B)).

Glucal derivatives may then be synthesized according to Scheme B from the cyclopropanated glucal starting material (Compound 2) produced by Scheme A.

Scheme B
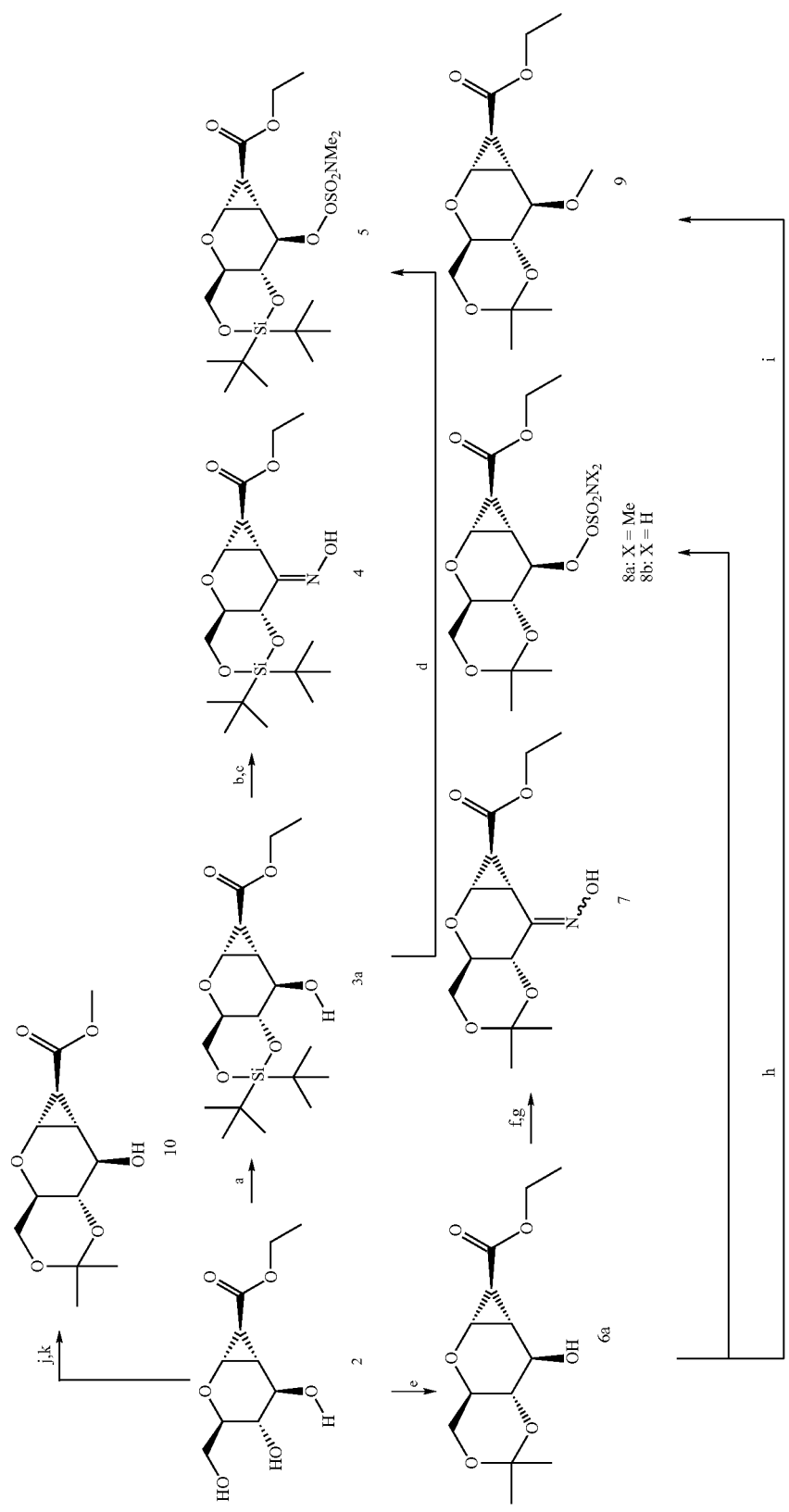

General reactants and reaction conditions include: Reaction (a)—di-t-BuSi(OTf)$_2$, 2,6-lutidine, DMF, at −20° C. warm to room temperature, and react for 1 hour. Reaction (b)—Dess-Martin periodinane. Reaction (c)—Reflux with hydroxylamine hydrochloride, TEA, and EtOH. Reaction (d)—Add NaH, DCM, and Me$_2$NSO$_2$Cl at 0° C. and warm to room temperature. Reaction (e)—(MeO)$_2$CMe$_2$, DMF, and p-TsOH. Reaction (f)—Dess-Martin periodinane. Reaction (g)—Hydroxylamine hydrochloride, TEA, and EtOH at 60° C. Reaction (h)—NaH and DMF at 0° C. (Compound 8a: Me$_2$NSO$_2$Cl, 50% Compound 8b: H$_2$NSO$_2$Cl). Reaction (i)—NaH and DMF at 0° C., add MeI. Reaction (j)—NaOMe and MeOH. Reaction (k)—2,2-dimethoxypropane, p-TsOH, and DMF (2 steps).

Generally, galactal derivatives may be synthesized according to Scheme C staring from tri-O-benzoyl-D-galactal (Compound 11).

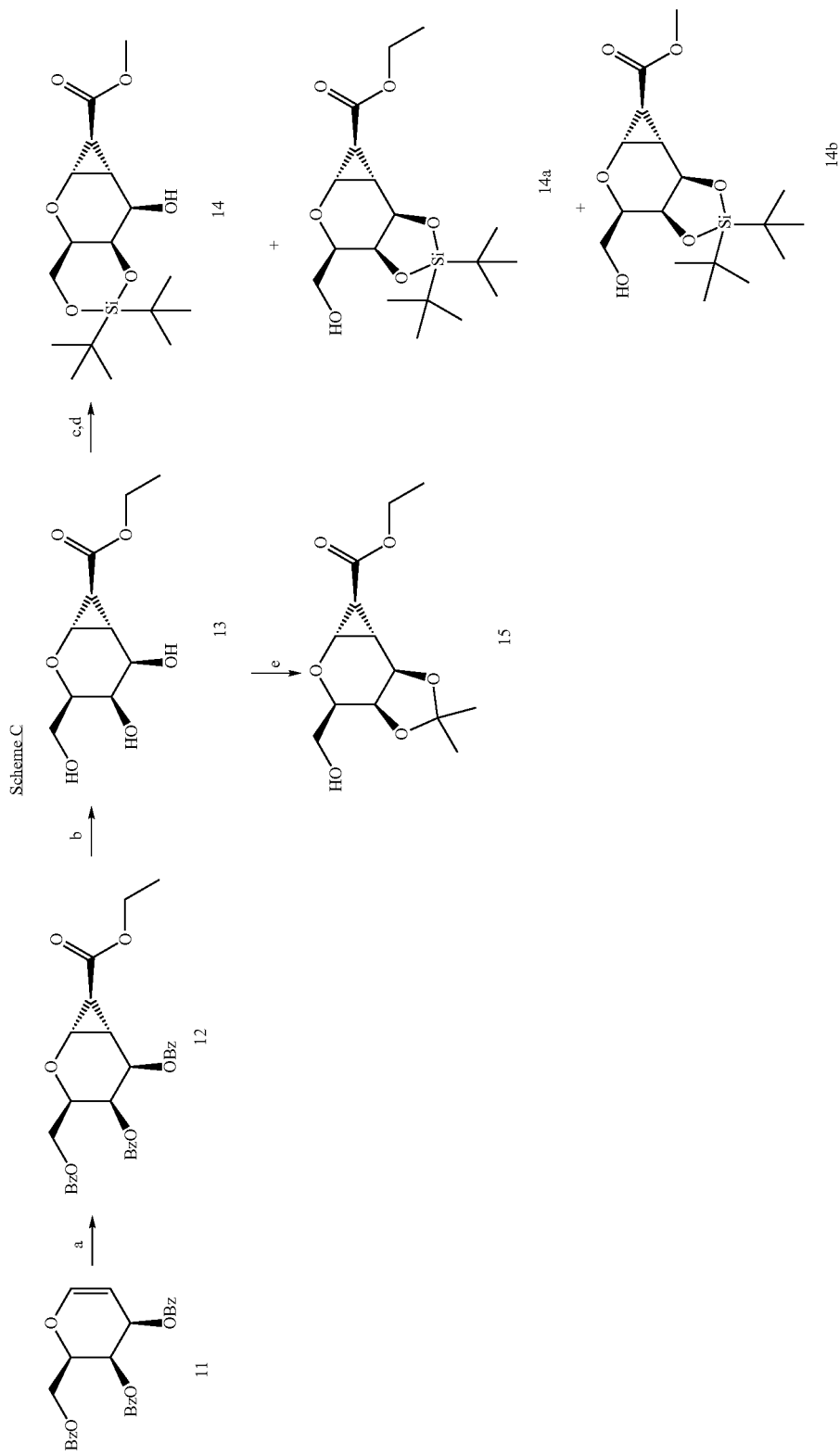

General reactants and reaction conditions are as follows: Reaction (a)—EDA, Rh$_2$(OAc)$_4$, and DCM. Reaction (b)—NaOEt and EtOH. Reaction (c)—di-t-BuSi(OTf)$_2$, 2,6-lutidine, and DMF at 0° C. Reaction (d)—MeOH and SiO$_2$. Reaction (e)—2,2-dimethoxypropane, DMF, and p-TsOH.

Benzylidene derivatives may be synthesized according to Scheme D starting from the cyclopropanated glucal starting material (Compound 2) produced by Scheme A.

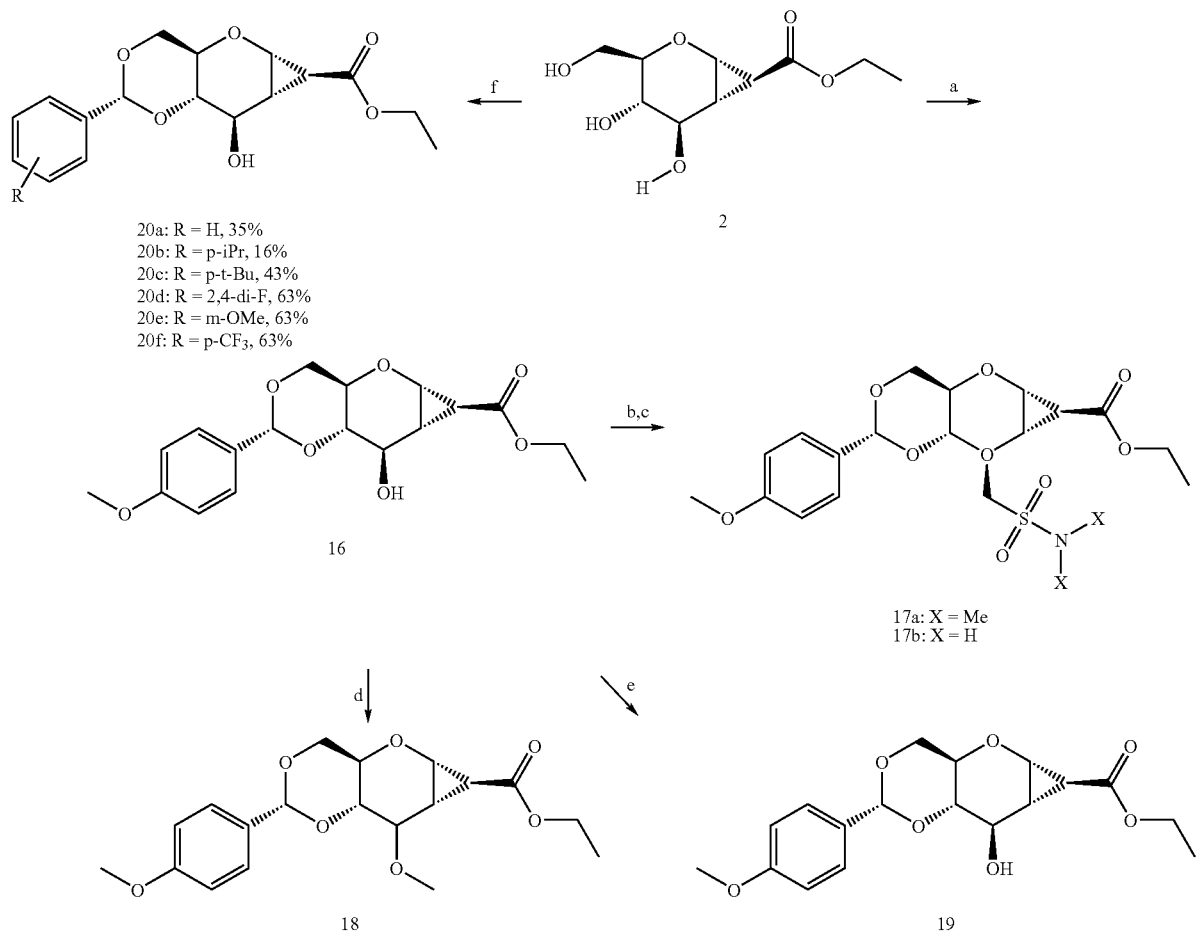

General reactants and reaction conditions include: Reaction (a)—PMB dimethyl acetal, p-TsOH, and DMF. Reaction (b) NaH and DMF at 0° C., add Me$_2$NSO$_2$Cl. Reaction (c)—NaH and DMF at –30° C., add H$_2$NSO$_2$Cl. Reaction (d)—NaH, DMF, and MeI at 0° C. Reaction (e)—MeOH/NH$_3$. Reaction (f)—ArCHO (20a-f as indicated above) and ZnCl$_2$.

Another aspect of the invention is treating or preventing a central nervous system ailment or condition. In these methods, an effective amount of a cyclopropanated carbohydrate compound of the present invention is administered to an organism in need thereof. The term "organism in need thereof" means an organism suffering from or susceptible to a central nervous system ailment. This include animals, in particular cats, dogs, and domestic animals, as well as humans. The term "central nervous system ailment" means an ailment caused by or related to a disorder of the brain and/or spinal column, including, without limitation, epilepsy, bipolar disorder, addiction, schizophrenia, depression, attention deficit hyperactivity disorder, and attention deficit disorder.

As used herein, the term "effective amount" means the amount of a composition or substance sufficient to produce the desired effect in the organism to which the composition or substance is administered. In an embodiment, an effective amount of at least one cyclopropanated carbohydrate compound of the invention is from about 0.1 milligram to about 500 milligrams per kilogram of body weight per day. In other embodiments, an effective amount of the cyclopropanated carbohydrate compound is from about 1 milligram to about 100 milligrams per kilogram of body weight per day, and in other embodiments from about 5 to about 50 milligrams per kilogram of body weight per day.

Pharmaceutical compositions of the present invention contain an amount of at least one cyclopropanated carbohydrate compound of the invention effective to treat or prevent a central nervous system ailment. Dosage forms, modes of administration, and dosage amounts of cyclopropanated carbohydrate or pharmaceutical compositions containing cyclopropanated carbohydrate according to the present invention may be determined empirically, and making such determinations is within the skill of the art. It is understood by those skilled in the art that the dosage amount will vary with, amongst other things, the route of administration, the number of doses to be administered per dosing interval (day, week, month, year), the rate of excretion, the duration of the treatment, the identity of any other drugs being administered, the age, size, and species of animal, and like factors well known in the arts of medicine and veterinary medicine. In general, a suitable dose of at least one cyclopropanated carbohydrate according to the invention will be that amount of the compound, which is the lowest dose effective to produce the desired effect. The effective dose of cyclopropanated carbohydrate may be administered as a single dose or as two, three, four, five, six, or more sub-doses, administered separately at appropriate intervals throughout the day. Each dose may be provided in single dosage form, such as a tablet, capsule, liquid, and the like, or distributed in multiple dosage forms.

The cyclopropanated carbohydrate may be administered in any desired and effective manner: as pharmaceutical compositions for oral ingestion, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. In certain embodiments, the cyclopropanated carbohydrate is administered orally or intraperitoneally. The cyclopropanated carbohydrate may be encapsulated or otherwise protected against gastric or other secretions, if desired.

While it is possible for the pharmaceutical compositions to comprise only the cyclopropanated carbohydrate of the invention, they more often comprise the cyclopropanated carbohydrate as an active ingredient in admixture with one or more pharmaceutically-acceptable excipients. These pharmaceutical compositions may be formulated into pharmaceutically-acceptable dosage forms by conventional methods known to those of skill in the art.

Pharmaceutical excipients are well known in the art. Each excipient used in a pharmaceutical composition of the invention must be "acceptable" in the sense of being compatible with the other ingredients of the formulation and not injurious to the subject. Excipients suitable for a selected dosage form and intended route of administration are well known in the art, and acceptable excipients for a chosen cyclopropanated carbohydrate dosage form and method of administration can be determined using ordinary skill in the art.

These excipients are well known in the art and include (1) fillers or extenders, such as, sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and triglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, salicylate, etc. (2) binders, such as carboxymethylcellulose, alginates, gelatin, polyvinyl pyrrolidone, hydroxypropylmethyl cellulose, sucrose and acacia; (3) humectants; (4) disintegrating agents, such, as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) inert diluents, such as water or other solvents; (13) preservatives; (14) surface-active agents; (15) dispersing agents; (16) control-release or absorption-delaying agents, such as hydroxypropylmethyl cellulose, other polymer matrices, biodegradable polymers, liposomes, microspheres, aluminum monostearate gelatin, and waxes; (17) opacifying agents; (18) adjuvants; (19) emulsifying and suspending agents; (20) propellants, such as chlorofluorohydrocarbons and volatile unsubstituted hydrocarbons, such as butane and propane; (21) antioxidants; (22) agents which render the formulation isotonic with the blood of the intended recipient, such as sugars and sodium chloride; (23) thickening agents; (24) coating materials, such as lecithin; and (25) sweetening, flavoring, coloring, and perfuming agents.

Pharmaceutical compositions suitable for oral administration may be in the form of solids and liquids, including capsules, cachets, pills, tablets, powders, granules, a solution or a suspension in an aqueous or non-aqueous liquid, an oil-in-water or water-in-oil liquid emulsion, an elixir, a syrup, a pastille, a bolus, an electuary, or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared by mixing the active ingredient(s) with one or more pharmaceutically-acceptable excipients. A tablet may be made by compression or molding, optionally with one or more additional ingredient. The cyclopropanated carbohydrates may also be granulated prior to being compressed, with or without additional excipients or ingredients. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide controlled or delayed release of the active ingredient therein. These compositions may also optionally contain opacifying agents and may be of a composition such that they release the active ingredient only, or preferentially, in a certain portion of the gastrointestinal tract, optionally, in a controlled or delayed manner. The active ingredient can also be in microencapsulated form.

Liquid dosage forms for oral administration include pharmaceutically-acceptable emulsions, microemulsions, solutions, suspensions, syrups, and elixirs. The liquid dosage forms may contain suitable inert diluents commonly used in the art. Besides inert diluents, oral compositions commonly include, for example, wetting agents, emulsifying and suspending agents, preservatives, and sweetening, flavoring, coloring, and perfuming agents. Suspensions commonly contain suspending agents.

Dosage forms for the topical or transdermal administration include powders, sprays, ointments, pastes, creams, lotions, gels, solutions, patches, drops, and inhalants. The active compound may be mixed under sterile conditions with a suitable pharmaceutically-acceptable excipient. Powders and sprays may contain propellants.

Pharmaceutical compositions suitable for parenteral administration comprise the cyclopropanated carbohydrate in combination with one or more pharmaceutically-acceptable sterile isotonic aqueous or non-aqueous solutions, dispersions, suspensions, or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These compositions commonly contain wetting agents, emulsifying agents, and dispersing agents. It may also be desirable to include isotonic agents. In addition, prolonged absorption of the injectable pharmaceutical form may be brought about by the inclusion of agents which delay absorption.

In some cases, in order to prolong the effect of a drug, it is desirable to slow its absorption from subcutaneous or intramuscular injection. This may be accomplished by the use of a liquid suspension of crystalline or amorphous material having poor water solubility.

The rate of absorption of the drug then depends upon its rate of dissolution which, in turn, may depend upon crystal size and crystalline form. Alternatively, delayed absorption of a parenterally-administered drug may be accomplished by dissolving or suspending the drug in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid, for example water for injection, immediately prior to use. Extemporaneous injection solutions and suspensions may be prepared from sterile powders, granules, and tablets of the type described above.

The invention is further described in detail by reference to the following experimental examples. These examples are provided for the purpose of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLES

General Synthetic Methods

All reactions were performed under an inert atmosphere of nitrogen (Auto Gas Light, zero grade) unless otherwise specified. Reagents and solvents were transferred using an inert atmosphere syringe or cannula techniques. Anhydrous solvents were purchased from Aldrich Chemical Company and were used as received unless otherwise specified. THF was used as received from Aldrich Chemical Company or freshly distilled from sodium/benzophenone ketyl. Proprionitrile was freshly distilled from 4 Å molecular sieves prior to use. Glycal (e.g., tri-O-acetyl-D-glucal and tri-O-benzyl-D-glucal) starting materials and dimethylsulfamoyl chloride were purchased from Aldrich. $^1$H NMR and $^{13}$C NMR spectra were acquired on a Bruker Avance (400 MHz, Lundbeck U.S.A., Paramus, N.J.) or on a Varian Inova ASSOO (500 MHz) spectrometer in chloroform-d, methanol-d4 with tetramethylsilane as the internal standard. Chemical shifts (δ) are expressed in ppm, coupling constants (J) are expressed in Hz, and splitting patterns are described as follows: s=singlet; d=doublet; t=triplet; q=quartet; qAB=AB quartet; quintet; sextet; septet; br=broad; m=multiplet; dd=doublet of doublets; dt=doublet of triplets; td=triplet of doublets; ddd=doublet of doublet of doublets.

Elemental analyses were performed by Robertson Microlit Laboratories, Inc. (Madison, N.J.). Unless otherwise specified, all samples were dried to constant weight. Unless otherwise noted, high resolution mass spectra were obtained using electrospray ionization (ESMS, Micromass Platform II or Quattro Micro, Hunter College, CUNY, New York, N.Y.); (M+H)$^+$, (M+Na)$^+$, and (M+NH)$^+$ are reported. Thin-layer chromatography was performed on aluminum plates that had been precoated with silica gel 60 F254. Preparative TLC was performed on glass sheets that had been pre-coated with silica gel GF (2000 μm, Analtech). Flash chromatography was performed on Merck silica gel (230-400 mesh). Melting points (mp) were determined in open capillary tubes on a MeI-Temp apparatus and are uncorrected.

Example 1

Preparation of (1R,1aS,2R,2aS,6aR)-4,4-di-tert-butyl-2-hydroxy-hexahydro-3,5,7-trioxa-4-sila-cyclopropa[b]naphthalene-1-carboxylic acid (S)-ethyl ester (Compound 3a)

Figure 46:
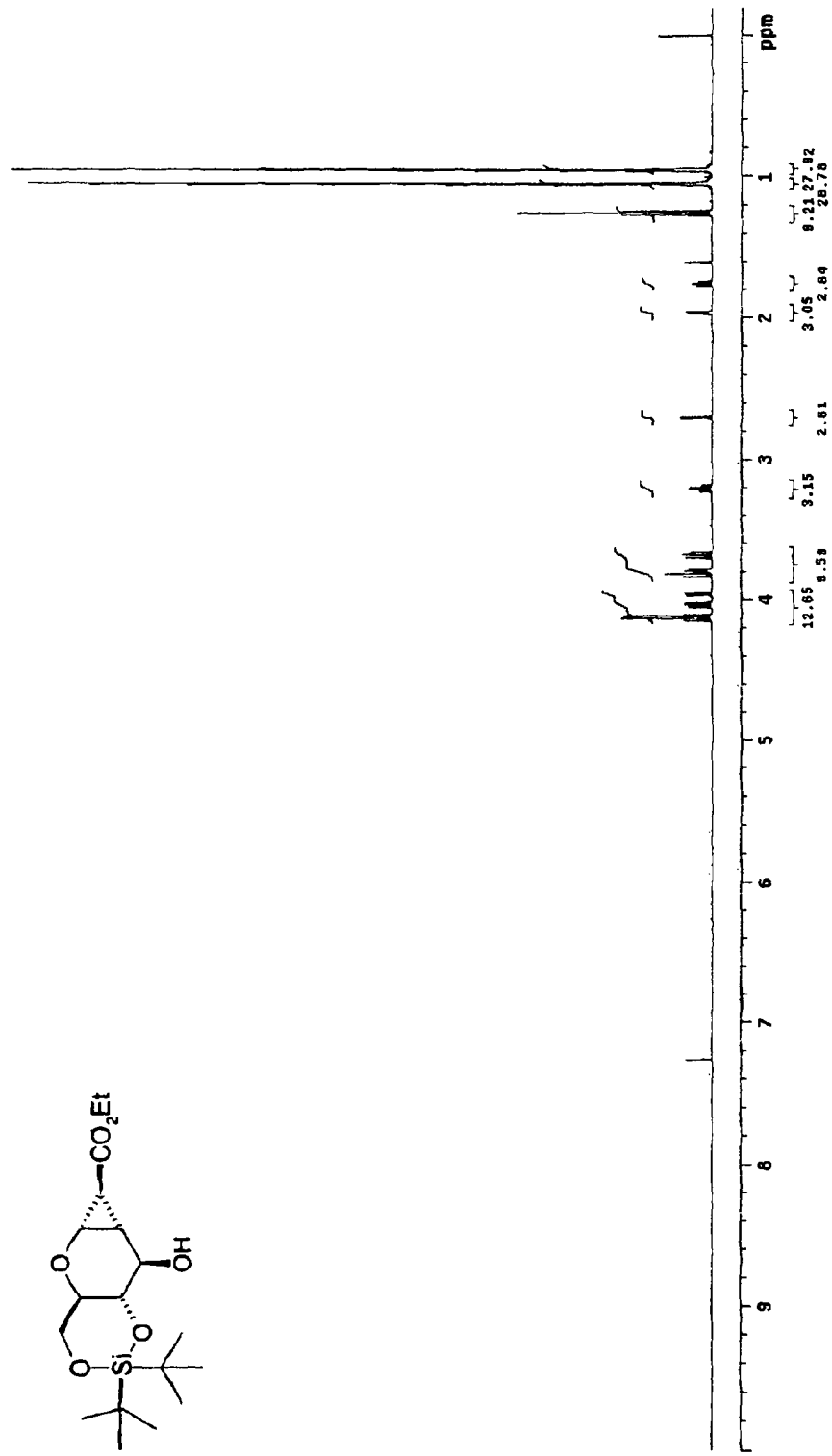
Figure 47:
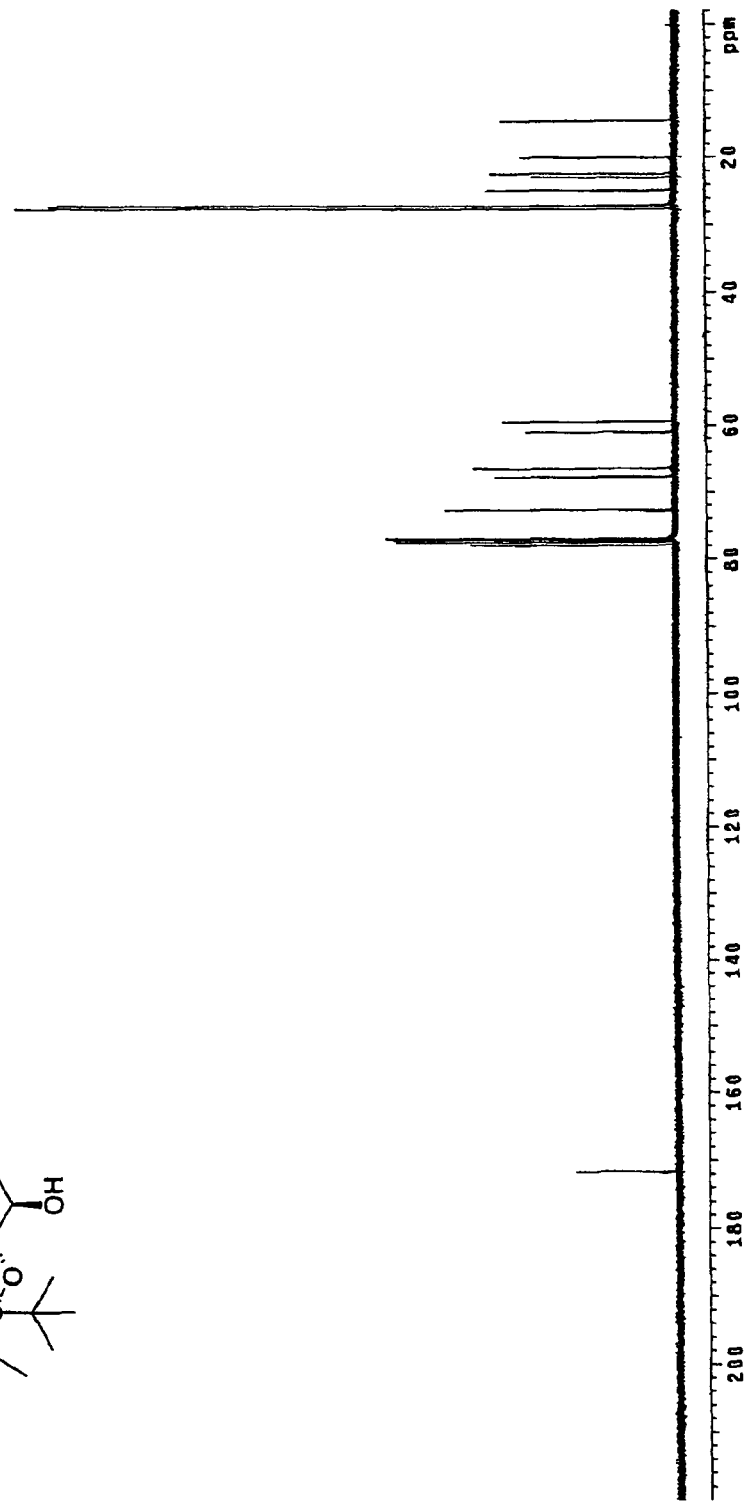

Di-tert-butylsilyl ditriflate (Di-t-BuSi(OTf)$_2$) was added dropwise to a solution of cyclopropanated glucal (Compound 2) (0.37 g, 1.6 mmol) and 2,6-lutidine (0.43 g, 4.0 mmol) in 10 mL of DMF at −30° C. The reaction mixture was allowed to stir at −20° C. for 1.5 h, allowed to warm to 0° C., and stirred at 0° C. for 0.5 h. The reaction was quenched with water at 0° C., the crude was extracted with DCM (3×75 mL), and the organics were washed with water (3×75 mL) and brine (1×75 mL). The organic layer was dried over Na$_2$SO$_4$, filtered, and concentrated in vacuo. Column chromatography (SiO$_2$, a gradient of pure hexanes to a ratio of 7:13 ethyl acetate in hexanes) afforded a white solid (0.43 g, 1.1 mmol) 72% yield: mp=99-100° C. $^1$H NMR (500 MHz, CDCl$_3$): δ 4.13 (q, 2H, J=7.0 Hz), 4.04 (dd, $^1$H, J=10.5, 4.5 Hz), 3.96 (dd, 1H, J=7.5, 3.0 Hz), 3.82 (apparent t, 1H, J=10.0 Hz), 3.80 (d, broad, 1H, J=8.5 Hz), 3.70 (dd, 1H, J=9.8, 8.0 Hz), 3.20 (ddd, 1H, J=10.0, 10.0, 5.0 Hz), 2.70 (d, 1H, J=1.5 Hz), 1.96 (dd, 1H, J=5.5, 2.5 Hz), 1.77-1.74 (m, 1H), 1.26 (t, 3H, J=7.0 Hz), 1.05 (s, 9H, t-butyl), 0.96 (s, 9H, t-butyl) (FIG. 46). $^{13}$C NMR (500 MHz, CDCl$_3$): δ 171.5, 77.7, 72.5, 67.5, 66.2, 60.8, 59.3, 27.4 (3 C's), 26.9 (3 C's), 24.6, 22.7, 22.2, 19.8, 14.2 (FIG. 47). HRMS (m/z): [M]$^+$ calculated for C$_{18}$H$_{32}$O$_6$Si, 372.1968. found 372.1976 (Δ 0.8 mmu).

Example 2

General Procedure for the Preparation of Compounds 14, 14a, and 14b

Di-tert-butylsilyl ditriflate was added dropwise to a solution of cyclopropanated galactal staring material (Compound 13) (0.57 g, 2.5 mmol) and 2,6-lutidine (0.66 g, 6.2 mmol) in 10 mL of DMF at −30° C. The reaction mixture was stirred at −20° C. for 1.5 h, allowed to warm to 0° C., and stirred at 0° C. for an additional 0.5 h. The reaction was quenched with water at 0° C., the crude was extracted with DCM (75 mL), and the organics were washed with water (3×70 mL) and brine (1×70 mL). The organic layer was dried over Na$_2$SO$_4$, filtered, and concentrated in vacuo. The crude mixture was purified by column chromatography to afford the following compounds.

(1S,1as,3R,3aS,6aR,6bS)-5,5-di-tert-butyl-3-hydroxymethyl-hexahydro-2,4,6-trioxa-5-sila-cyclopropa[e]indene-1-carboxylic acid ethyl ester (Compound 14)

Figure 4:
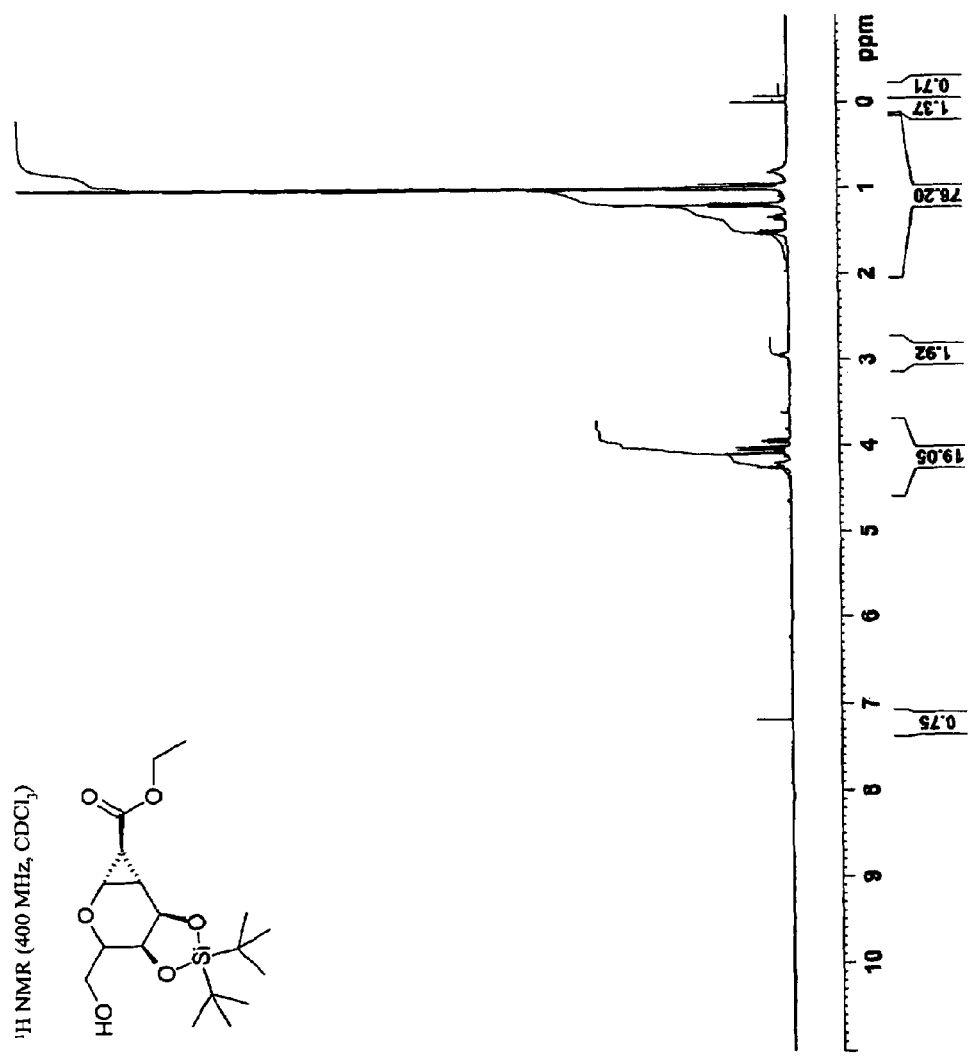
FIG. 4 is a NMR Spectra for Compound 14.

Column chromatography (SiO$_2$, a gradient of pure hexanes to a 3:10 ratio of ethyl acetate in hexanes) on the crude mixture afforded a colorless glass (0.15 g, 0.55 mmol) 16% yield. $^1$H NMR (400 MHz, CDCl$_3$): δ 4.41-4.33 (m, 2H), 4.28-4.17 (m, 5H), 4.01 (dd, 1H, J=6.0, 1.0 HZ), 3.09 (dd, 1H, J=11.0 Hz), 1.67 (dd, 1H, J=10.0, 6.5 Hz), 1.51-1.47 (m, 1H), 1.34 (t, 3H, J=7.0 Hz), 1.01 (s, 9H), 0.99 (s, 9H) (FIG. 4). $^{13}$C NMR (500 MHz, CDCl$_3$): δ 170.5, 73.2, 69.5, 68.0, 62.8, 60.3, 56.0, 27.8 (3 C's), 27.1 (3 C's), 23.4, 21.2, 21.0, 20.2, 14.3. HRMS (m/z): [M]$^+$ calculated for C$_{18}$H$_{32}$O$_6$Si, 372.1968. found 372.1974 (Δ 0.6 mmu).

(1R,1as,2R,2aR,6aR)-4,4-di-tert-butyl-2-hydroxy-hexahydro-3,5,7-trioxa-4-silacyclopropa[b]naphthalene-1-carboxylic acid (S)-ethyl ester (Compound 14a)

Figure 2:
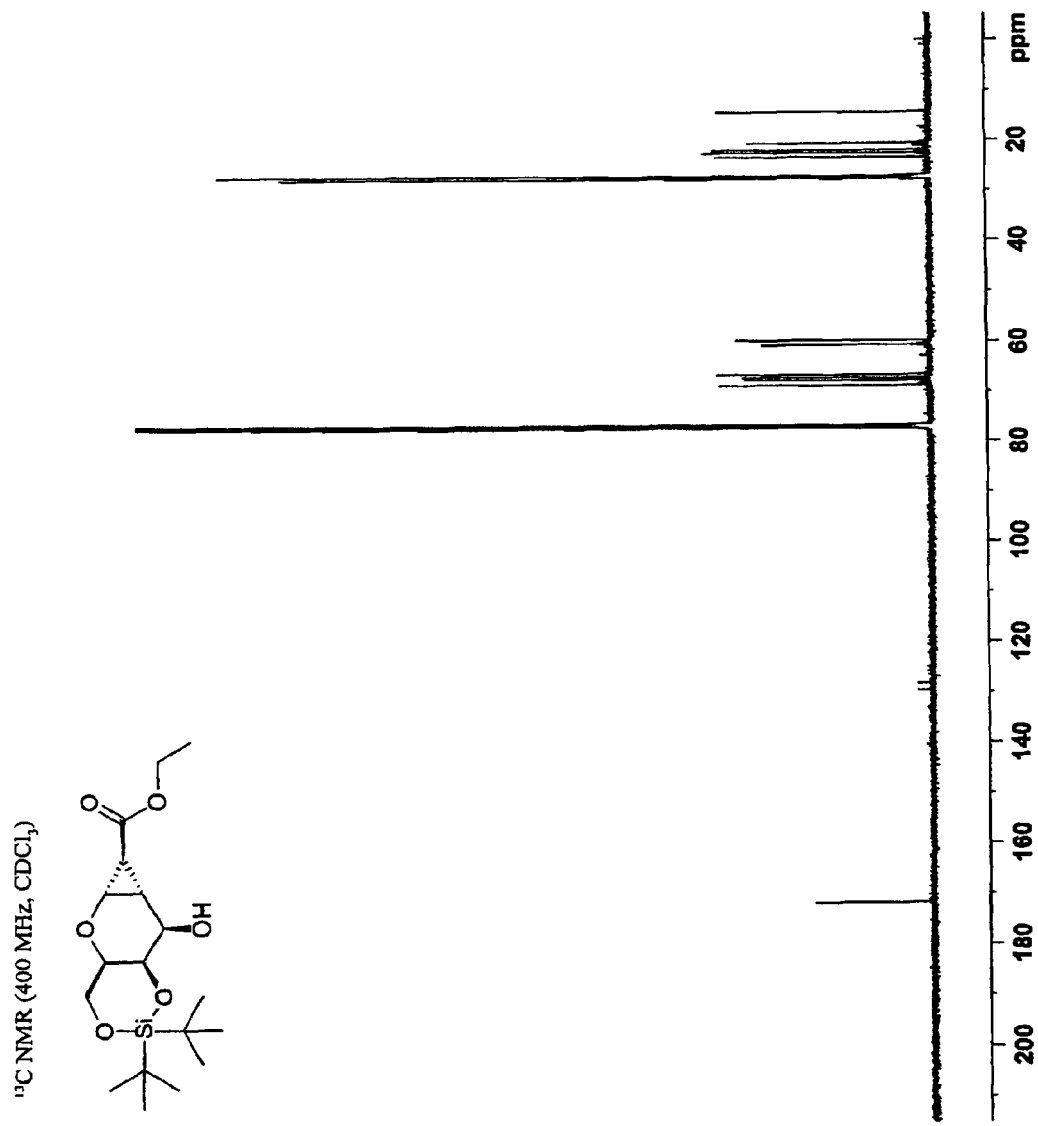

Column chromatography (SiO$_2$, a gradient of pure hexanes to a 3:10 ratio of ethyl acetate in hexanes) on the crude mixture afforded a white solid (0.07 g, 0.19 mmol) 7% yield: mp=114-116° C. $^1$H NMR (400 MHz, CDCl$_3$): is 4.15-4.10 (m, 5H), 4.04 (dd, 1H, J=8.0, 3.0 Hz), 3.80 (apparent dd, 1H, J=10.5, 4.0 Hz), 3.23 (d, 1H, J=11.0 Hz), 3.21 (s, 1H) 1.68 (dd, 1H, J=5.5, 3.0 Hz), 1.61 (apparent t, 1H, J=7.5 Hz) 1.25 (t, 3H, J=7.0 Hz), 1.08 (s, 9H), 1.06 (s, 9H) (FIG. 1). $^{13}$C NMR (400 MHz, CDCl$_3$): δ 171.8, 68.8, 67.7, 67.2, 66.6, 60.4, 59.8, 27.1 (3 C's), 26.9 (3 C's), 23.4, 22.7, 22.4, 20.5, 17.1 (FIG. 2). HRMS (m/z): [M]$^+$ calculated for C$_{18}$H$_{32}$O$_6$Si, 372.1968. found 372.1972 (Δ 0.4 mmu).

(1R,1as,2R,2aR,6aR)-4,4-di-tert-butyl-2-hydroxy-hexahydro-3,5,7-trioxa-4-silacyclopropa[b]naphthalene-1-carboxylic acid (S)-methyl ester (Compound 14b)

Figure 3:
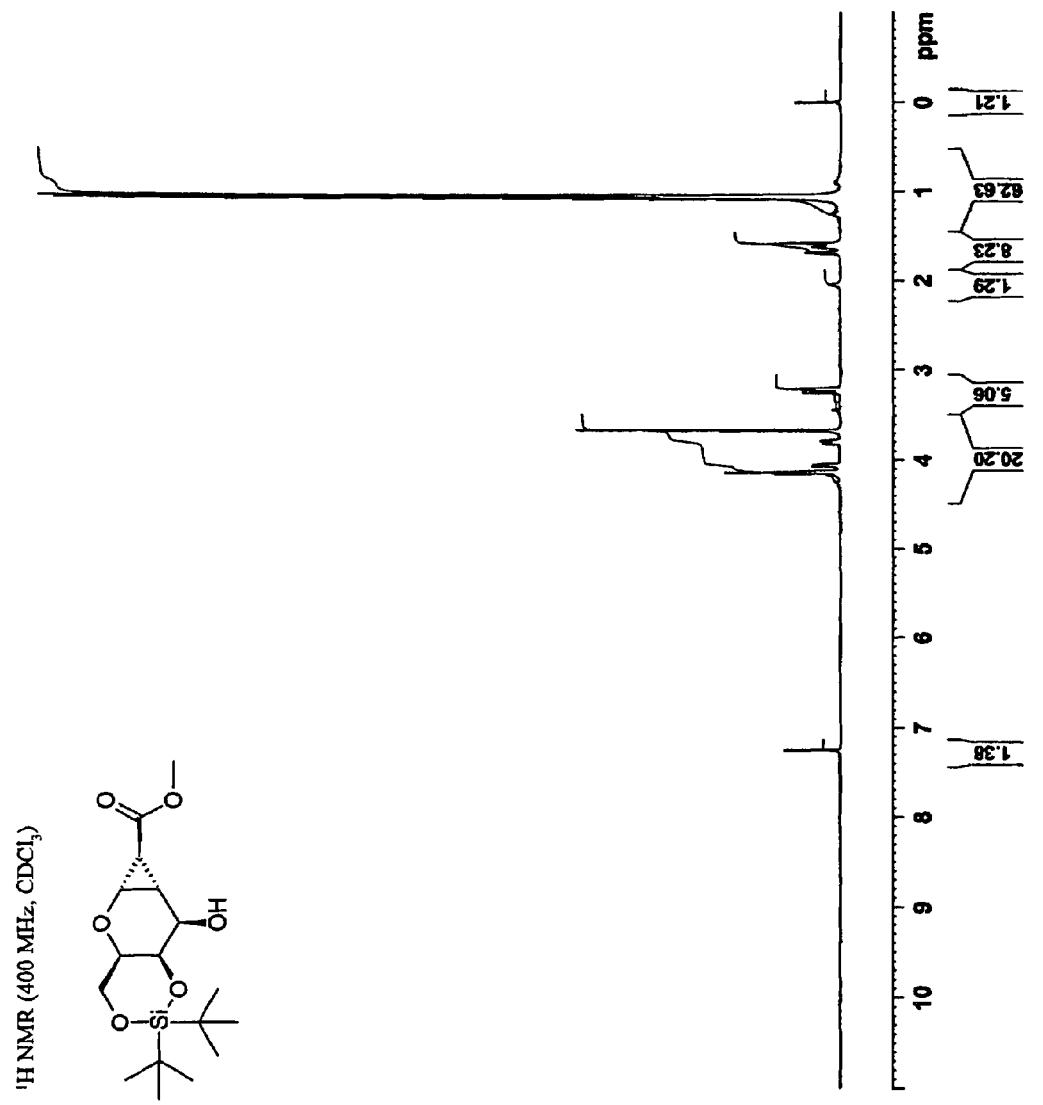
FIG. 3 is a NMR Spectra for Compound 14b.

Column chromatography (SiO$_2$, a gradient of pure hexanes to a 3:10 ratio of ethyl acetate in hexanes) on the crude mixture afforded a colorless glass (0.58 g, 1.6 mmol) 62% yield. $^1$H NMR (400 MHz, CDCl$_3$): δ 4.18-4.13 (m, 3H), 4.06 (dd, 1H, J=8.0, 2.5 Hz), 3.80 (apparent dd, 1H, J=11.0, 3.0 Hz), 3.67 (5, 3H, OMe), 3.24 (d, 1H, J=11.0 HZ), 3.21 (5, 1H), 1.69 (dd, 1H, J=5.5, 3.0 Hz), 1.62 (apparent t, 1H, J=7.5 Hz), 1.08 (s, 9H), 1.06 (s, 9H) (FIG. 3). MS (ESI+): m/z (100%) calculated for C$_{17}$H$_{34}$NO$_6$Si [M+NH]$^+$ 376.5. found 376.2.

Example 3

Preparation of Compound 4

A solution of Compound 3a (0.05 g, 0.13 mmol) in 2 ml of DCM was added dropwise to a solution of Dess-Martin periodinane reagent in (0.11 g, 0.27 mmol) in DCM (4 mL) at 0° C. (freshly distilled over phosphorous pentoxide). The solution was allowed to warm to room temperature slowly and was stirred for an additional 48 hours. The reaction mixture was diluted with 10 ml of diethyl ether, was cooled to 0° C. and quenched with a solution of sodium thiosulfate (0.23 g, 1.3 mmol) in 4 ml of saturated sodium bicarbonate. The resulting heterogeneous mixture was stirred at 0° C. for 10 min. The aqueous and organic layers were separated. The aqueous layer was washed with diethyl ether (2×10 ml), and the combined organics were washed with saturated sodium bicarbonate (1×10 ml) and brine (1×10 ml). The organic layer was dried with Na$_2$SO$_4$, filtered, and concentrated in vacuo. Extractive workup afforded a colorless glass (0.05 g, 0.12 mmol) 93% yield.

Figure 5:
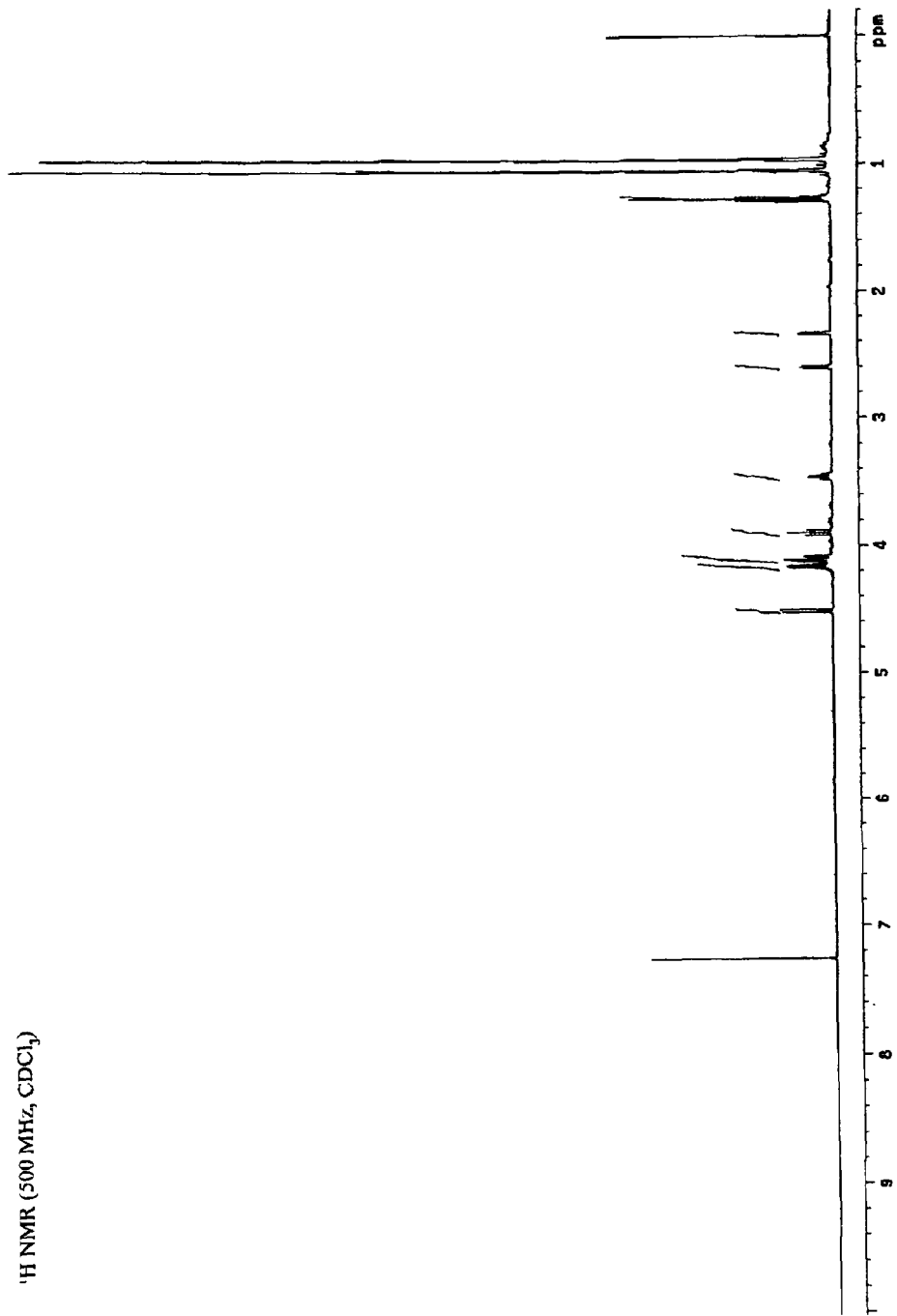
FIGS. 5-6 are NMR spectra for the major component of Compound 4.
Figure 6:
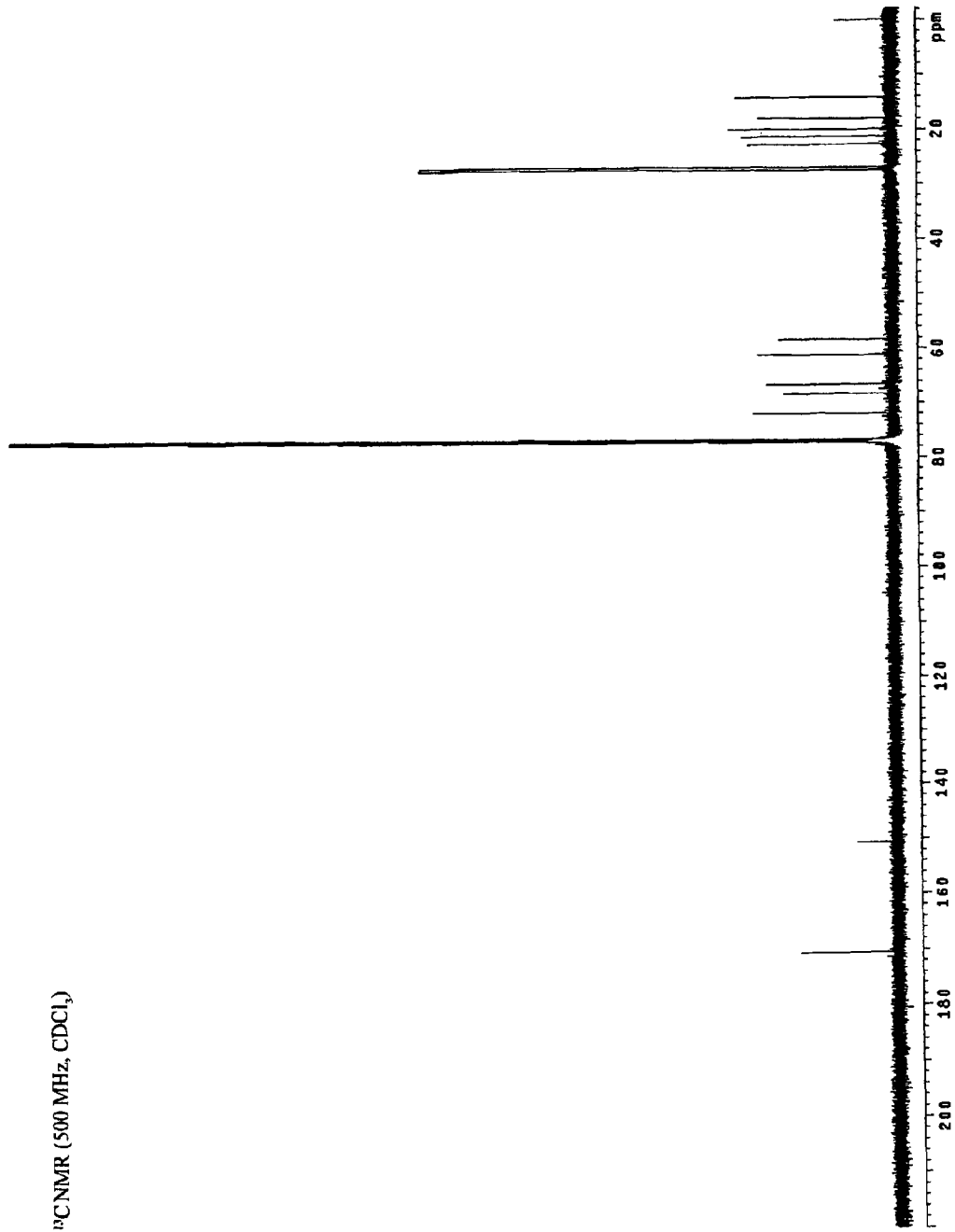
Figure 7:
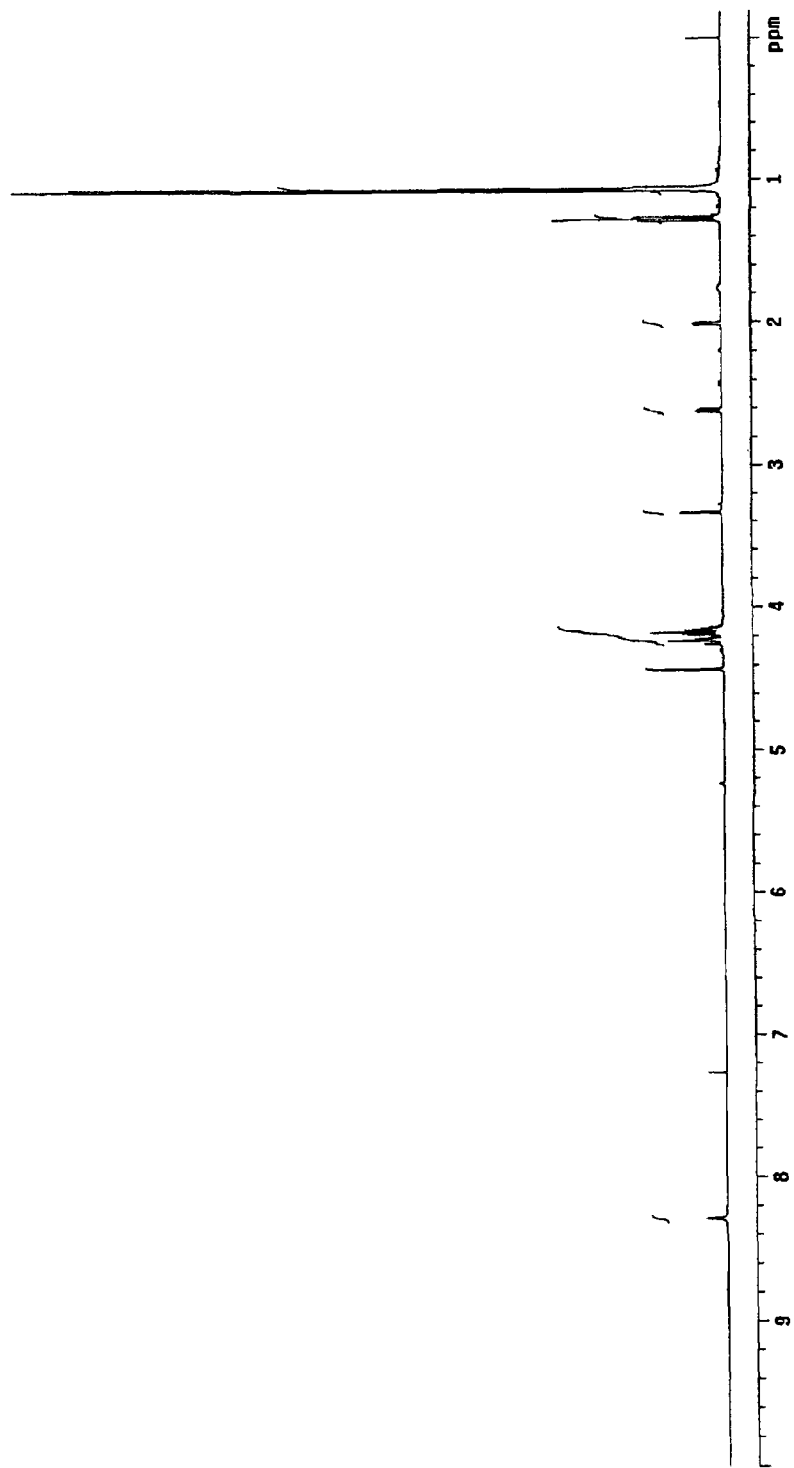
FIGS. 7-8 are NMR spectra for the minor component of Compound 4.
Figure 8:
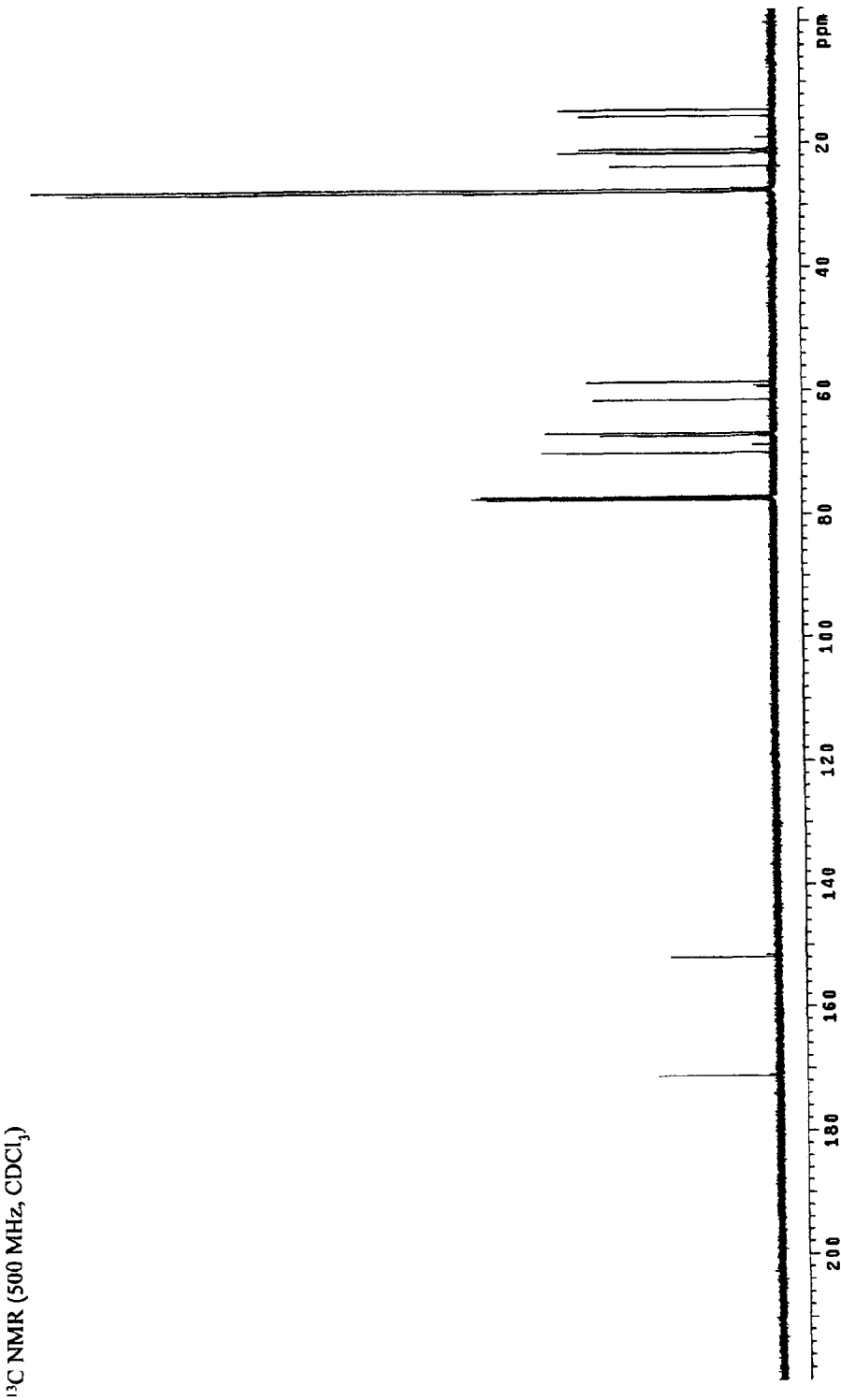

Hydroxylamine hydrochloride (0.17 g, 2.5 mmol) followed by the product of the above reaction (0.80 g, 2.2 mmol) was added to a solution TEA (0.75 mL, 5.4 mmol) in ethanol. The reaction mixture was refluxed for 2 hours and was stirred at 50° C. for an additional 12 hours. The reaction mixture was concentrated in vacuo, and the crude mixture of Z and E isomers was purified by column chromatography (SiO$_2$, a gradient of pure hexanes to a 9:11 ratio of ethyl acetate in hexanes to afford a white solid (Major product 0.60 g, 1.6 mmol) 72% yield: mp=73-77° C. $^1$H NMR (500 MHz, CDCl$_3$): δ 4.52 (d, 1H, J=10.5 Hz), 4.20-4.08 (m, 4H), 3.90 (apparent t, 1H, J=10.0 Hz), 3.46 (ddd, 1H, J=10.0, 10.0, 4.5 Hz), 2.60 (dd, 1H, J=6.5, 5.0 Hz), 2.34 (dd, 1H, J=5.0, 3.0 Hz), 1.28 (t, 3H, J=7.0 Hz), 1.06 (s, 9H, t-butyl), 0.97 (s, 9H, t-butyl) (FIG. 5). $^{13}$C NMR (500 MHz, CDCl$_3$): δ 170.6, 150.7, 72.0, 68.3, 66.6, 61.2, 58.4, 27.4 (3 C's), 26.9 (3 C's), 22.7, 21.4, 20.0, 18.0, 14.2 (FIG. 6). HRMS (m/z): [M]$^+$ calculated for C$_{18}$H$_{31}$NO$_6$Si, 385.1923. found 385.1923 (Δ 0.2 mmu). Further elution afforded a colorless solid (Minor product, 0.20 g, 0.52 mmol) 24% yield: mp=131-137° C.; $^1$H NMR (500 MHz, CDCl$_3$): 8.29 (s, 1H), 4.43 (s, 1H), 4.26-4.14 (m, 5H), 3.34 (s, 1H), 2.62 (dd, 1H, J=7.0, 5.0 Hz), 2.01 (dd, 1H, J=5.0, 2.5 Hz), 1.27 (t, 3H, J=7.0 Hz), 1.07 (s, 9H, t-butyl) 1.06 (s, 9H, t-butyl) (FIG. 7). $^{13}$C NMR (500 MHz, CDCl$_3$): δ 171.0, 151.6, 69.7, 66.9, 66.5, 61.1, 58.2, 27.5 (3 C's), 27.1 (3 C's), 23.4, 21.3, 20.7, 15.2, 14.2 (FIG. 8). HRMS (m/z): [M]$^+$ calculated for C$_{18}$H$_{31}$NO$_6$Si, 385.1921. found 385.1921.

Example 4

General Procedure for the Preparation of Compounds 5, 8a, and 17a (dimethylsulfamoylation)

NaH (a 60% dispersion in mineral oil, 0.18 g, 4.5 mmol) was added to a dry 3-neck flask which was washed with hexanes (3×5 mL) and combined with DCM (10 mL). To this suspension a cyclopropanated carbohydrate was added as a solid or as a solution in DCM (5 mL) (dropwise addition) at 0° C. or room temperature. After 15 minutes at 0° C., dimethylsulfamoyl chloride (0.58 mL, 5.4 mmol) was added dropwise and the reaction was stirred while warming to room temperature for an additional 48 hours. The reaction mixture was quenched with water at 0° C., and diluted with ice cold water (20 mL) and DCM (50 mL). The aqueous layer was removed, and the organic layer was washed with ice cold water (2×20 mL), saturated sodium bicarbonate (1×20 mL), and brine (1×20 mL). The organic layer was dried over Na$_2$SO$_4$, filtered, and concentrated in vacuo.

(1S,1as,2R,2aR,6aR,7aS)-4,4-di-tert-butyl-2-dimethylsulfamoyloxy-hexahydro-3,5,7-trioxa-4-sila-cyclopropa[b]naphthalene-1-carboxylic acid ethyl ester (Compound 5)

Figure 9:
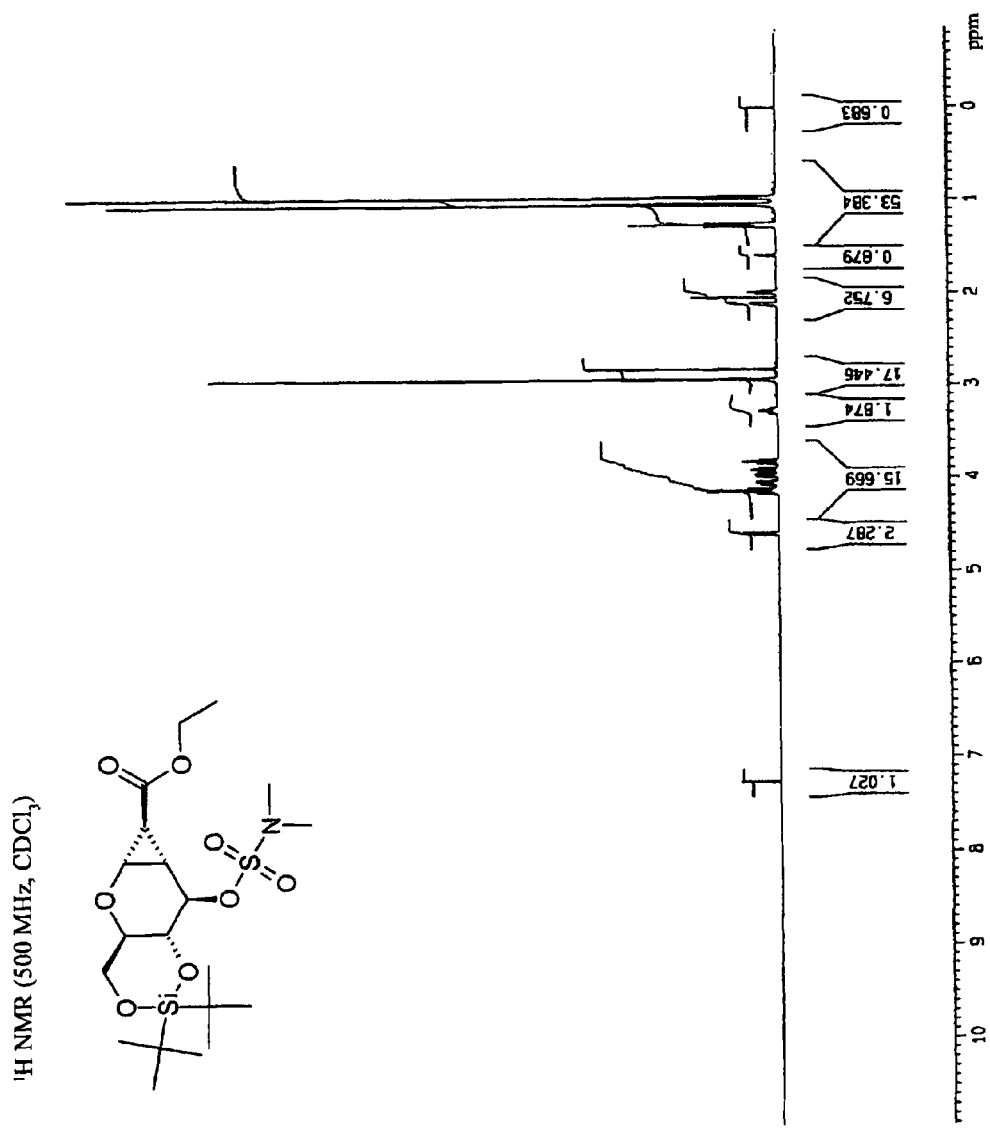
FIGS. 9 and 10 are NMR Spectra for Compound 5.
Figure 10:
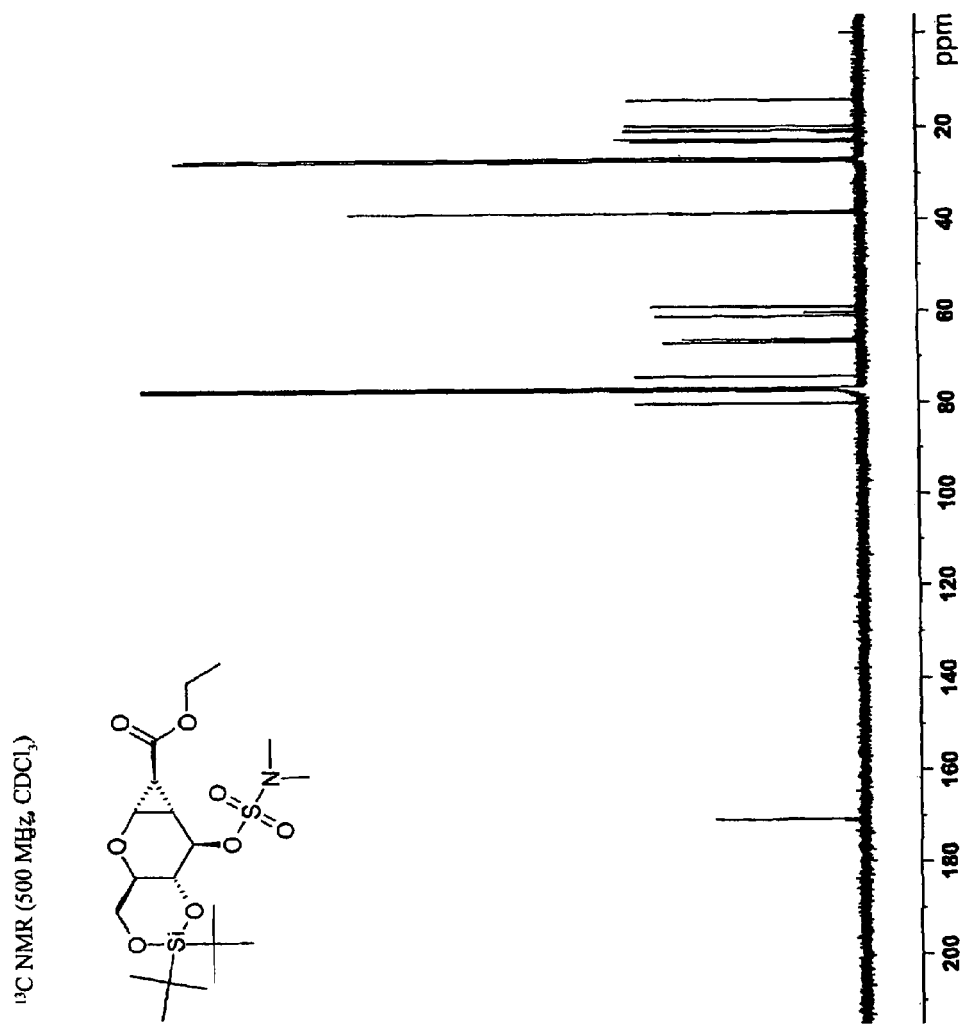

Treatment of Compound 3a (0.35 g, 0.94 mmol) with NaH (0.11 g, 2.8 mmol) and dimethylsulfamoyl chloride (0.27 g, 1.9 mmol) in DCM (20 mL) yielded a crude mixture. Column chromatography (SiO$_2$, a gradient of pure DCM to a 3:97 ratio of ethyl acetate in DCM) on the crude mixture afforded a colorless glass (0.35 g, 0.73 mmol) 78% yield. $^1$H NMR (400 MHz, CDCl$_3$): 04.59 (d, 1H, J=8.0 Hz), 4.14 (q, 2H, J=7.0 Hz), 4.06 (dd, 1H, J=10.5, 5.0 Hz), 3.97 (dd, 1H, J=8.5, 2.5 Hz), 3.91 (apparent t, 1H, J=8.5 Hz), 3.82 (apparent t, 1H, J=10.0 Hz), 3.26 (ddd, 1H, J=10.0, 10.0, 5.0 Hz), 2.93 (5, 6H), 2.11 (dd, 1H, J=6.0, 3.0 Hz), 1.98 (apparent t, 1H, J=6.5 HZ), 1.28-1.24 (m, 3H), 1.04 (s 9H), 0.97 (s, 9H) (FIG. 9). $^{13}$C NMR (400 MHz, CDCl$_3$): δ 170.7, 80.1, 74.2, 66.9, 66.3, 61.1, 59.1, 38.6, 38.1, 27.3 (3 C's), 26.8 (3 C's), 23.1, 22.7, 20.7, 19.8, 14.2 (FIG. 10). HRMS (m/z): [M]$^+$ calculated for C$_{20}$H$_{37}$NO$_8$SSi, 479.2009. found 479.2017 (Δ 0.8 mmu).

Ethyl (4aR,5aS,6aS,7R,7aR)-7-[(dimethlylsulfamoyl)oxy]-2,2-dimethylhexahydro-4H-cyclopropa[5,6]pyrano[3,2-d][1,3]dioxine-6-carboxylate (Compound 8a)

Figure 17:
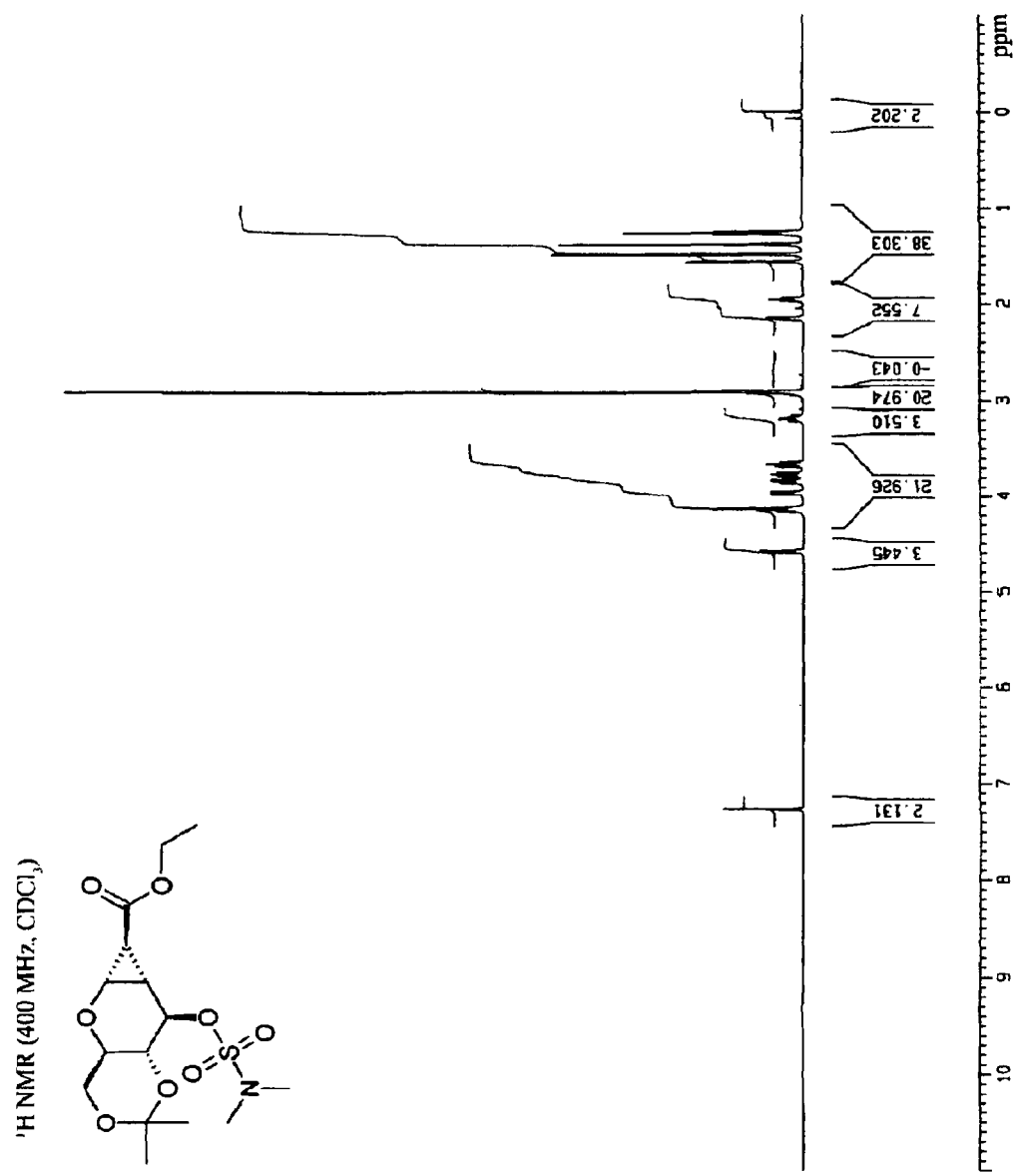
Figure 18:
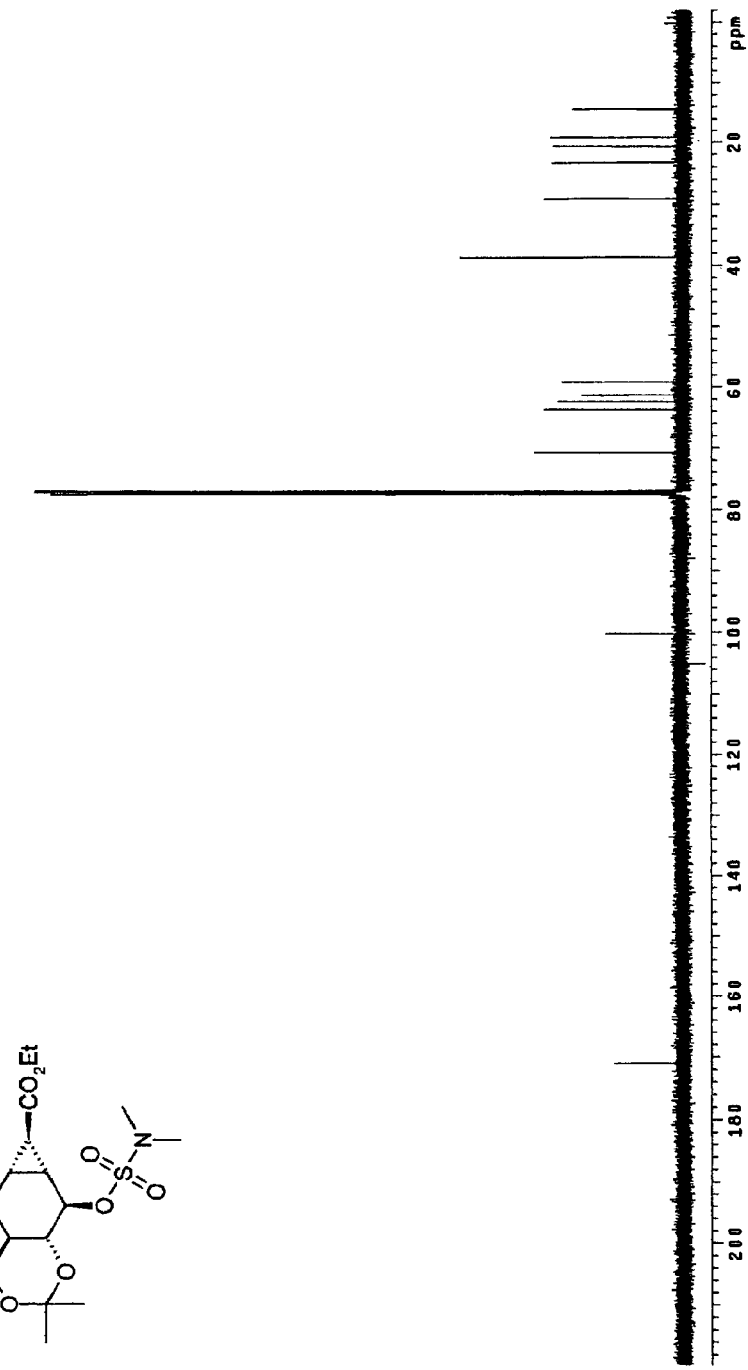

Treatment of Compound 6a (0.49 g, 1.8 mmol) with NaH (0.18 g, 4.5 mmol) and dimethylsulfamoyl chloride (0.76 g, 5.4 mmol) in DCM (30 mL) yielded a crude mixture. Column chromatography (SiO$_2$, a gradient of pure hexanes to a 7:13 ratio of ethyl acetate in hexanes) on the crude mixture afforded a white solid (0.46 g, 1.2 mmol). This material was further purified by preparative TLC (3:7 ratio of ethyl acetate in hexanes) to afford a white solid (0.34 g, 0.9 mmol) 50% yield: mp=120-133° C. (decomposition). $^1$H NMR (500 MHz, CDCl$_3$): δ 4.59 (d, 1H, J=9.0 Hz), 4.14 (q, 2H, J=7.0 Hz), 3.97 (dd, 1H, J=7.5, 2.5 Hz), 3.85 (dd, 1H, J=11.0 Hz, 5.5 Hz), 3.77 (dd, 1H, J=10.5, 9.0 Hz), 3.67 (dd, 1H, J=11.0, 10.0 Hz), 3.18 (ddd, 1H, J=10.0, 10.0, 5.5 Hz), 2.91 (s, 6H), 2.15 (dd, 1H, J=9.0, 3.0 Hz), 1.95 (apparent t, 1H, J=7.0 Hz), 1.48 (s, 3H), 1.38 (s, 3H), 1.26 (t, 3H, J=7.5 Hz) (FIG. 17). $^{13}$C NMR (500 MHz, CDCl$_3$): δ 171.8, 100.0, 76.9, 70.5, 63.5, 62.1, 61.2, 59.0, 38.4 (2 C's), 28.9, 23.1, 20.5, 19.0, 14.2 (FIG. 18). HRMS (m/z): [M+Na]$^+$ calculated for C$_{15}$H$_{25}$NNaO$_8$S, 402.1193. found 402.1200 (Δ 0.7 mmu).

Ethyl (2R,4aR,5aS,6aS,7R,7aR)-7-[(dimethylsulfamoyl)oxy]-2-(4-methoxyphenyl)hexahydro-4H-cyclopropa[5,6]pyrano[3,2-d][1,3]dioxine-6-carboxylate (Compound 17a)

Figure 27:
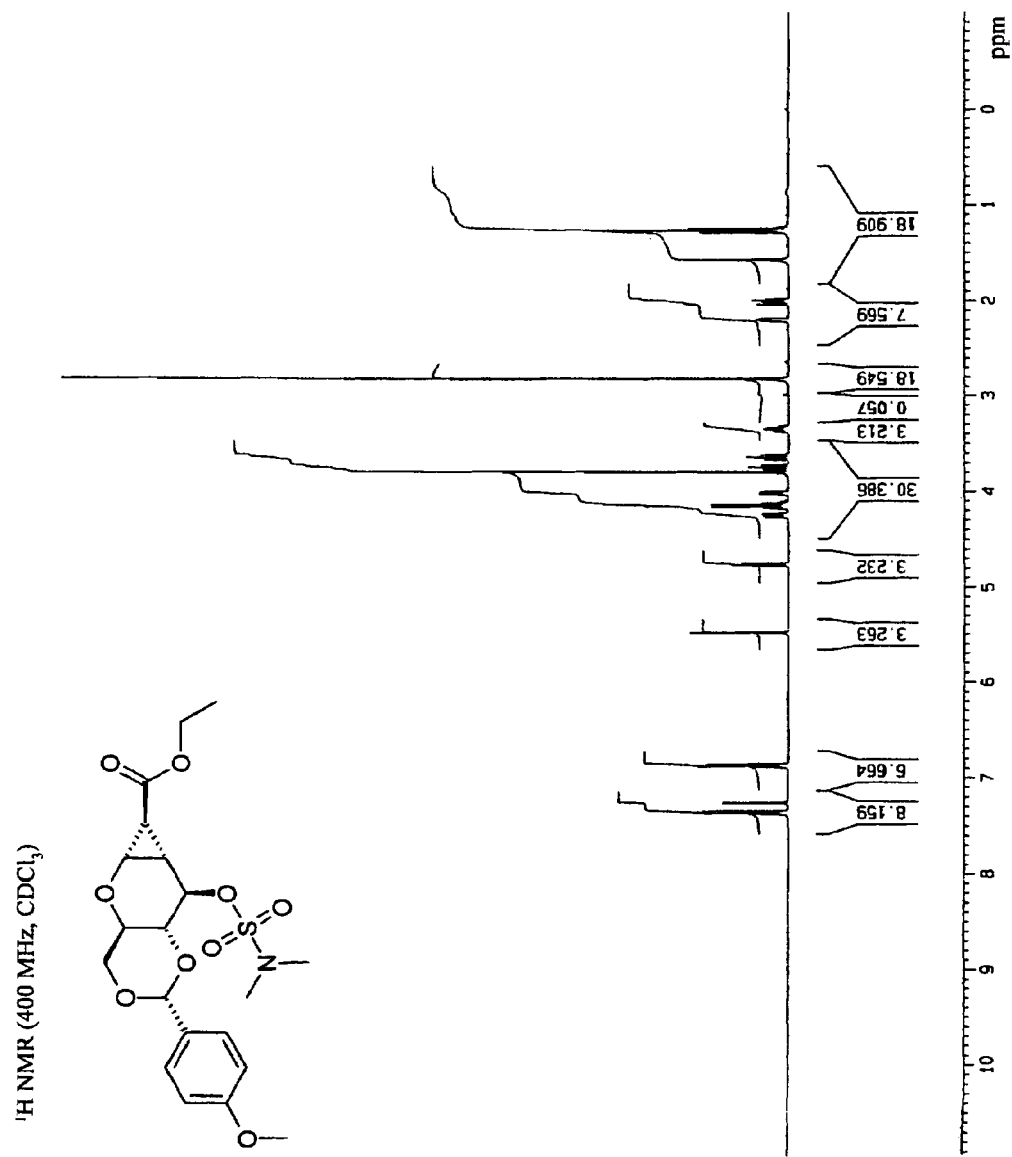

Treatment of Compound 16 (0.20 g, 0.57 mmol) with NaH (0.040 g, 1.7 mmol) and dimethylsulfamoyl chloride (0.20 g, 1.4 mmol) in DCM (15 mL) yielded a crude mixture. Column chromatography (SiO$_2$, a gradient of pure hexanes to a 2:3 ratio of ethyl acetate in hexanes) on the crude mixture afforded a white solid (0.19 g, 0.42 mmol) 73% yield. $^1$H NMR (400 MHz, CDCl$_3$): 0 7.40-7.35 (m, 2H), 6.89-6.86 (m, 2H), 5.48 (s, 1H), 4.76 (d, 1H, J=8.5 Hz), 4.25 (dd, 1H, J=10.5, 5.0 Hz), 4.15 (q, 2H, J=7.0 Hz), 4.02 (dd, 1H, J=7.5, 3.0 Hz), 3.80 (s, 3H), 3.75 (m, 1H), 3.64 (apparent t, 1H, J=10.0 Hz), 3.35 (ddd, 1H, J=10.0, 10.0, 5.0 Hz), 2.82 (s, 6H), 2.20 (dd, 1H, J=6.0, 3.0 Hz), 2.02-2.00 (m, 1H), 1.27 (t, 3H, J=7.0 Hz) (FIG. 27). HRMS (m/z): [M+H]$^+$ calculated for C$_{20}$H$_{28}$NO$_9$S, 458.1479. found 458.1476 (Δ 0.3 mmu).

Example 5

General Procedure for the Preparation of Compounds 6a, 15, and 10

A solution of C3, C4, C6-trihydroxy carbohydrate (1.5 g, 6.5 mmol), 2,2-dimethoxypropane (4.0 mL, 32.3 mmol), and p-toluene sulfonic acid monohydrate (0.43 g, 2.3 mmol) was stirred in DMF (15 mL) at room temperature for 24 to 48 hours. The reaction mixture was extracted with DCM (3×30 mL), water (3×50 mL), and brine (1×50 mL). The combined organics were dried with Na$_2$SO$_4$, filtered, and concentrated in vacuo.

Ethyl (4aR,5aS,6aR,7R,7aS)-7-hydroxy-2,2-dimethylhexahydro-4H-cyclopropa[5,6]pyrano[3,2-d][1,3]dioxine-6-carboxylate (Compound 6a)

Figure 11:
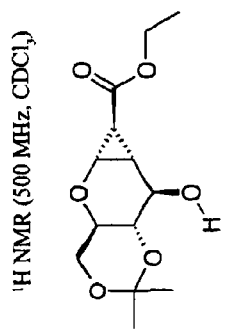
Figure 11:
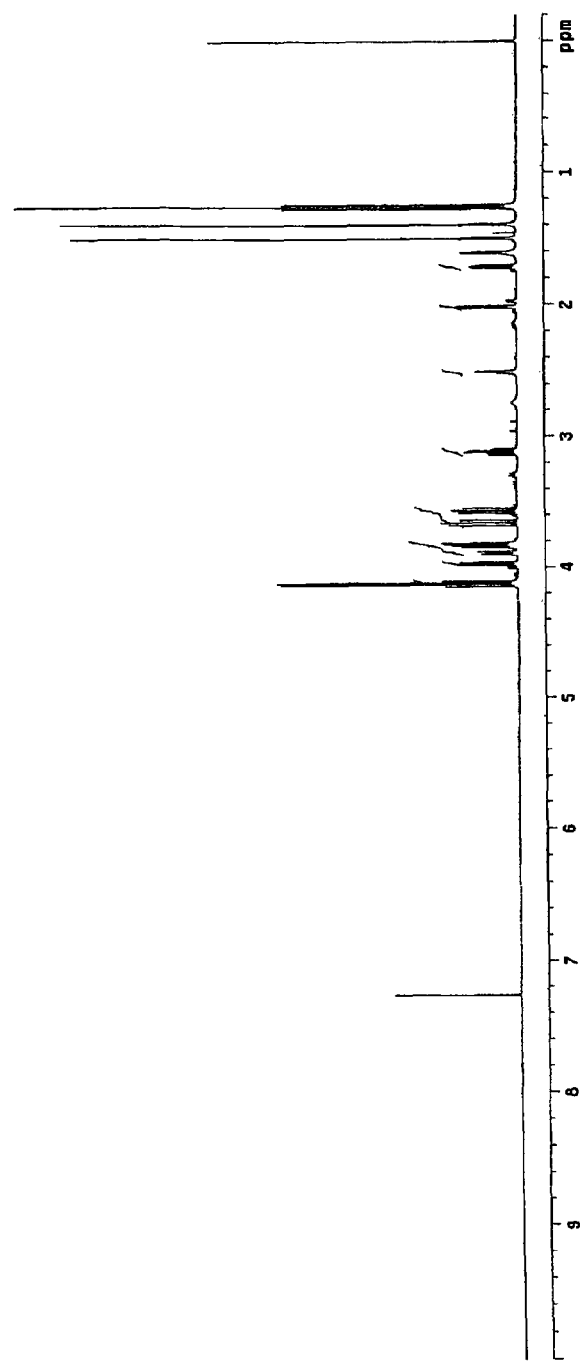
Figure 12:
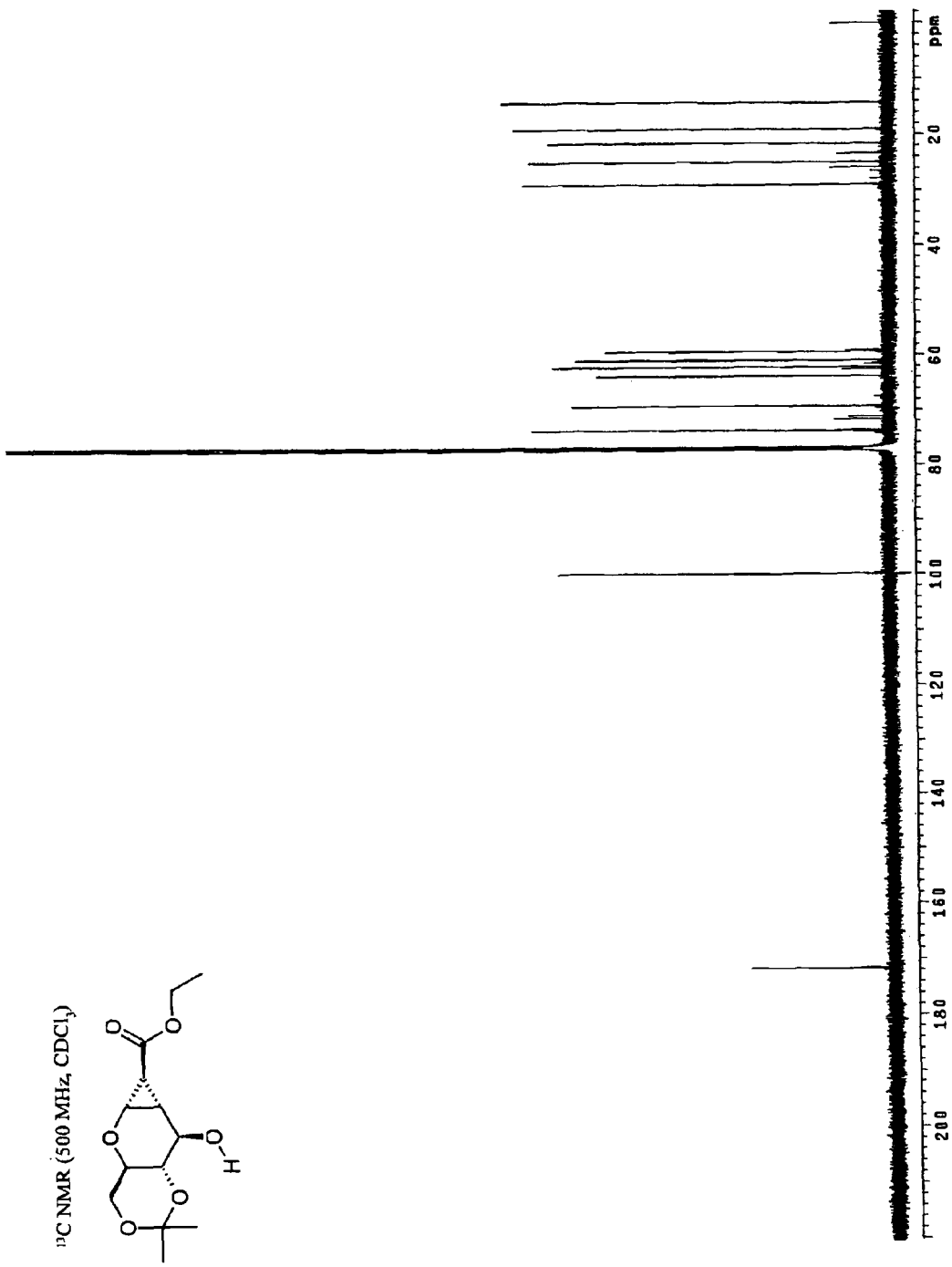

Treatment of Compound 2 (0.98 g, 4.2 mmol) with 2,2-dimethoxypropane (2.6 mL, 21.1 mmol) and p-TsOH H$_2$O (0.0709, 0.37 mmol) in DMF (10 mL) yielded a crude mixture. Extractive workup afforded a white solid (1.1 g, 3.9 mmol) 92% yield: mp=95-101° C. $^1$H NMR (500 MHz, CDCl$_3$): δ 4.12 (q, 2H, J=7.0 Hz), 3.97 (dd, 1H, J=7.5, 2.5 Hz), 3.87 (d, 1H, J=8.0 Hz), 3.82 (dd, 1H, J=11.5, 6.0 Hz), 3.66 (dd, 1H, J=11.0, 10.0 Hz), 3.57 (dd, 1H, J=10.5, 8.5), 3.12 (ddd, 1H, J=10.0, 10.0, 6.0), 2.52 (s, broad, 1H), 2.02 (dd, 1H, J=6.0, 3.0 Hz), 1.73-1.70 (m, 1H), 1.50 (s, 3H, CH$_3$), 1.39 (s, 3H, CH$_3$), 1.25 (t, 3H, J=7.5 Hz) (FIG. 11). $^{13}$C NMR (500 MHz, CDCl$_3$): δ 171.6, 99.9, 73.7, 69.3, 63.8, 62.1, 60.9, 59.3, 29.0, 24.9, 21.6, 19.0, 14.2 (FIG. 12). HRMS (m/z): [M+Na]$^+$ calculated for C$_{13}$H$_{20}$NaO$_6$, 295.1152. found 295.1150 (Δ 0.2 mmu).

Ethyl (3aR,4R,5aS,6aS,6bR)-4-(hydroxymethyl)-2,2-dimethylhexahydrocyclopropa[b][1,3]dioxolo[4,5-d]pyran-6-carboxylate (Compound 15)

Figure 15:
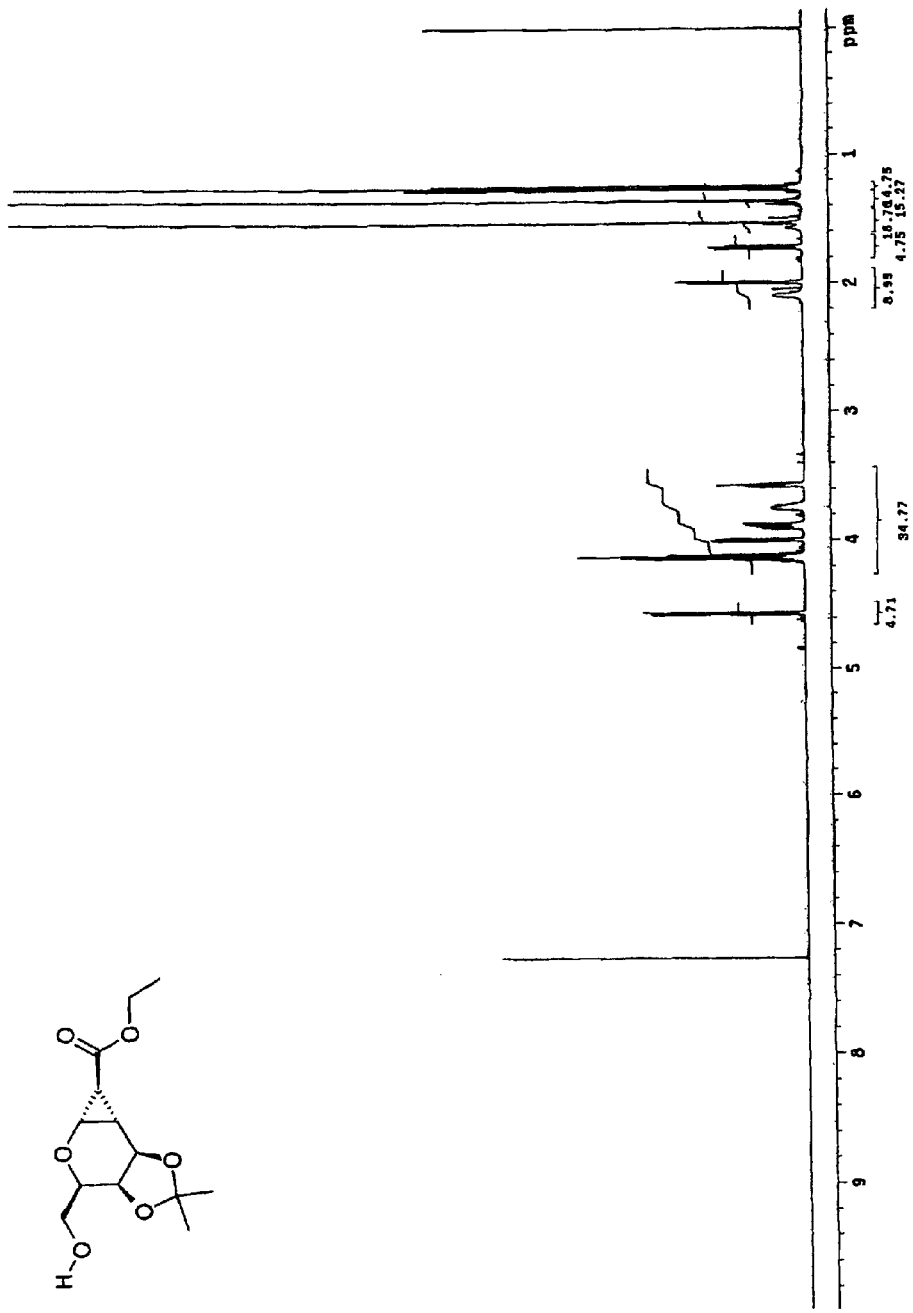
FIGS. 15 and 16 are NMR Spectra for Compound 15.
Figure 16:
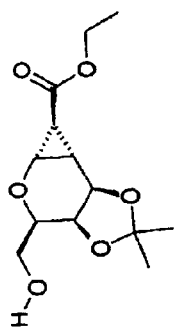
Figure 16:
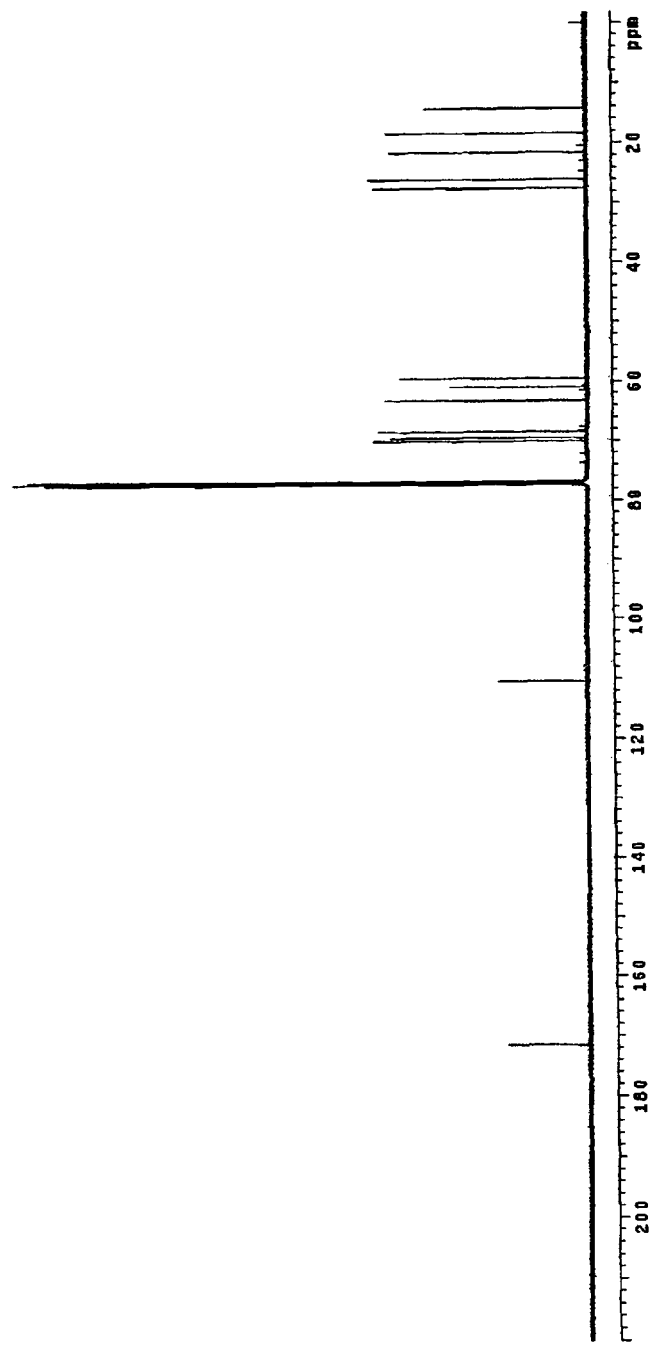

Treatment of Compound 13 (1.5 g, 6.5 mmol) with 2,2-dimethoxypropane (4.0 mL, 32.3 mmol) and p-TsOH H$_2$O (0.43 g, 2.3 mmol) in DMF (15 mL) yielded a crude mixture. Column chromatography (SiO$_2$, a gradient of pure hexanes to pure ethyl acetate) on the crude mixture afforded a white solid (0.54 g, 2.0 mmol) which was further purified by crystallization in diethyl ether (the resulting gel was pressed to remove solvent) and preparative TLC (1:9 ratio of ethanol in hexanes) to afford a white solid (0.19 g, 0.70 mmol) 10% yield. $^1$H NMR (500 MHz, CDCl$_3$): δ 4.57 (d, 1H, J=6.5 Hz), 4.16-4.12 (m, 3H), 4.00 (dd, 1H, J=6.0, 1.5 Hz), 3.90 (dd, 1H, J=12.0, 7.0 HZ), 3.75 (dd, 1H, J=11.5, 4.5 Hz), 3.59-3.56 (m, 1H), 2.06 (s, broad, 1H), 2.00 (dd, 1H, J=6.0, 3.0 Hz), 1.75-1.72 (m, 1H), 1.54 (s, 3H), 1.37 (s, 3H), 1.27 (t, 3H, J=7.5 Hz) (FIG. 15). $^{13}$C NMR (500 MHz, CDCl$_3$): δ 171.5, 110.3, 70.0, 69.5, 68.4, 63.2, 60.9, 59.4, 27.4, 26.0, 21.5, 18.3, 14.2 (FIG. 16). HRMS (m/z): [M]$^+$ calculated for C$_{13}$H$_{20}$O$_6$, 272.1260. found 272.1260.

Methyl (4aR,5aS,6aR,7R,7aS)-7-hydroxy-2,2-dimethylhexahydro-4H-cyclopropa[5,6]pyrano[3,2-d][1,3]dioxine-6-carboxylate (Compound 10)

Figure 21:
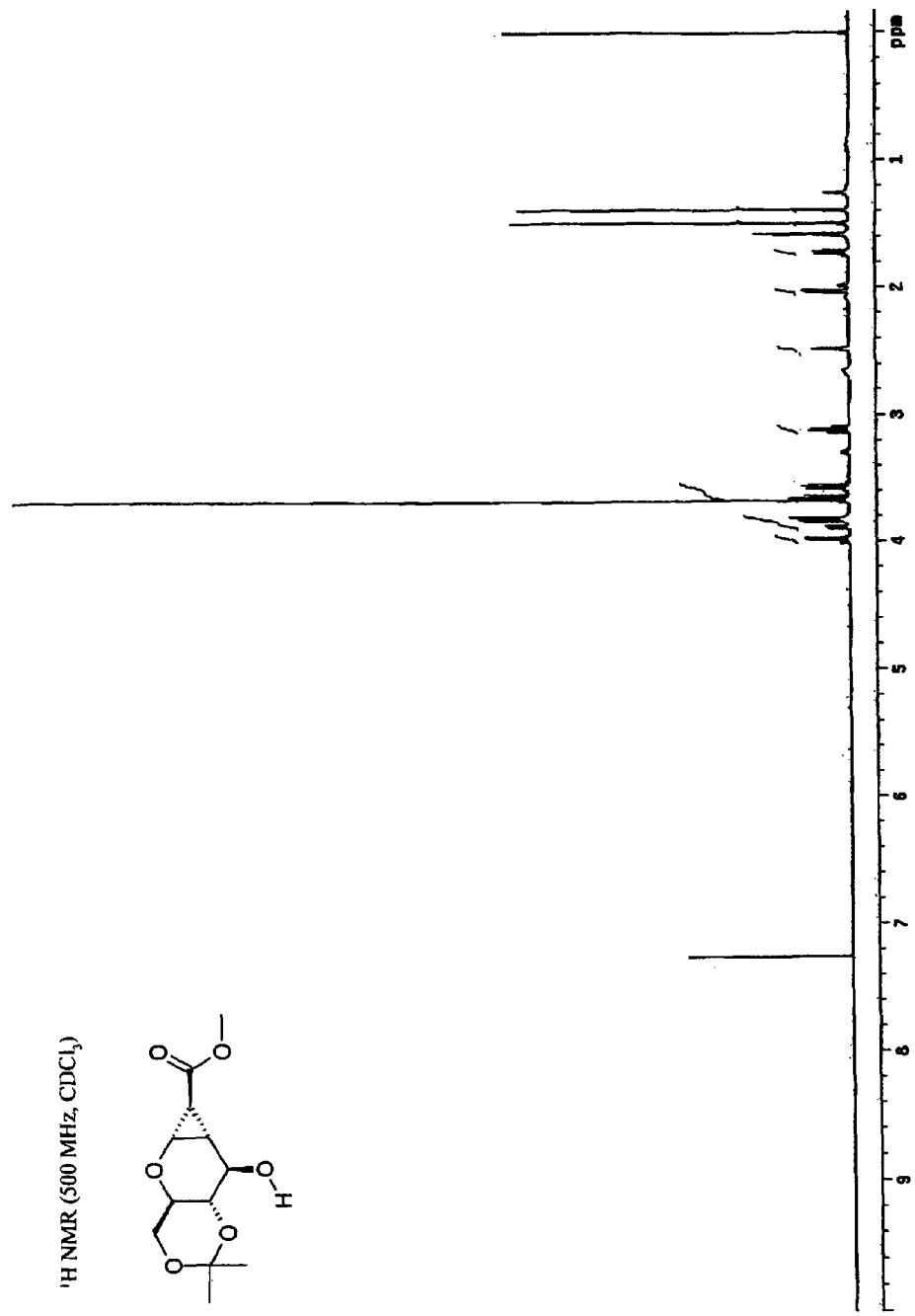
FIGS. 21 and 22 are NMR Spectra for Compound 10.
Figure 22:
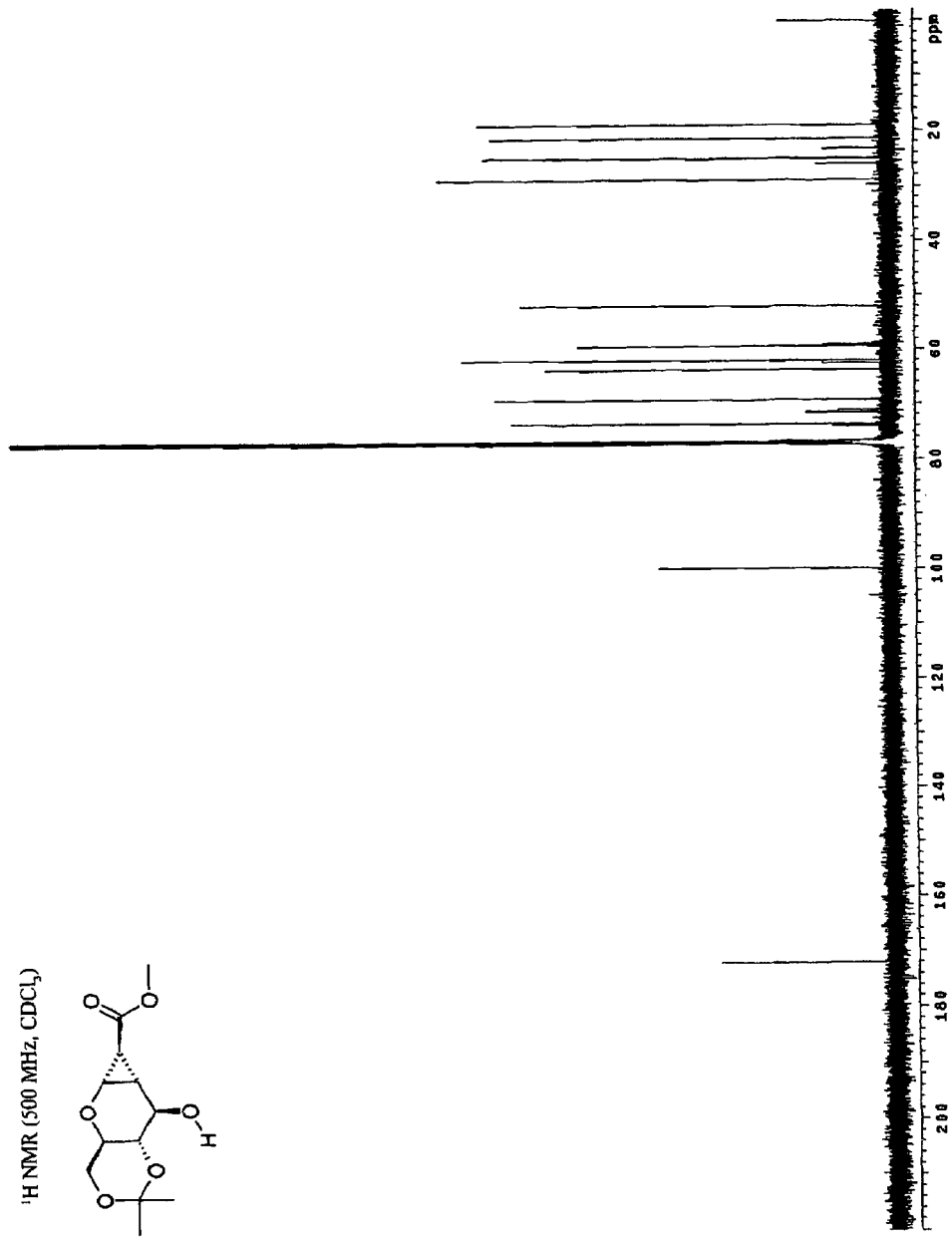

Treatment of Compound 2 (1.5 g, 6.5 mmol) with sodium methoxide (0.70 g, 13.0 mmol) in methanol (20 mL) afforded a crude mixture that was concentrated in vacuo. Column chromatography of the crude (SiO$_2$, a gradient of chloroform to 15:85 methanol in chloroform) afforded a colorless glass (0.33 g, 1.5 mmol). Treatment of this glass with 2,2-dimethoxypropane (0.92 mL, 7.5 mmol), TsOH H$_2$O (0.11 g, 0.53 mmol) in DMF (3 mL) yielded a crude mixture. Extractive workup afforded a white solid (0.30 g, 1.2 mmol) 18% yield over two steps. $^1$H NMR (500 MHz, CDCl$_3$): δ 3.97 (dd, 1H, J=8.0, 3.0 Hz), 3.88 (dd, 1H, J=8.5, 2.5 Hz), 3.83 (dd, 1H J=11.5, 6.0 Hz), 3.68 (s, 3H), 3.65 (apparent d, 1H, J=10.0 Hz), 3.57 (dd, 1H, J=10.5, 8.5 Hz), 3.11 (ddd, 1H, J=10.0, 10.0, 6.0 Hz), 2.48-2.47 (m, broad, 1H) 2.03 (dd, 1H, J=6.0 Hz, 3.0 Hz), 1.74-1.71 (m, 1H), 1.49 (s, 3H), 1.39 (s, 3H) (FIG. 21). $^{13}$C NMR (500 MHz, CDCl$_3$): δ 172.1, 99.9, 73.7, 69.3, 63.8, 62.1, 59.4, 52.0, 29.0, 25.0, 21.4, 19.0 (FIG. 22). HRMS (m/z): [M]$^+$ calculated for C$_{12}$H$_{18}$O$_6$, 258.1103. found [M+Na]$^+$ 281.0997.

Example 6

Preparation of ethyl (4aR,5aS,6aR,7aS)-7-(hydroxyimino)-2,2-dimethylhexahydro-4H-cyclopropa[5,6]pyrano[3,2-d][1,3]dioxine-6-carboxylate (Compound 7: E or Z)

A solution of Compound 6a (0.30 g, 1.1 mmol) in 2 ml of DCM was added dropwise to a solution of Dess-Martin periodinane reagent in 1.1 g, 2.6 mmol) in DCM (20 mL) at 0° C. (freshly distilled over phosphorous pentoxide). The solution was allowed to warm to room temperature slowly and was stirred for an additional 48 hours. The reaction mixture was diluted with 10 ml of diethyl ether, was cooled to 0° C. and quenched with a solution of sodium thiosulfate (0.23 g, 1.3 mmol) in 4 ml of saturated sodium bicarbonate. The resulting heterogeneous mixture was stirred at 0° C. for 10 min. The aqueous and organic layers were separated. The aqueous layer was washed with diethyl ether (2×10 ml), and the combined organics were washed with saturated sodium bicarbonate (1×10 ml) and brine (1×10 ml). The organic layer was dried with Na$_2$SO$_4$, filtered, and concentrated in vacuo. Extractive workup afforded a white solid (0.23 g, 0.86 mmol) 80% yield.

Figure 13:
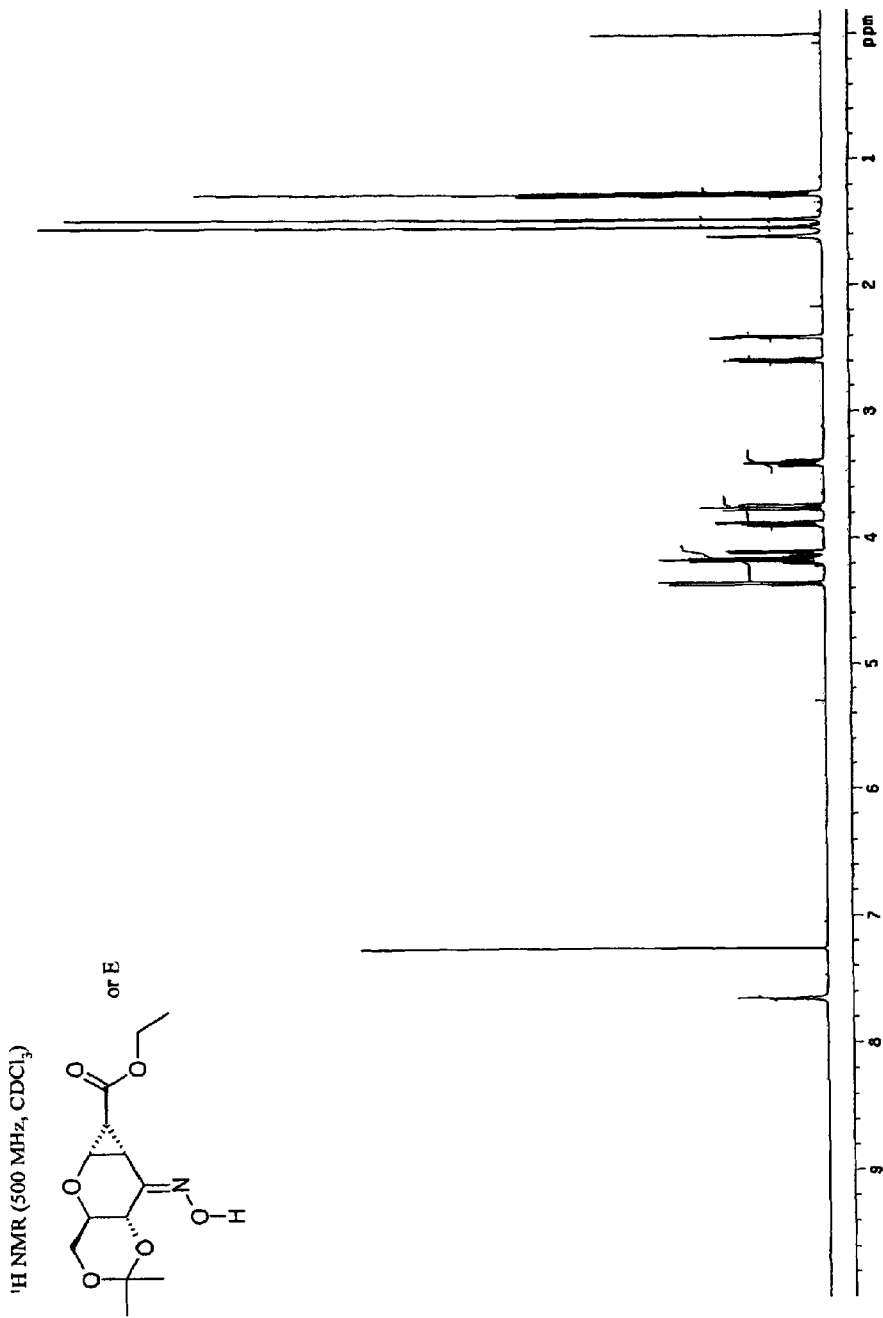
FIGS. 13 and 14 are NMR Spectra for Compound 7.
Figure 14:
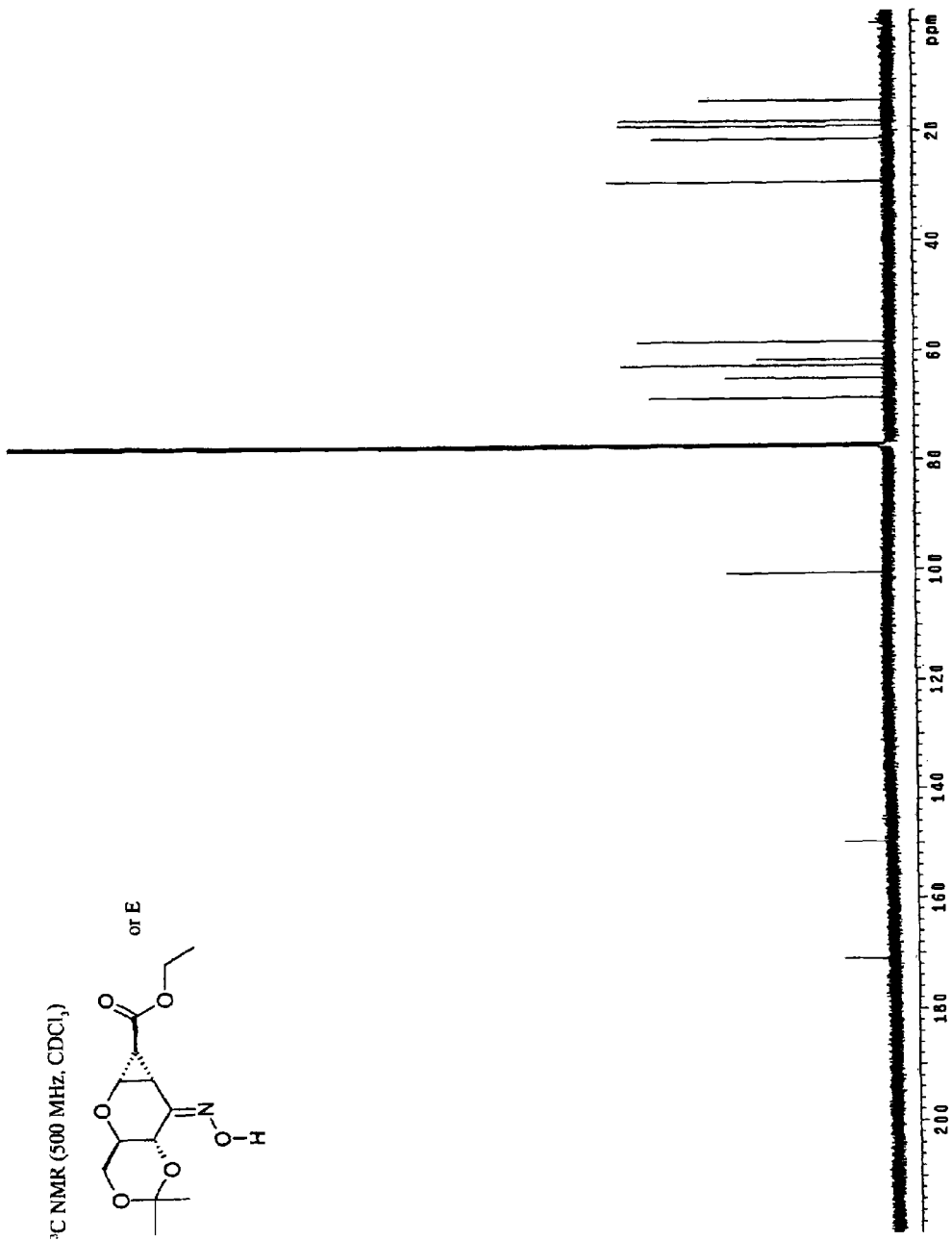

To a solution of TEA (0.24 mL, 1.7 mmol) in ethanol was added hydroxylamine hydrochloride (0.07 g, 1.0 mmol) followed by the product of the above reaction (0.23 g, 0.86 mmol). The reaction mixture was heated at 50° C. for 2 hours, cooled to room temperature, and concentrated in vacuo. The crude product was dissolved in DCM (30 mL) and washed with H$_2$O (2×20 mL) and brine (1×20 mL). The organic layer was dried over Na$_2$SO$_4$, filtered, and concentrated in vacuo. Column chromatography (SiO$_2$, a gradient of pure chloroform to a 1:19 ratio of ethanol in chloroform) on the crude mixture afforded a white solid (0.17 g, 0.6 mmol) 60% yield: mp=210-213° C. $^1$H NMR (500 MHz, CDCl$_3$): δ 7.66 (s, broad, 1H), 4.36 (d, 1H, J=10.5 Hz), 4.21-4.14 (m, 2H), 4.11 (dd, 1H, J=6.5, 3.0 Hz), 3.89 (dd, 1H, J=11, 5.5 HZ), 3.76 (apparent t, 1H, 9.5 Hz), 3.41 (ddd, 1H, J=10.0, 10.0, 5.5 Hz), 2.61-2.58 (m, 1H), 2.41 (dd, 1H, J=5.0, 3.0 Hz), 1.54 (s, 3H, CH$_3$), 1.47 (s, 3H, CH$_3$), 1.26 (t, 3H, J=7.0 Hz) (FIG. 13). $^{13}$C NMR (500 MHz, CDCl$_3$): δ 170.7, 149.5, 100.4, 68.4, 64.8, 62.4, 61.3, 58.1, 28.9, 21.1, 18.8, 17.8, 14.2 (FIG. 14). HRMS (m/z): [M+H]$^+$ calculated for C$_{13}$H$_{20}$NO$_6$, 286.1285. found 286.1287 (Δ 0.2 mmu).

Example 7

Preparation of ethyl (4aR,5aS,6aS,7R,7aR)-2,2-dimethyl-7-(sulfamoyloxy)hexahydro-4H-cyclopropa[5,6]pyrano[3,2-d][1,3]dioxine-6-carboxylate (Compound 8b)

Figure 19:
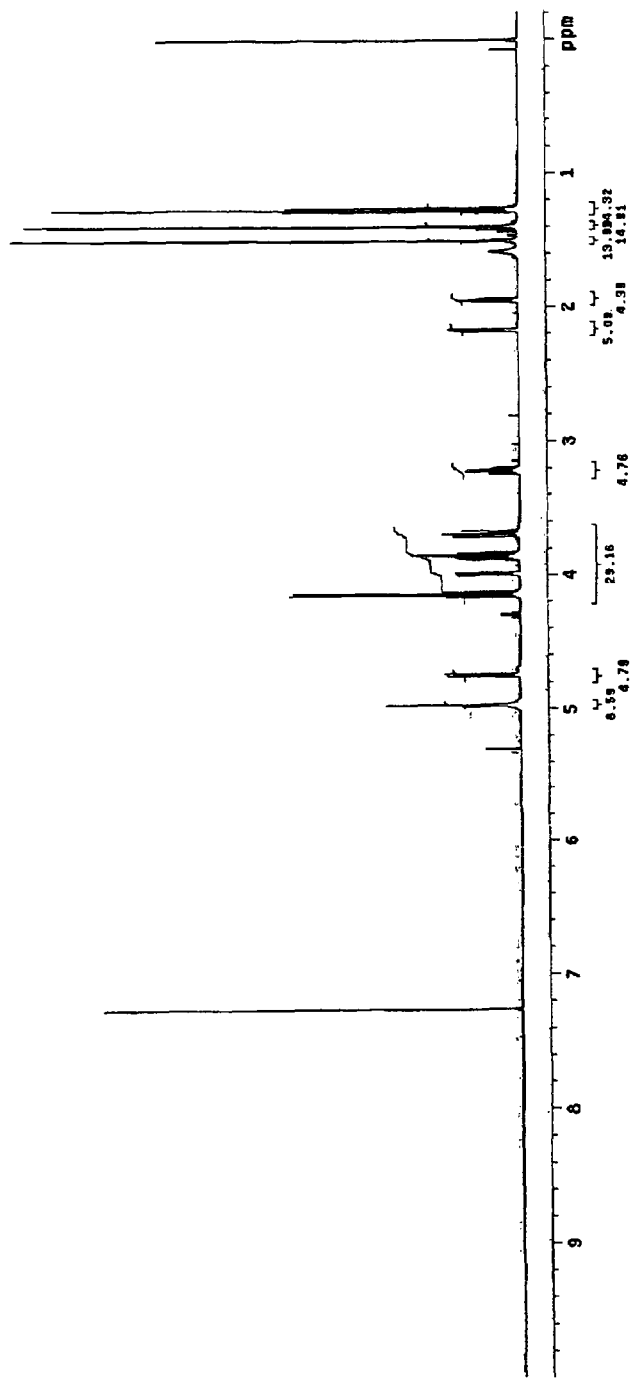
FIGS. 19 and 20 are NMR Spectra for Compound 8b.
Figure 19:
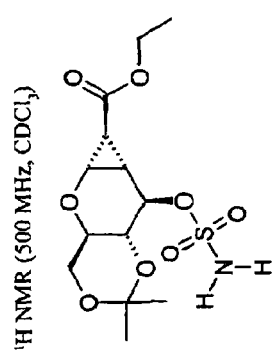
Figure 20:
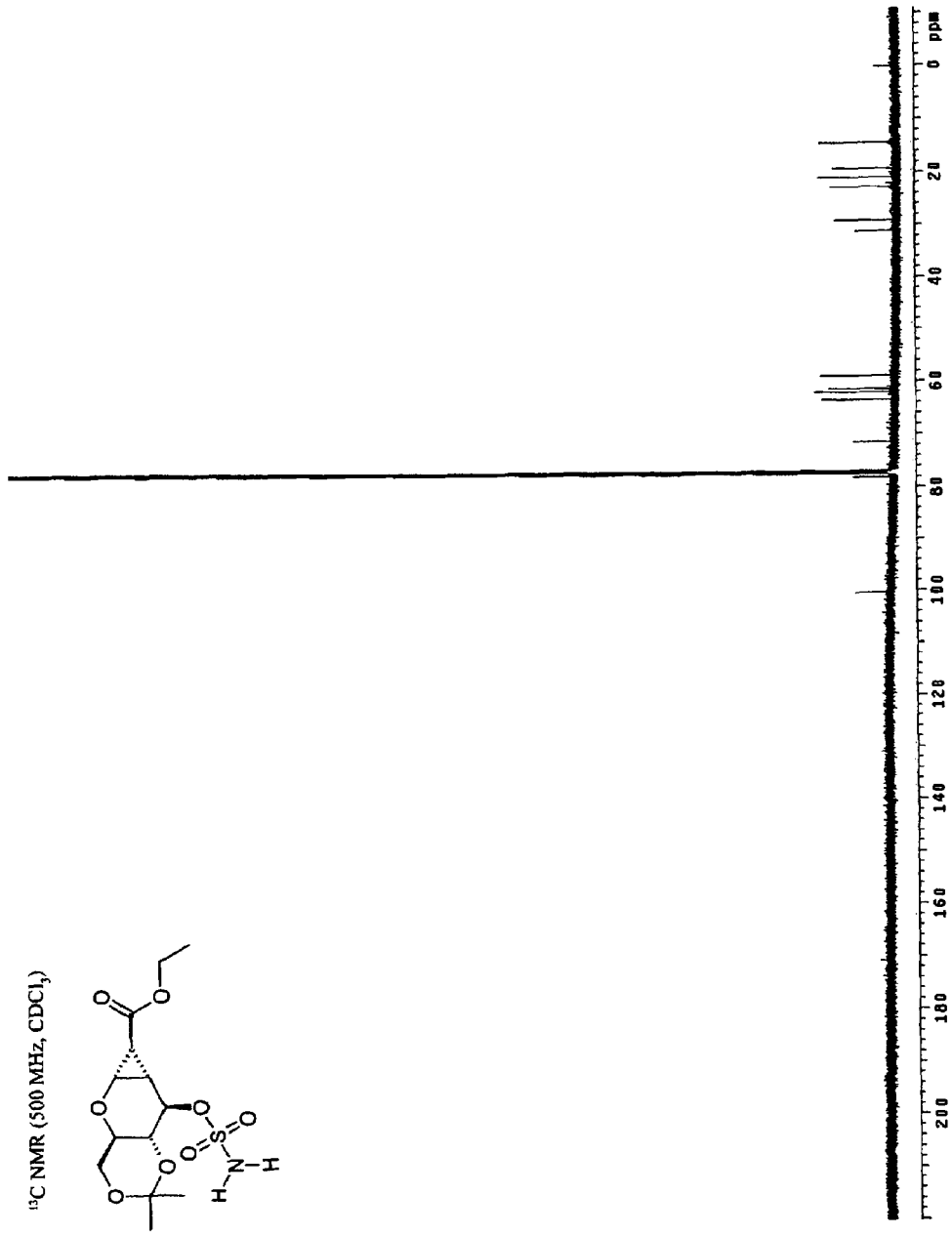

Compound 6a (0.28 g, 1.0 mmol) was added to a dry 3-neck flask containing NaH (60% dispersion in mineral oil, 0.12 g, 3.1 mmol) in DMF (10 mL) at 0° C. After 30 min at 0° C., sulfamoyl chloride (0.36 g, 3.1 mmol) was added in portions, and the reaction was stirred for an additional 1 hour at 0° C. The reaction mixture was quenched with H$_2$O at 0° C. and diluted with ice cold H$_2$O (20 mL) and dichloromethane (50 mL). The aqueous layer was removed, and the organic layer was washed with ice cold water (2×20 mL) and brine (1×20 mL). The organic layer was dried over Na$_2$SO$_4$, filtered, and concentrated in vacuo. Column chromatography (SiO$_2$, a gradient of pure hexanes to a 2:3 ratio of ethyl acetate in hexanes) followed by preparative TLC (SiO$_2$, 7:13 ratio of ethyl acetate in hexanes) on the crude mixture afforded a yellow glass (0.28 g, 0.80 mmol) 77% yield. $^1$H NMR (500 MHz, CDCl$_3$): δ 4.98 (s, 2H), 4.75 (d, 1H, J=8.5 Hz), 4.15 (q, 2H, J=7.5 Hz), 3.99 (dd, 1H, J=8.0, 3.0 Hz), 3.88-3.82 (m, 2H), 3.69 (dd, 1H, J=11.0, 10.0 Hz), 3.22 (ddd, 1H, J=10.0, 10.0, 5.5 Hz), 2.18 (dd, 1H, J=5.0, 3.0 Hz), 1.96-1.94 (m, 1H), 1.50 (s, 3H), 1.40 (s, 3H) 1.27 (t, 3H, J=7.5 Hz) (FIG. 19). $^{13}$C NMR (500 MHz, CDCl$_3$): δ 100.2, 77.9, 71.2, 63.3, 61.9, 61.3, 58.8, 31.0, 29.0, 22.6, 20.8, 19.2, 14.2 (FIG. 20). HRMS (m/z): [M+H]$^+$ calculated for C$_{13}$H$_{22}$NO$_8$S, 352.1061. found 352.1061. Anal. calculated for C$_{13}$H$_{21}$NO$_8$S: C, 44.44; H, 6.02. Found C, 44.54; H, 5.80.

Example 8

General Procedure for the Preparation of Compounds 9 and 18

A solution of C3 hydroxy carbohydrate (1.1 g, 3.7 mmol) in DMF (5 mL) was added to a dry 3-neck flask containing NaH (60% dispersion in mineral oil, washed 3×5 mL hexanes, 0.22 g, 5.5 mmol) in DMF (5 mL) at 0° C. After 30 min at 0° C., methyl iodide (0.35 μL, 5.5 mmol) was added dropwise, and the reaction was stirred for an additional 2 hours at 0° C. (Compound 18) or allowed to warm to room temperature and stirred for 16 h (Compound 9). The reaction mixture was quenched with H$_2$O at 0° C. and diluted with ice cold H$_2$O (20 mL) and DCM (120 mL). The organic layer was washed with water (3×30 mL) and brine (1×20 mL), and it was dried with Na$_2$SO$_4$, filtered, and concentrated in vacuo.

Ethyl (4aR,5aS,6aS,7R,7aS)-7-methoxy-2.2-dimethylhexahydro-4H-cyclopropa[5,6]pyrano[3,2-d][1,3]dioxine-6-carboxylate (Compound 9)

Figure 23:
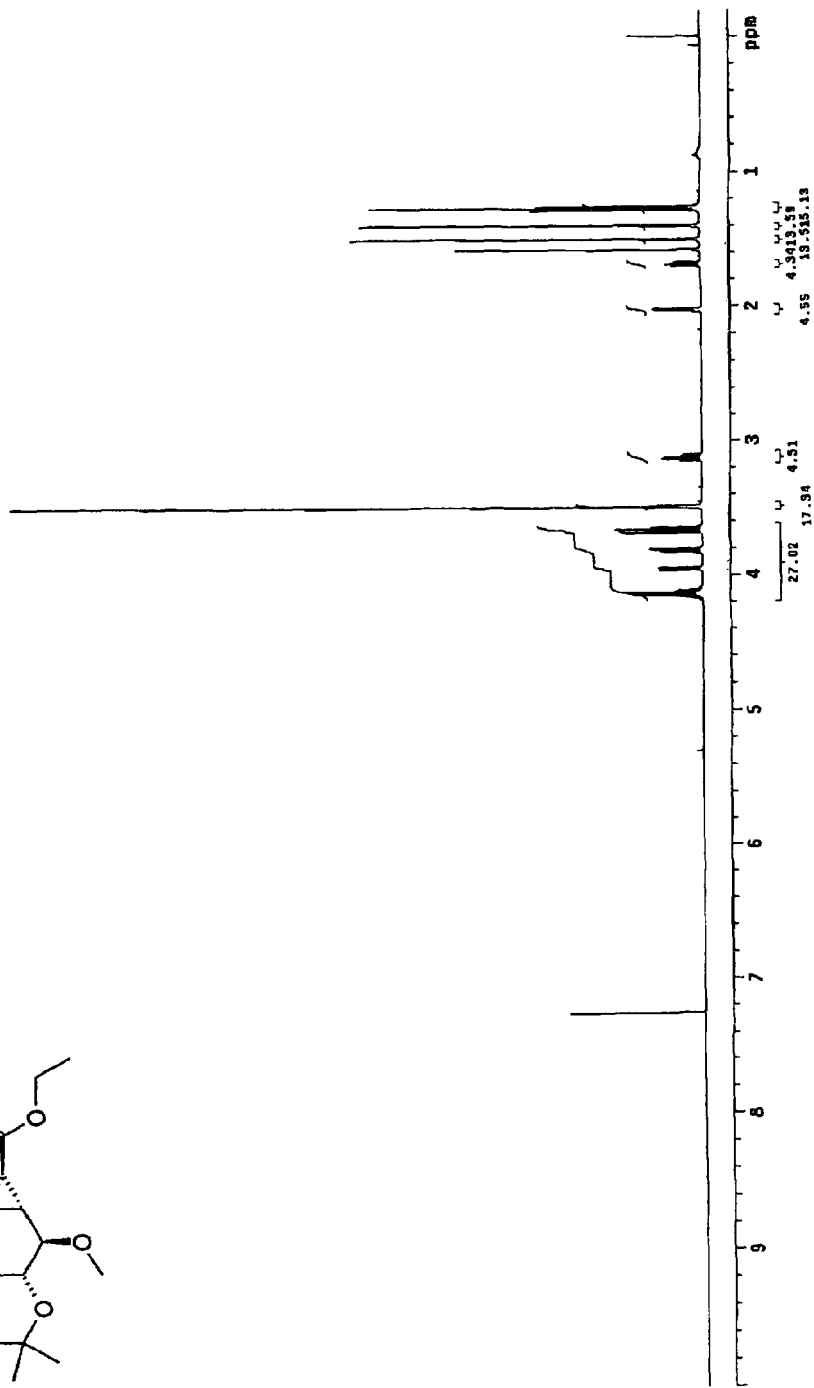
FIGS. 23 and 24 are NMR Spectra for Compound 9.
Figure 23:
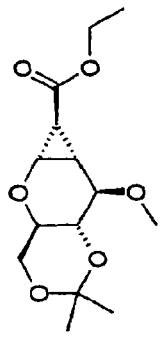
Figure 24:
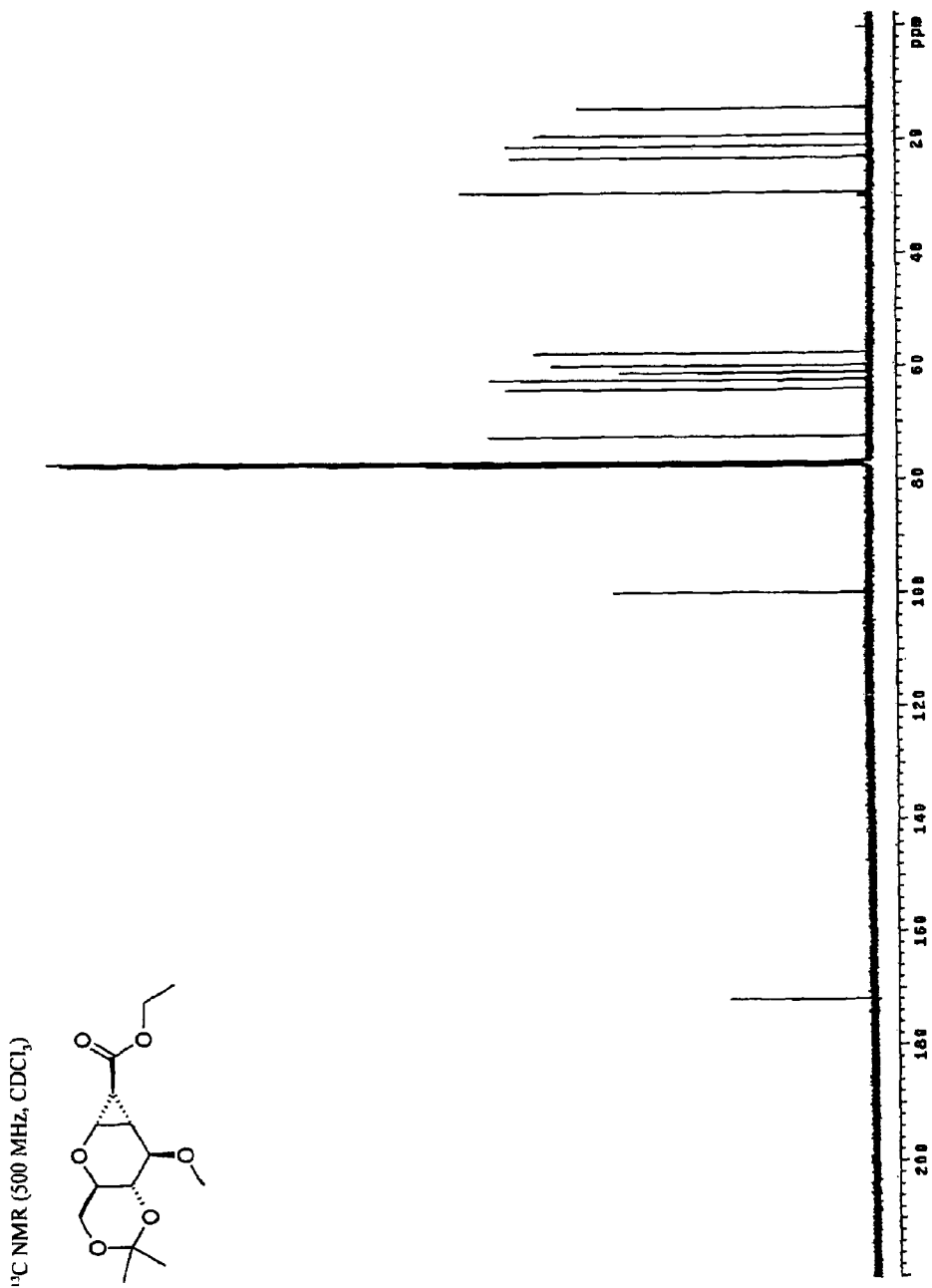

Treatment of Compound 6a (1.0 g, 3.7 mmol) with NaH (0.22 g, 5.5 mmol) and methyl iodide (0.34 mL, 5.5 mmol) in DMF (10 mL) yielded a crude mixture. Extractive workup followed by column chromatography (SiO$_2$, a gradient of pure hexanes to a 2:3 ratio of ethyl acetate in hexanes) on the crude mixture afforded a white solid (0.57 g, 2.0 mmol) 54% yield: mp=65-68° C. $^1$H NMR (500 MHz, CDCl$_3$): δ 4.17-4.11 (m, 2H), 3.96 (dd, 1H, J=8.0, 2.5 Hz), 3.82 (dd, 1H, J=11.0, 5.5 Hz), 3.68-3.64 (m, 2H), 3.50-3.48 (m, 1H), 3.50 (s, 3H), 3.12 (ddd, 1H, J=10.0, 10.0, 5.5 Hz), 2.03 (dd, 1H, J=6.0, 2.5 Hz), 1.70-1.67 (m, 1H), 1.50 (s, 3H), 1.40 (s, 3H), 1.27 (t, 3H, J=7.0 Hz) (FIG. 23). $^{13}$C NMR (500 MHz, CDCl$_3$): δ 171.8, 99.7, 77.5, 72.3, 63.9, 62.2, 60.9, 59.7, 57.4, 29.0, 22.9, 20.9, 19.0, 14.2 (FIG. 24). HRMS (m/z): [M+H]$^+$ calculated for C$_{14}$H$_{23}$O$_6$, 287.1489. found 287.1495 (A 0.6 mmu).

Ethyl (2R,4aR,5aS,6aS,7R,7aS)-7-methoxy-2-(4-methoxyphenyl)hexahydro-4H-cyclopropa[5,6]pyrano[3,2-d][1,3]dioxine-6-carboxylate (Compound 18)

Figure 42:
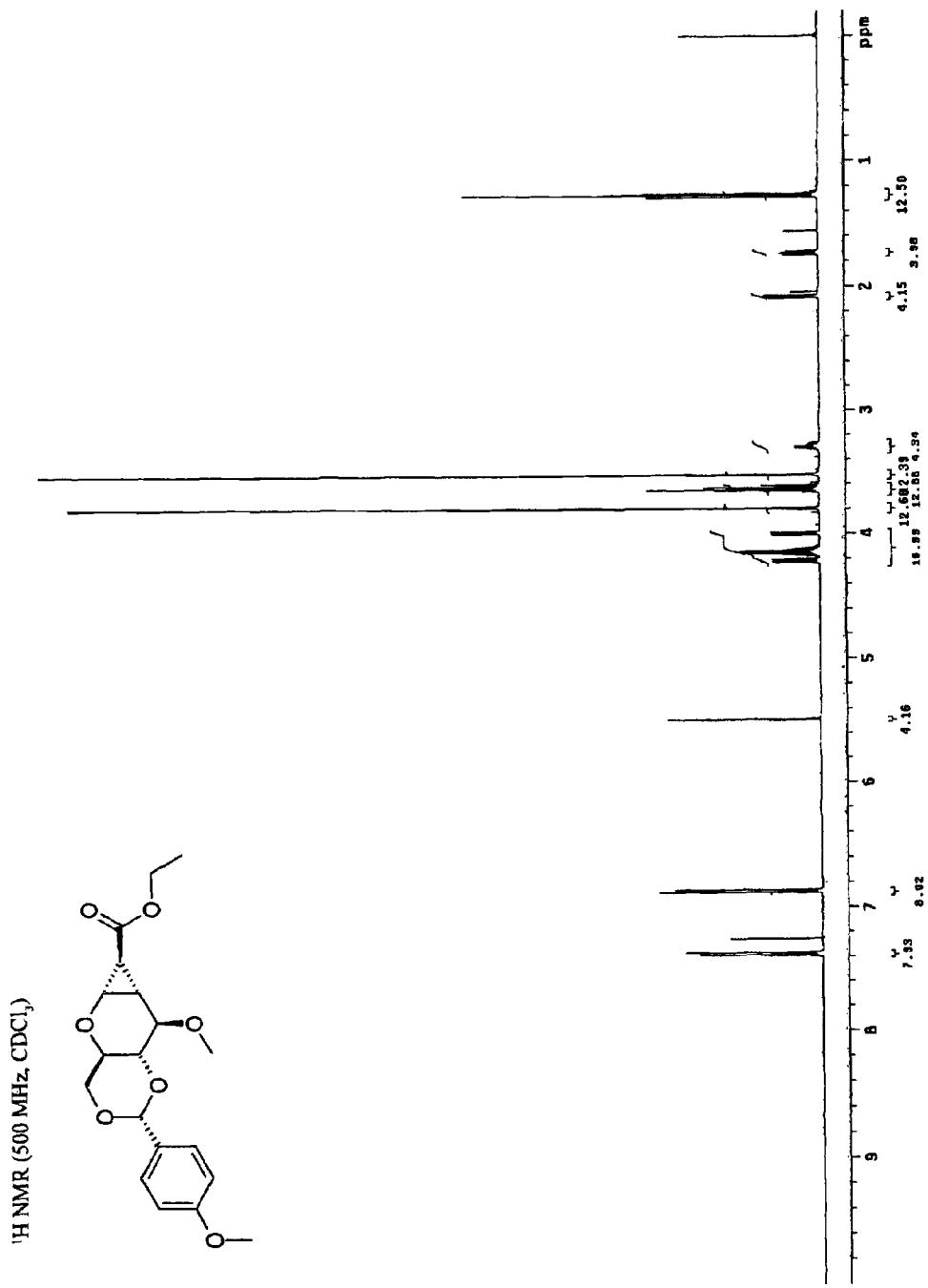
FIGS. 42 and 43 are NMR Spectra for Compound 18.
Figure 43:
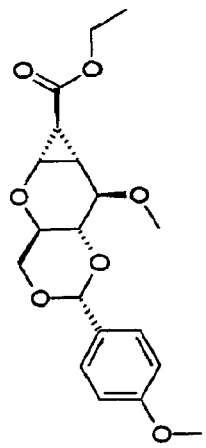
Figure 43:
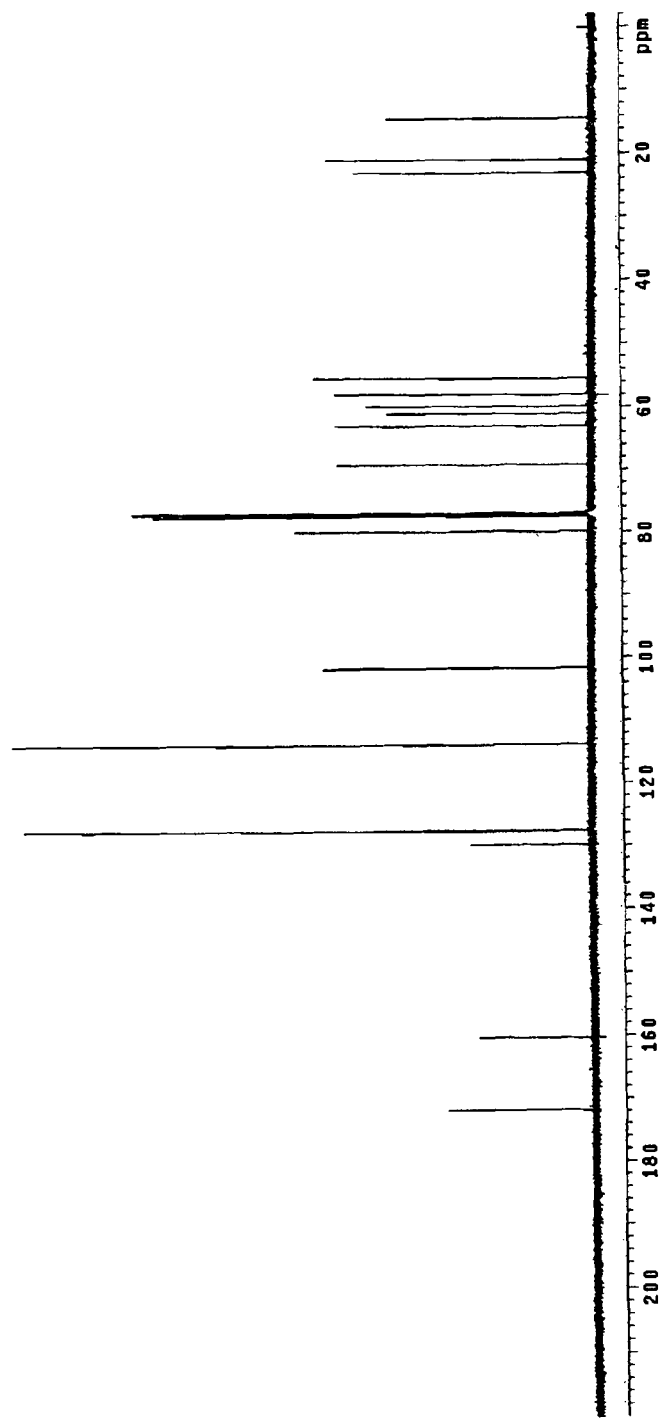

Treatment of Compound 16 (0.63 g, 1.8 mmol) with NaH (0.11 g, 2.7 mmol) and methyl iodide (0.17 mL, 2.7 mmol) in DMF (15 mL) yielded a crude mixture. Extractive workup followed by column chromatography (SiO$_2$ a gradient of pure hexanes to a 9:11 ratio of ethyl acetate in hexanes), and recrystallization on the crude mixture (1:4 ratio of diethyl ether in hexanes) afforded a white solid (0.26 g. 0.71 mmol) 40% yield: mp=132-134° C. $^1$H NMR (500 MHz, CDCl$_3$): δ 7.40-7.26 (m, 2H), 6.90-6.87 (m, 2H), 5.50 (s, 1H), 4.23 (dd, 1H, J=10.5, 5.0 Hz), 4.18-4.12 (m, 2H), 4.01 (dd, 1H, J=7.5, 3.0 Hz), 3.80 (s, 3H), 3.67-3.62 (m, 3H), 3.53 (s, 3H), 3.32-3.27 (m, 1H), 2.08 (dd, 1H, J=5.5, 2.5 Hz), 1.75-1.72 (m, 1H), 1.28 (t, 3H, J=7.0 Hz) (FIG. 42). $^{13}$C NMR (500 MHz, CDCl$_3$): δ 171.7, 160.1, 129.7, 127.5 (2 C's), 113.6 (2 C's), 101.5, 79.7, 76.9, 69.0, 62.9, 61.0, 59.8, 57.9, 55.3, 22.9, 20.8, 14.2 (FIG. 43). HRMS (m/z): [M]$^+$ calculated for C$_{19}$H$_{24}$O$_7$, 364.1522. found 364.1524 (Δ 0.2 mmu).

Example 9

Preparation of ethyl (2R,4aR,5aS,6aR,7R,7aS)-7-hydroxy-2-(4-methoxyphenyl)hexahydro-4H-cyclopropa[5,6]pyrano[3,2-d][1,3]dioxine-6-carboxylate (Compound 16)

Figure 25:
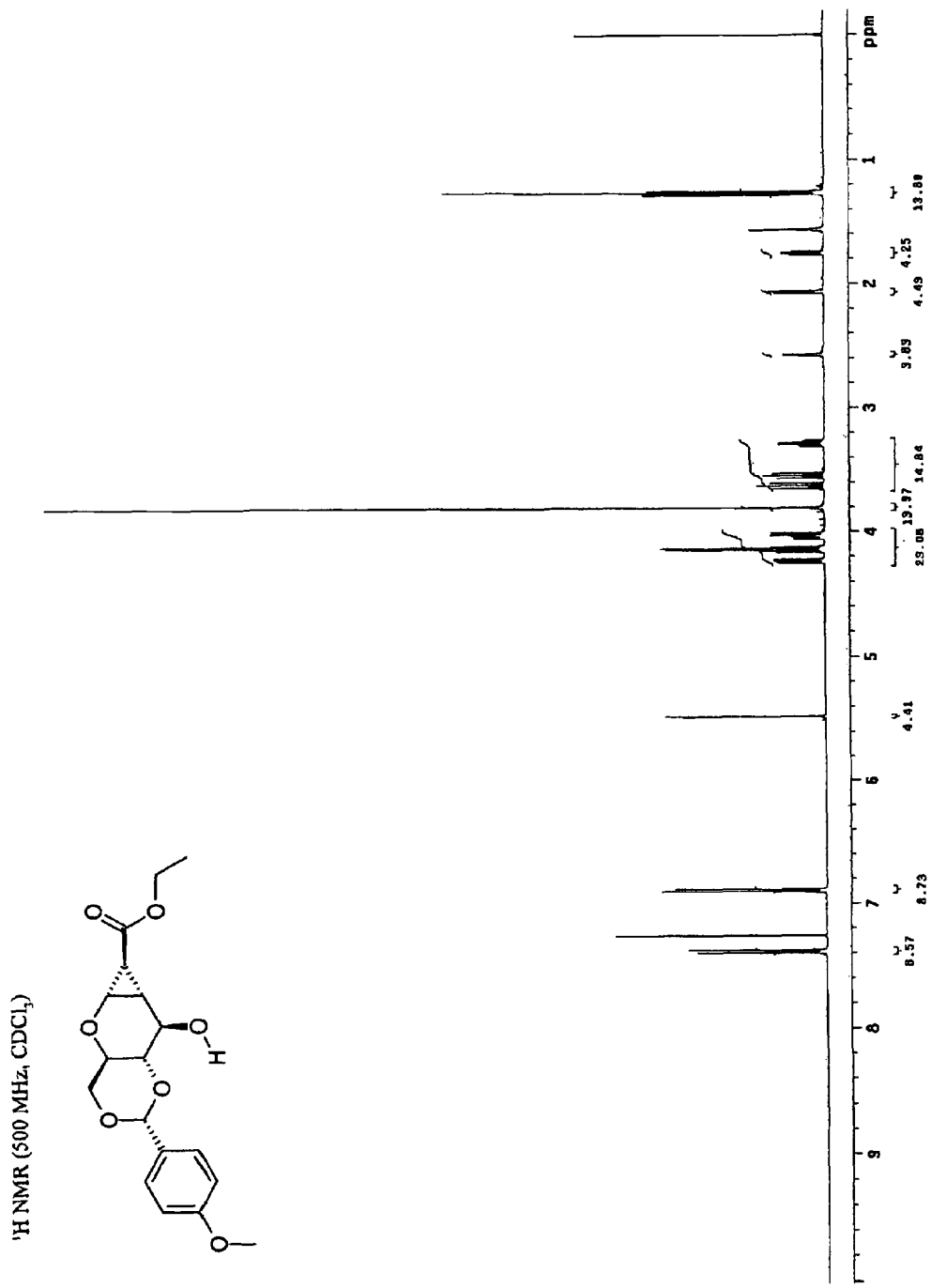
FIGS. 25 and 26 are NMR Spectra for Compound 16.
Figure 26:
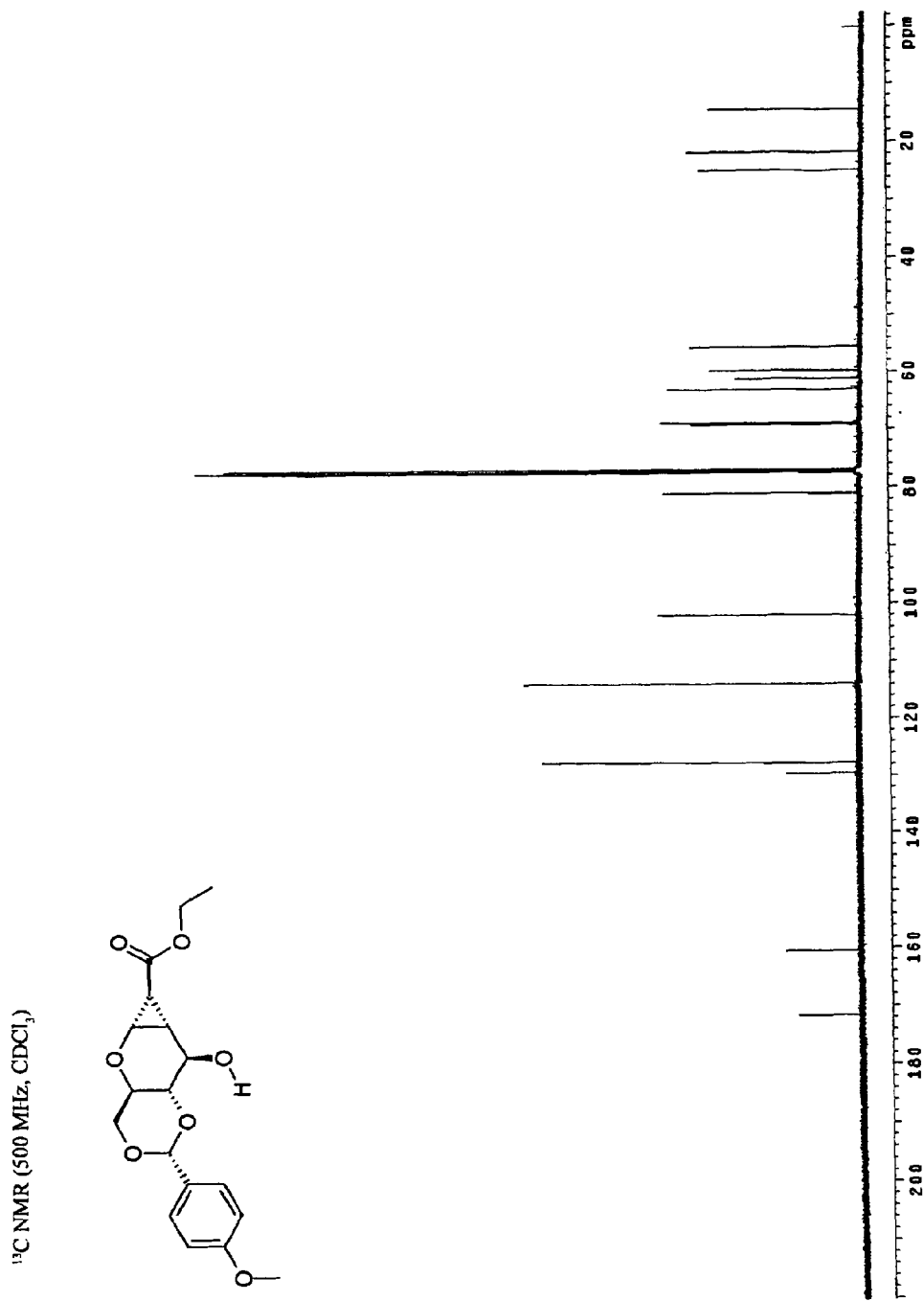

A solution of Compound 2 (1.3 g, 5.6 mmol), p-anisaldelyde dimethyl acetal (1.5 g, 8.4 mmol) and p-TsOH H20 (9.5 mg, 0.05 mmol) in DMF (25 mL) was heated at 50° C. under aspirator pressure for 2 hours. The reaction was heated at 60° C. for 10 min to remove the solvent in vacuo and then cooled to room temperature. The crude mixture was diluted in DCM (45 mL), washed with cold sodium bicarbonate (1×15 mL) cold water (3×15 mL), and brine (1×15 mL). The organic layer was dried over Na$_2$SO$_4$, filtered, and concentrated in vacuo. Column chromatography (SiO$_2$, a gradient of pure hexanes to a 2:3 ratio of ethyl acetate in hexanes) of the crude mixture afforded a white solid (0.9 g, 2.7 mmol) 48% yield: mp=118-120° C. $^1$H NMR (500 MHz, CDCl$_3$): δ 7.40-7.39 (m, 2H), 6.90-6.89 (m, 2H), 5.48 (s, 1H), 4.24 (dd, 1H, J=11.0, 5.5 Hz), 4.13 (q, 2H, J=7.0 Hz), 4.05 (dd, 1H, J=8.5, 1.0 Hz), 4.02 (dd, 1H, J=7.5, 3.0 Hz), 3.82 (s, 3H), 3.63 (apparent t, 1H, J=10.0 Hz), 3.55 (dd, 1H, J=10.0, 8.5 Hz), 3.29 (ddd, 1H, J=10.0, 10.0, 5.0 Hz), 2.06 (dd, 1H, J=5.0, 2.0 Hz), 1.77-1.74 (m, 1H), 1.27 (t, 3H, J=7.0 Hz) (FIG. 25). $^{13}$C NMR (500 MHz, CDCl$_3$): δ 171.5, 160.3, 129.4, 127.5 (2 C's), 113.8 (2 C's), 101.8, 80.8, 69.0, 68.7, 62.9, 60.9, 59.5, 55.2, 24.7, 21.6, 14.2 (FIG. 26). Anal. calculated for C$_{18}$H$_{22}$O$_7$: C, 61.71; H, 6.33. Found C, 61.63; H, 6.58.

Example 10

Preparation of ethyl (2R,4aR,5aS,6aS,7R,7aR)-2-(4-methoxyphenyl)-7(sulfamoyloxy)hexahydro-4H-cyclopropa[5,6]pyrano[3,2-d][1,3]dioxine-6-carboxylate (Compound 17b)

Figure 28:
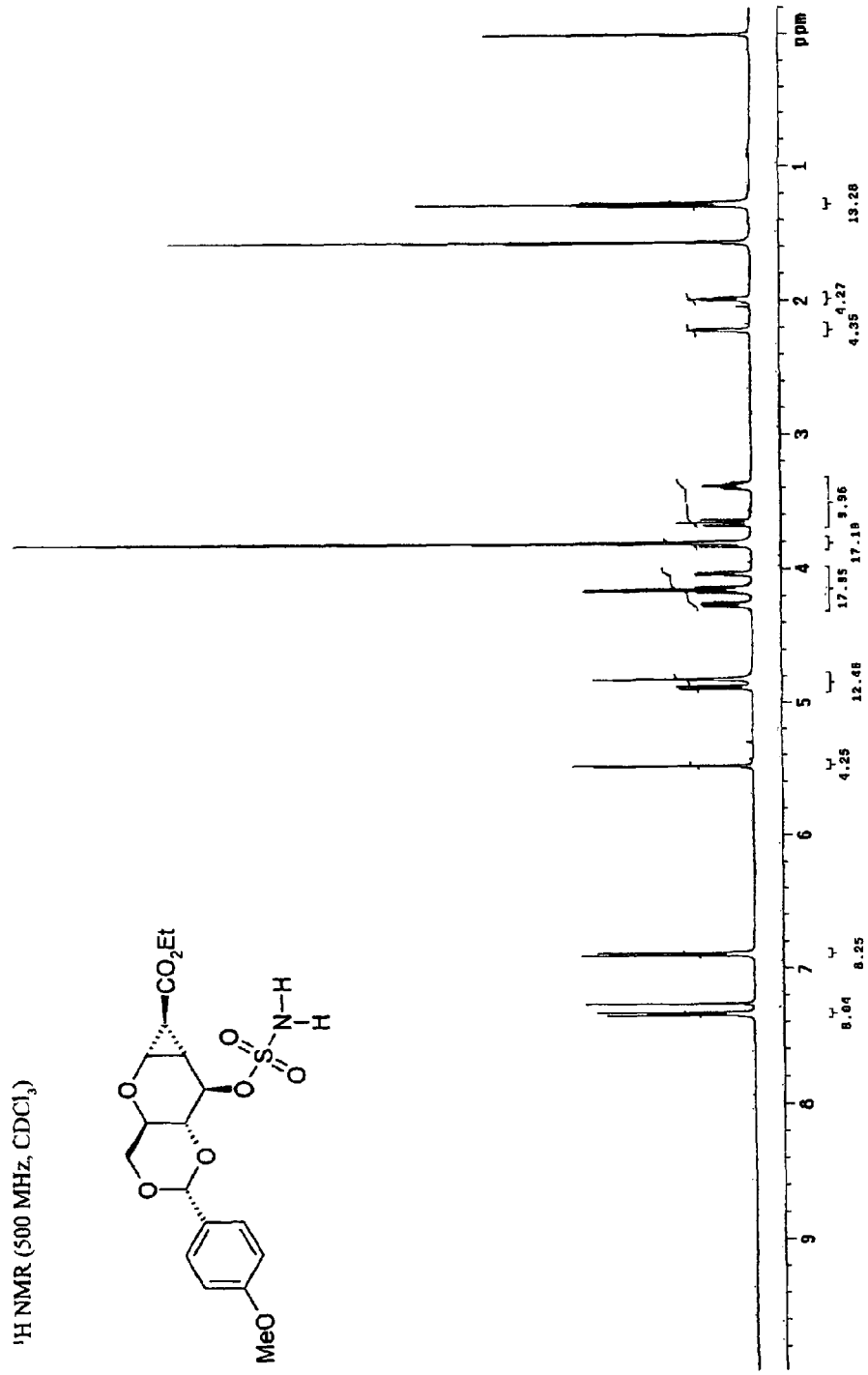
FIGS. 28 and 29 are NMR Spectra for Compound 17b.
Figure 29:
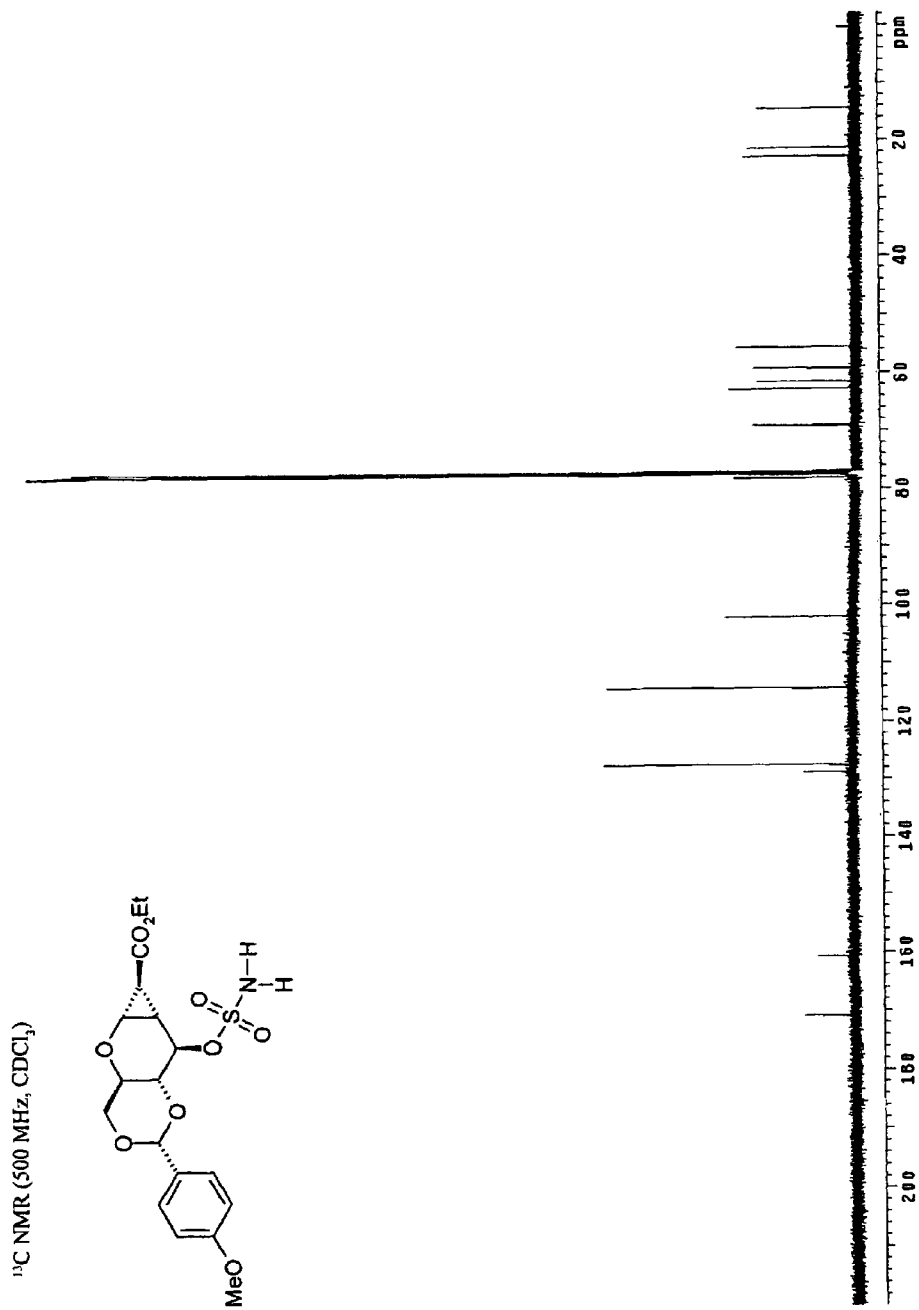

Compound 16 (0.60 g, 1.7 mmol) was added to a dry 3-neck flask containing NaH (60% dispersion in mineral oil, 0.05 g, 0.86 mmol) in DMF (10 ml) at −10° C. After 5 min at −10° C., the reaction mixture was cooled to −20° C. and sulfamoyl chloride (0.33 g, 2.9 mmol) was added in portions. The reaction mixture was stirred for an additional 20 min at −20° C., quenched with H$_2$O, and diluted with ice cold H$_2$O (20 mL) and ethyl acetate (50 mL). The aqueous layer was removed, and the organic layer was washed with ice cold water (2×20 mL) and brine (1×20 mL). The organic layer was dried over Na$_2$SO$_4$, filtered, and concentrated in vacuo. Column chromatography (SiO$_2$, a gradient of pure hexanes to a 1:4 ratio of ethyl acetate in hexanes) on the crude mixture afforded a white solid (0.39 g, 0.98 mmol) 16% yield. $^1$H NMR (500 MHz, CDCl$_3$): δ 7.35-7.33 (m, 2H), 6.90-6.88 (m, 2H), 5.48 (s, 1H), 4.86 (dd, 1H, J=7.0, 2.5 Hz), 4.82 (s, br, 2H), 4.27 (dd, 1H, J=10.5, 5.0 Hz), 4.16 (q, 2H, J=7.0 Hz), 4.04 (dd, 1H, J=7.5, 3.0 Hz), 3.83-3.80 (m, 1H), 3.80 (s, 3H) 3.66 (dd, 1H, J=10.5, 9.5 Hz), 3.39 (ddd, 1H, J=10.0, 10.0, 5.0 Hz), 2.22 (dd, 1H, J=5.5, 2.5 HZ), 2.01-1.99 (m, 1H), 1.28 (t, 3H. J=7.0 Hz) (FIG. 28). $^{13}$C NMR (500 MHz, CDCl$_3$): δ 170.6, 160.6, 128.6, 127.3 (2 C's) 114.0 (2 C's), 101.9, 77.9, 68.9, 62.6, 61.3, 58.9, 55.3, 22.4, 21.0, 14.2 (FIG. 29). HRMS (m/z): [M+H]$^+$ calculated for C$_{18}$H$_{24}$NO$_9$S, 430.1166. found 430.1169 (Δ 0.3 mmu).

Example 11

General Procedure for the Preparation of Compounds 20a, 20b, 20c, 20d, 20e and 20f (Benzylidenes)

A suspension of freshly fused ZnCl$_2$ (1.5 g, 10.8 mmol), aldehyde (1.4 mL, 14.0 mmol), and Compound 2 (0.5 g, 2.2 mmol) was stirred at room temperature for 2 to 12 hours.

Ethyl (2R,4aR,5aS,6aR,7R,7aS)-7-hydroxy-2-phenylhexahydro-4H-cyclopropa[5,6]pyrano[3,2-d][1,3]dioxine-6-carboxylate (Compound 20a)

Figure 30:
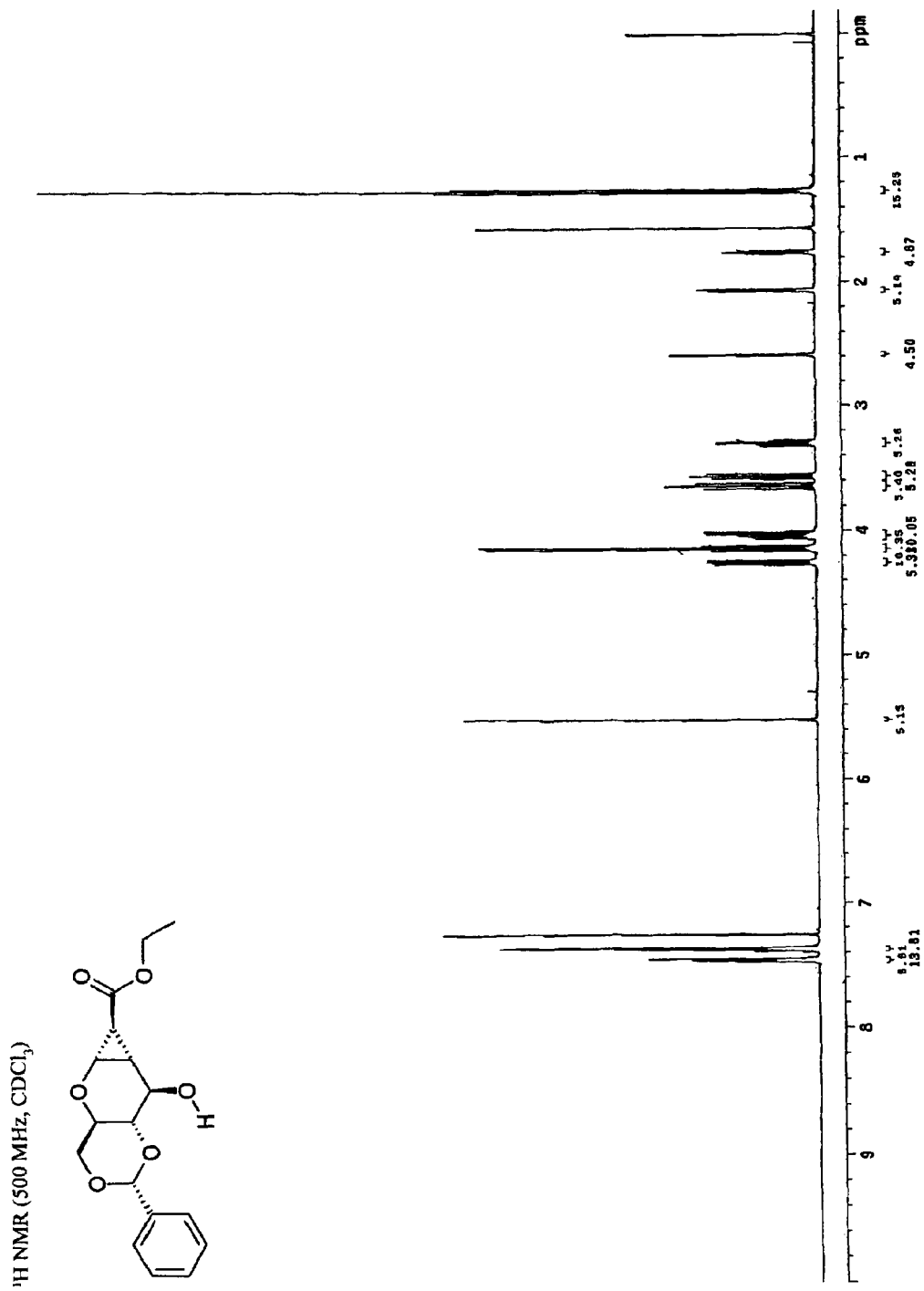
Figure 31:
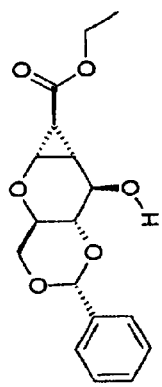
Figure 31:
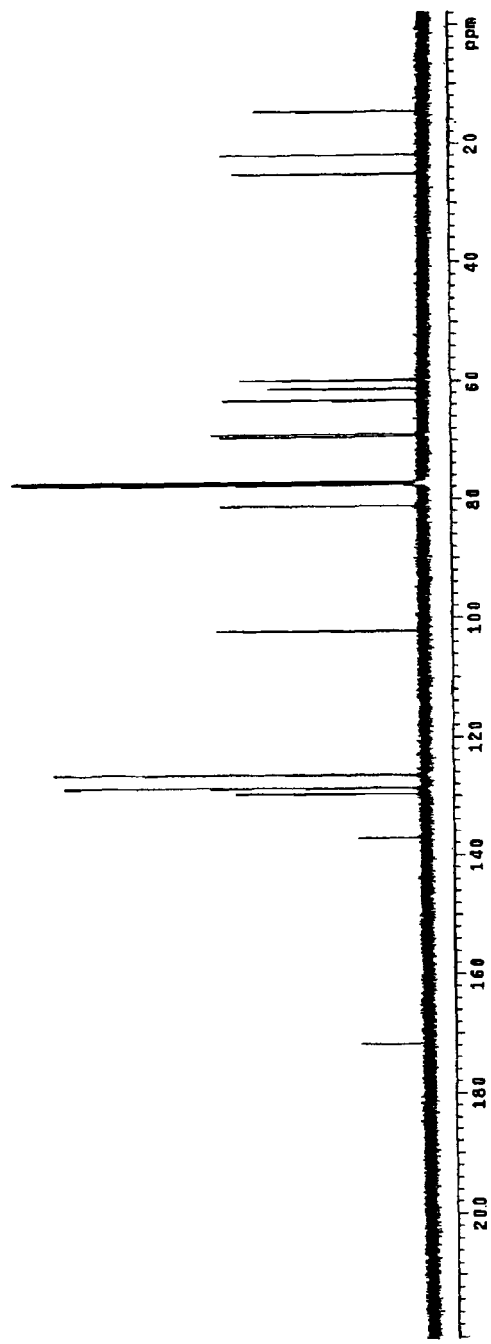

Treatment of Compound 6a (0.62 g, 2.6 mmol) with zinc chloride (1.6 g, 11.8) and benzaldehyde (1.6 mL, 15.5 mmol) yielded a crude mixture. Column chromatography (SiO$_2$, a gradient of pure dichloromethane to a 4:21 ratio of ethyl acetate in dichloromethane) on the crude mixture afforded a white solid (0.30 g, 0.94 mmol) 35% yield: mp=137-139° C. $^1$H NMR (500 MHz, CDCl$_3$): δ 7.47-7.45 (m, 2H), 7.38-7.36 (m, 2H), 5.52 (s, 1H), 4.26 (dd, 1H, J=11.0, 5.5 Hz), 4.13 (q, 2H, J=7.0 HZ), 4.05 (dd, 1H, J=8.0, 2.0 Hz), 4.02 (dd, 1H, J=7.5, 2.5 Hz), 3.65 (apparent t. 1H, J=10.0 Hz), 3.57 (dd, 1H, J=9.5, 8.5 Hz), 3.30 (ddd, 1H, J=10.0, 10.0, 5.0 Hz), 2.59 (d, 1H, J=3.0 Hz), 2.06 (dd, 1H, J=5.5, 3.0 Hz), 1.77-1.74 (m, 1H), 1.27 (t, 3H, J=7.0 Hz, CH$_3$) (FIG. 30). $^{13}$C NMR (500 MHz, CDCl$_3$): δ 171.5, 136.9, 129.4, 128.4 (2 C's), 126.2 (2 C's), 101.9, 80.9, 69.0, 68.6, 62.9, 61.0, 59.5, 24.7, 21.6, 14.2 (FIG. 31). HRMS (m/z): [M+H]$^=$ calculated for C$_{17}$H$_{21}$O$_6$, 321.1333. found 321.1329 (Δ 0.4 mmu).

Ethyl (2R,4aR,5aS,6aR,7R,7aS)-7-hydroxy-2-[4-(propan-2-yl)phenyl]hexahydro-4H-cyclopropa[5,6]pyrano[3,2-d][1,3]dioxine-6-carboxylate (Compound 20b)

Figure 32:
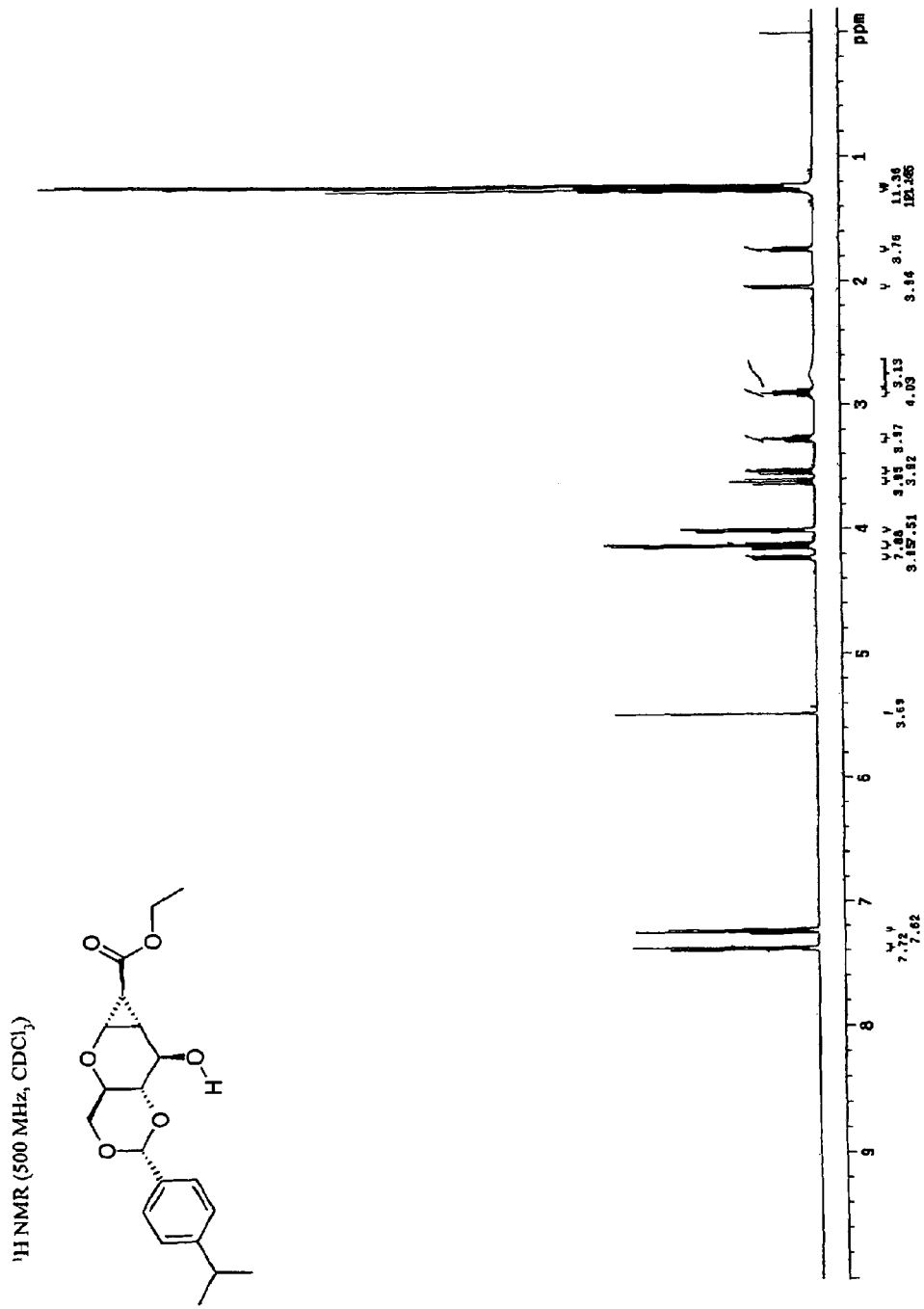
FIGS. 32 and 33 are NMR Spectra for Compound 20b.
Figure 33:
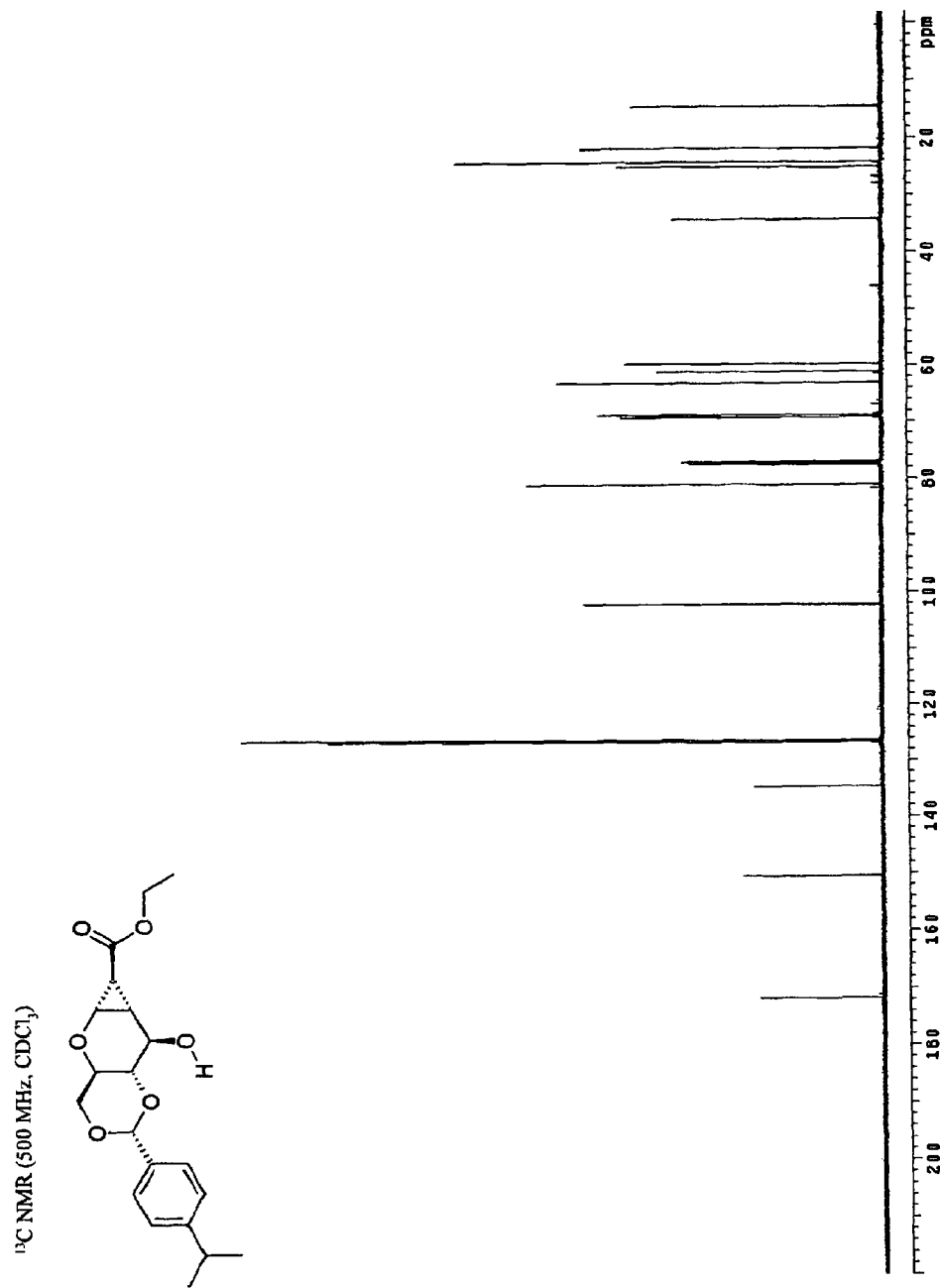

Treatment of Compound 6a (0.92 g, 4.4 mmol) with zinc chloride (2.5 g, 18.3 mmol) and 4-isopropylbenzaldehyde (3.7 mL, 25.4 mmol) yielded a crude mixture. Column chromatography (SiO$_2$, a gradient of dichloromethane (1% TEA) to a 3:17 ratio of ethyl acetate in dichloromethane (1% TEA)) on the crude mixture afforded a white solid (0.24 g, 0.66 mmol) 16% yield. $^1$H NMR (500 MHz, CDCl$_3$): δ 7.39 (d, 2H, J=8.5 Hz), 7.24 (d, 2H, J=8.0 Hz), 5.49 (s, 1H), 4.24 (dd, 1H, J=10.5, 5.0 Hz), 4.14 (q, 2H, J=7.0 Hz), 4.01 (dd, 2H, J=8.0, 3.0 Hz), 3.62 (apparent t, 1H, J=10.0 Hz), 3.53 (dd, 1H, J=9.5, 8.5 Hz), 3.27 (ddd, 1H, J=10.0, 10.0, 5.0 Hz), 2.90 (septet, 1H, J=7.0 Hz), 2.05 (dd, 1H, J=5.5, 3.0 Hz), 1.76-1.73 (m, 1H), 1.27 (t, 3H, J=7.0 Hz), 1.24 (s, 3H), 1.23 (s, 3H) (FIG. 32). $^{13}$C NMR (500 MHz, CDCl$_3$): δ 171.6, 150.2, 134.4, 126.5 (2 C's), 126.2 (2 C's), 102.0, 80.9, 69.0, 68.6, 62.9, 60.9, 59.5, 34.0, 24.8, 23.9 (2 C's), 21.5, 14.2 (FIG. 33). HRMS (m/z): [M+H]$^+$ calculated for C$_{20}$H$_{27}$O$_6$, 363.1802. found 363.1796 (Δ 0.6 mmu).

Ethyl (2R,4aR,5aS,6aR,7R,7aS)-2-(4-tert-butylphenyl)-7-hydroxyhexahydro-4H-cyclopropa[5,6]pyrano[3,2-d][1,3]dioxine-6-carboxylate (Compound 20c)

Figure 34:
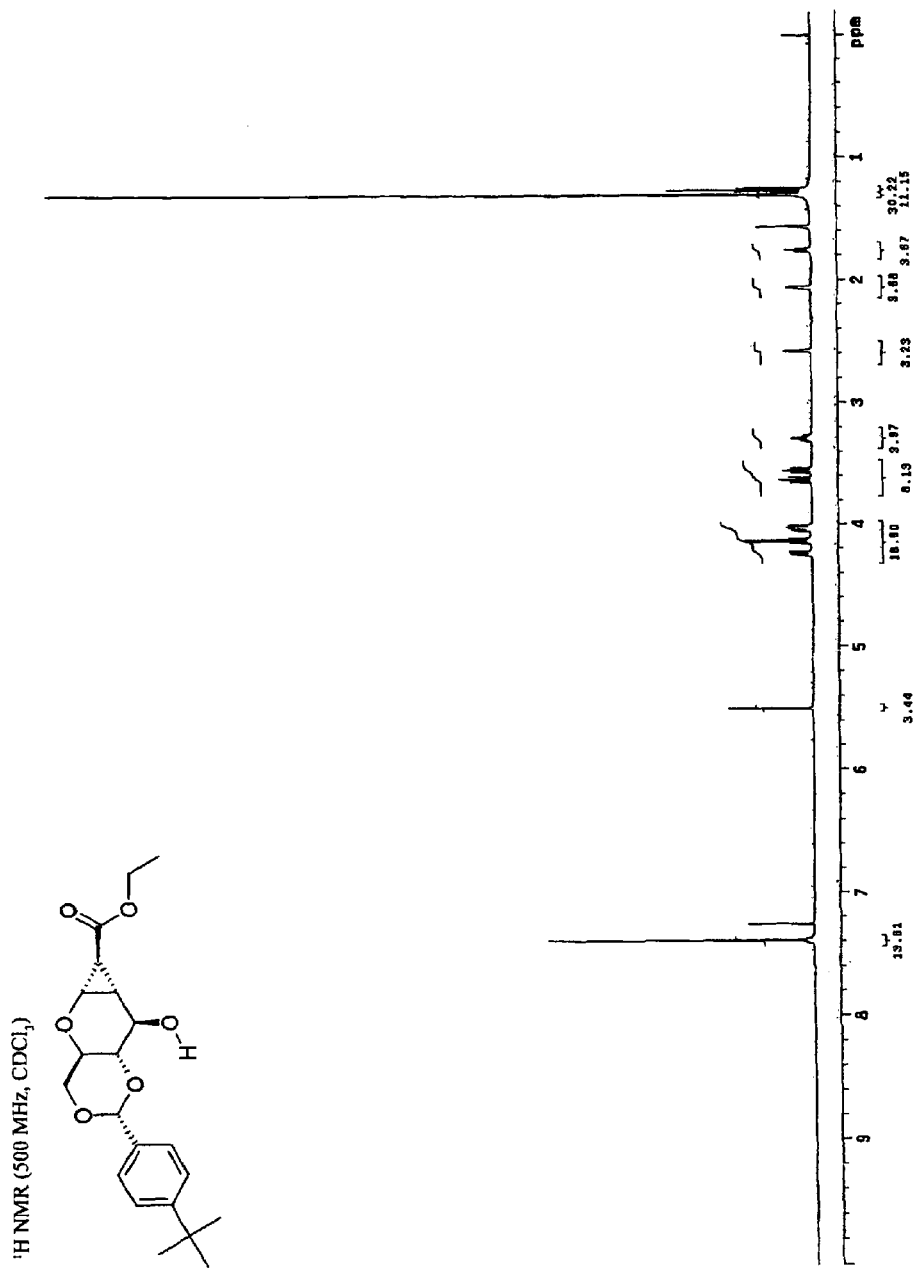
FIGS. 34 and 35 are NMR Spectra for Compound 20c.
Figure 35:
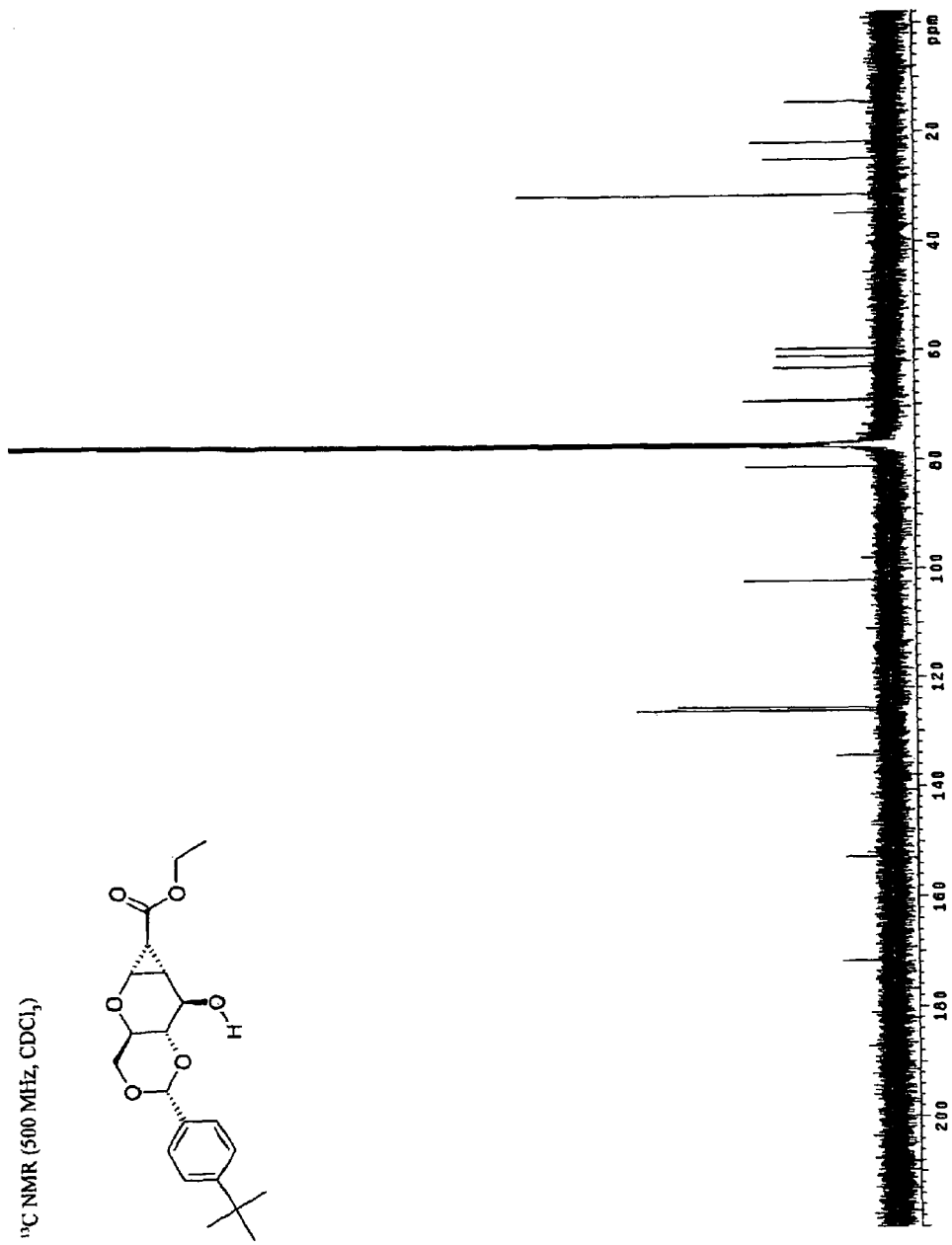
Figure 35:
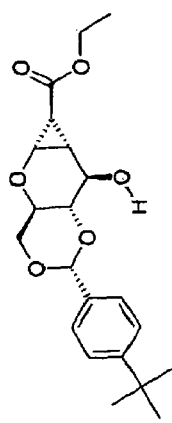

Treatment of Compound 6a (0.4 g, 1.7 mmol) with zinc chloride (1.2 g, 8.6 mmol) and 4-tert-butylbenzaldehyde (1.6 ml, 9.5 mmol) yielded a crude mixture. Column chromatography ($SiO_2$, a gradient of pure dichloromethane to a 3:22 ratio of ethyl acetate in dichloromethane) followed by preparative TLC ($SiO_2$, 2:49 ratio of ethanol in chloroform) on the crude mixture afforded a white solid (0.28 g, 0.74 mmol) 43% yield: mp=113-116° C. $^1$H NMR (500 MHz, $CDCl_3$): δ 7.39 (s, 4H), 4.24 (dd, 1H, J=10.5, 5.0 Hz), 4.14 (q, 2H, J=7.0 Hz), 4.05-4.01 (m, 2H), 3.63 (apparent t, 1H, J=10.0 Hz), 3.56 (apparent dd, 1H, J=10.0, 8.5 Hz), 3.29 (ddd, 1H, J=10.0, 10.0, 5.0 Hz), 2.58 (5, broad, 1H), 2.06 (dd, 1H, J=5.5, 3.0 Hz), 1.77-1.74 (m, 1H), 1.30 (s, 9H), 1.27 (t, 3H, J=8.5 Hz) (FIG. 34). $^{13}$C NMR (500 MHz, $CDCl_3$): δ 171.5, 152.5, 134.2, 125.9 (2 C's), 125.4 (2 C's), 102.0, 81.0, 69.1, 68.8, 63.0, 59.5, 34.7, 31.3 (3 C's), 24.8, 21.7, 14.3 (FIG. 35). HRMS (m/z): [M+H]$^+$ calculated for $C_{21}H_{29}O_6$, 377.1959. found 377.1964 (Δ 0.5 mmu).

Ethyl (2R,4aR,5aS,6aR,7R,7aS)-2-(2,4-difluorophenyl)-7-hydroxyhexahydro-4H-cyclopropa[5,6]pyrano[3,2-d][1,3]dioxine-6-carboxylate (Compound 20d)

Figure 36:
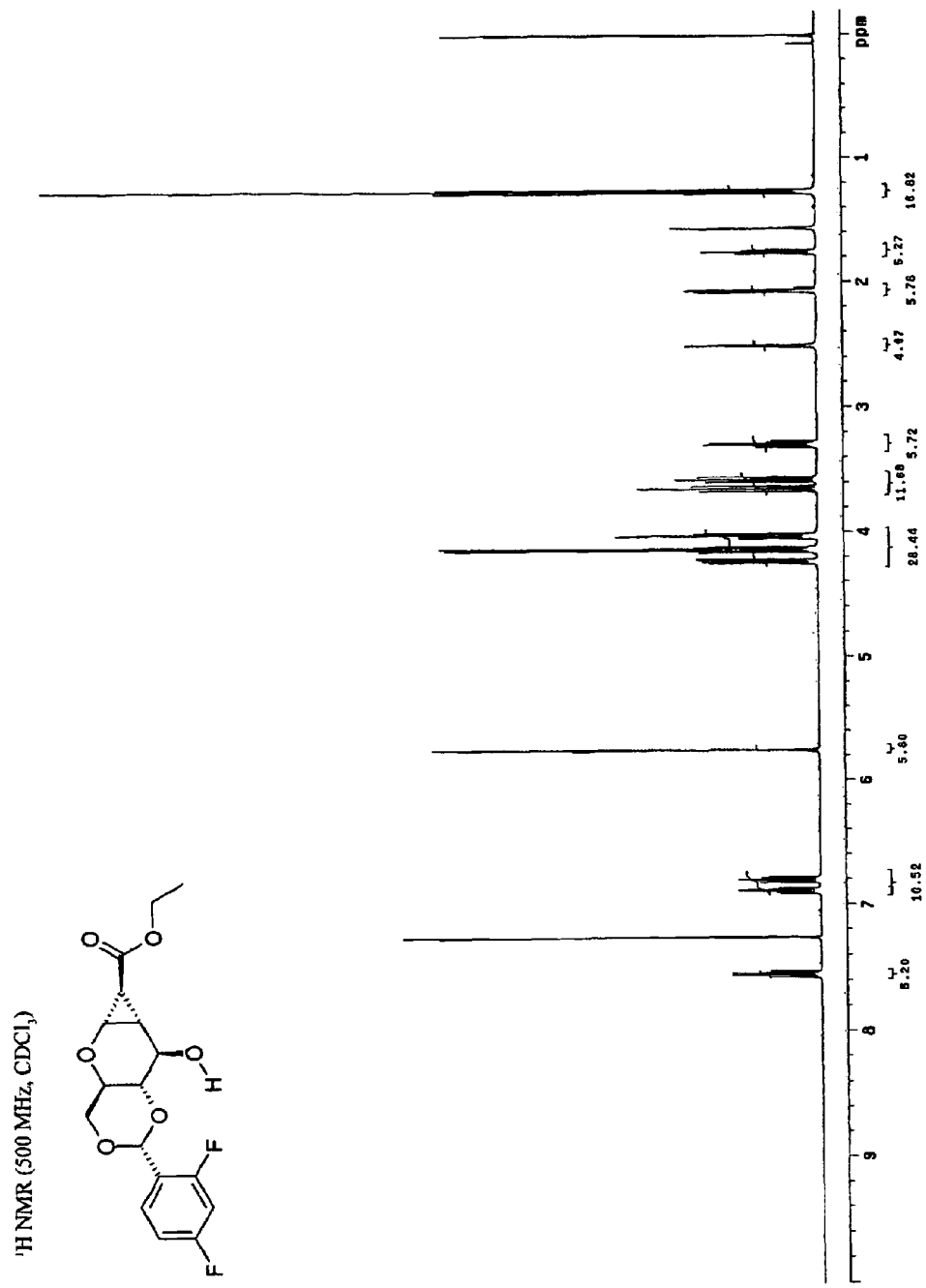
FIGS. 36 and 37 are NMR Spectra for Compound 20d.
Figure 37:
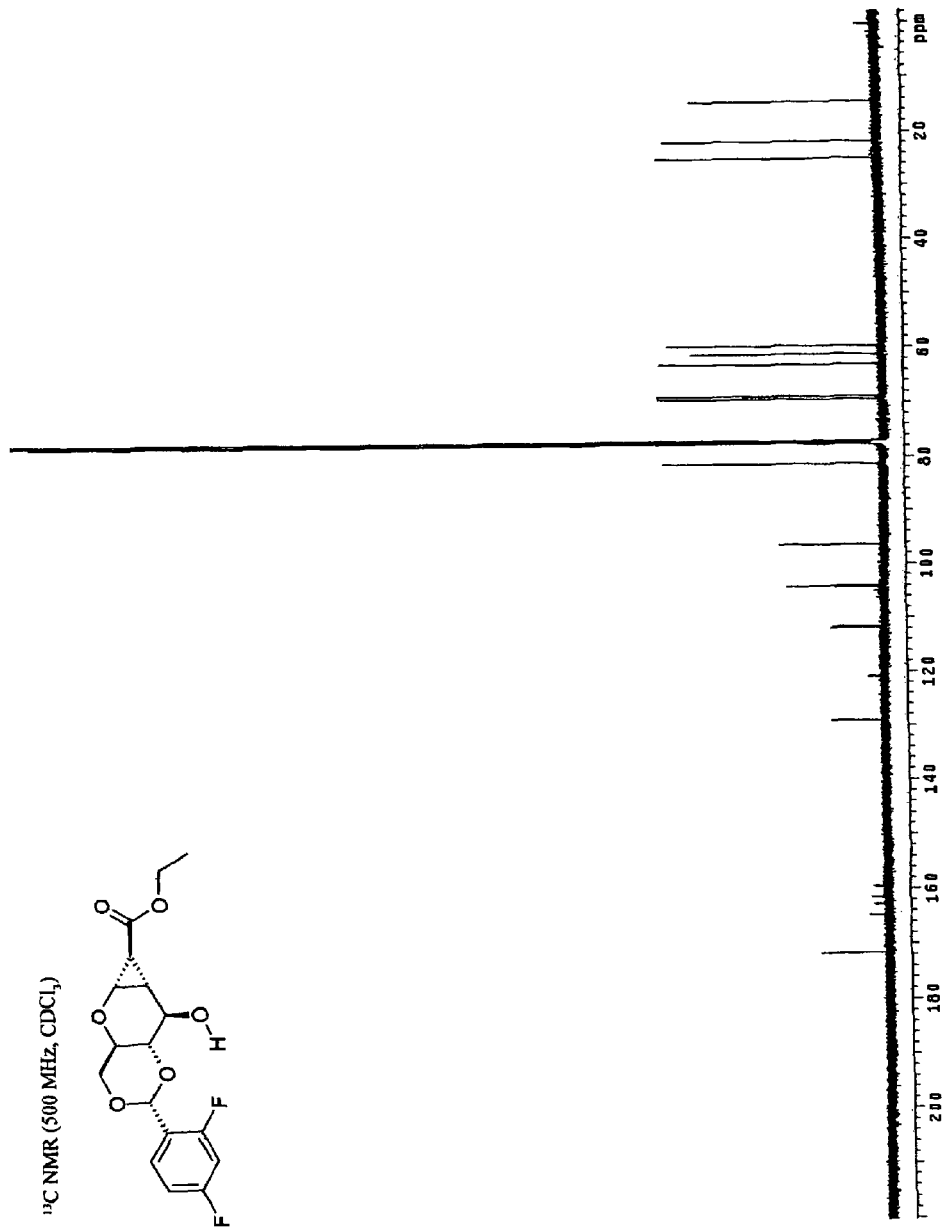

Treatment of Compound 6a (0.5 g, 2.2 mmol) with zinc chloride (1.5 g, 10.8 mmol) and aldehyde (2.4 mL, 21.5 mmol) yielded a crude mixture. Column chromatography ($SiO_2$, a gradient of pure dichloromethane to a 3:17 ratio of ethyl acetate in dichloromethane) on the crude mixture afforded a white solid (0.48 g, 1.36 mmol) 63% yield: mp=130-133° C. $^1$H NMR (500 MHz, $CDCl_3$): δ 7.58-7.53 (m, 1H), 6.91-6.87 (m, 1H), 6.82-6.78 (m, 1H), 5.76 (s, 1H), 4.24 (dd, 1H, J=11.0, 5.0 Hz) 4.14 (q, 2H, J=7.0 Hz), 4.05-4.01 (m, 2H), 3.65 (apparent t, 1H, J=10.0 Hz), 3.59 (dd, 1H, J=10.0, 9.0 Hz), 3.30 (ddd, 1H, J=10.0, 9.5, 5.0 Hz), 2.51 (d, 1H, J=2.5 Hz), 2.08 (dd, 1H, J=6.0, 3.0 Hz), 1.77-1.74 (m, 1H), 1.27 (t, 3H, J=7.0 Hz) (FIG. 36). $^{13}$C NMR (500 MHz, $CDCl_3$): δ 171.4, 164.5, 161.3, 128.9, 120.6, 111.5, 103.9, 96.2, 81.0, 69.1, 68.6, 62.7, 61.0, 59.4, 24.7, 21.5, 14.2 (FIG. 37). Anal. calculated for $C_{17}H_{18}F_2O_6$: C, 57.30; H, 5.09. Found C, 57.59; H, 5.02.

Ethyl (2R,4aR,5aS,6aR,7R,7aS)-7-hydroxy-2-(3-methoxyphenyl)hexahydro-4H-cyclopropa[5,6]pyrano[3,2-d][1,3]dioxine-6-carboxylate (Compound 20e)

Figure 38:
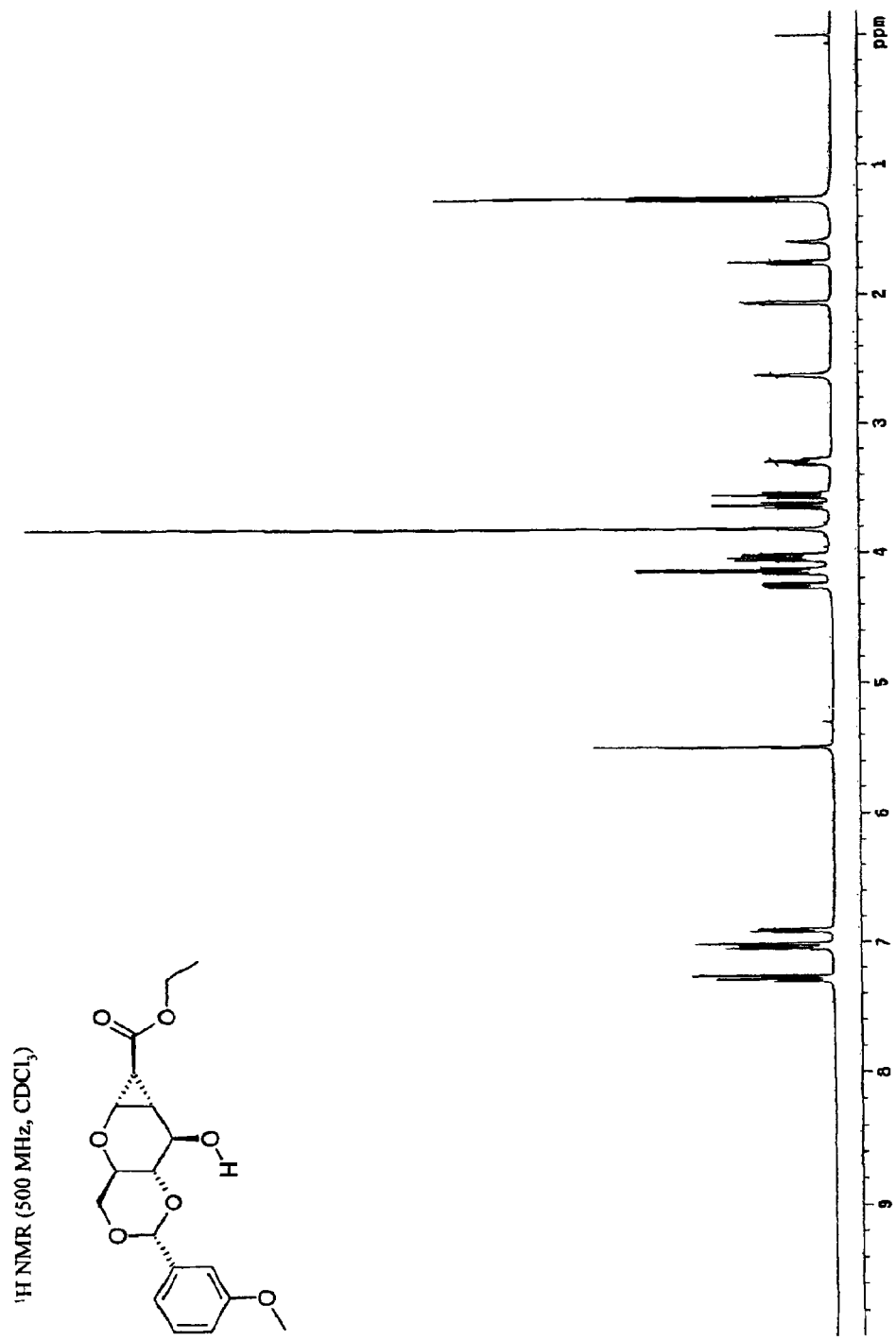
FIGS. 38 and 39 are NMR Spectra for Compound 20e.
Figure 39:
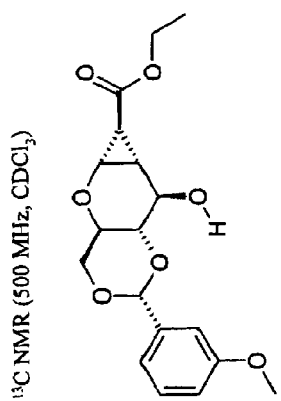
Figure 39:
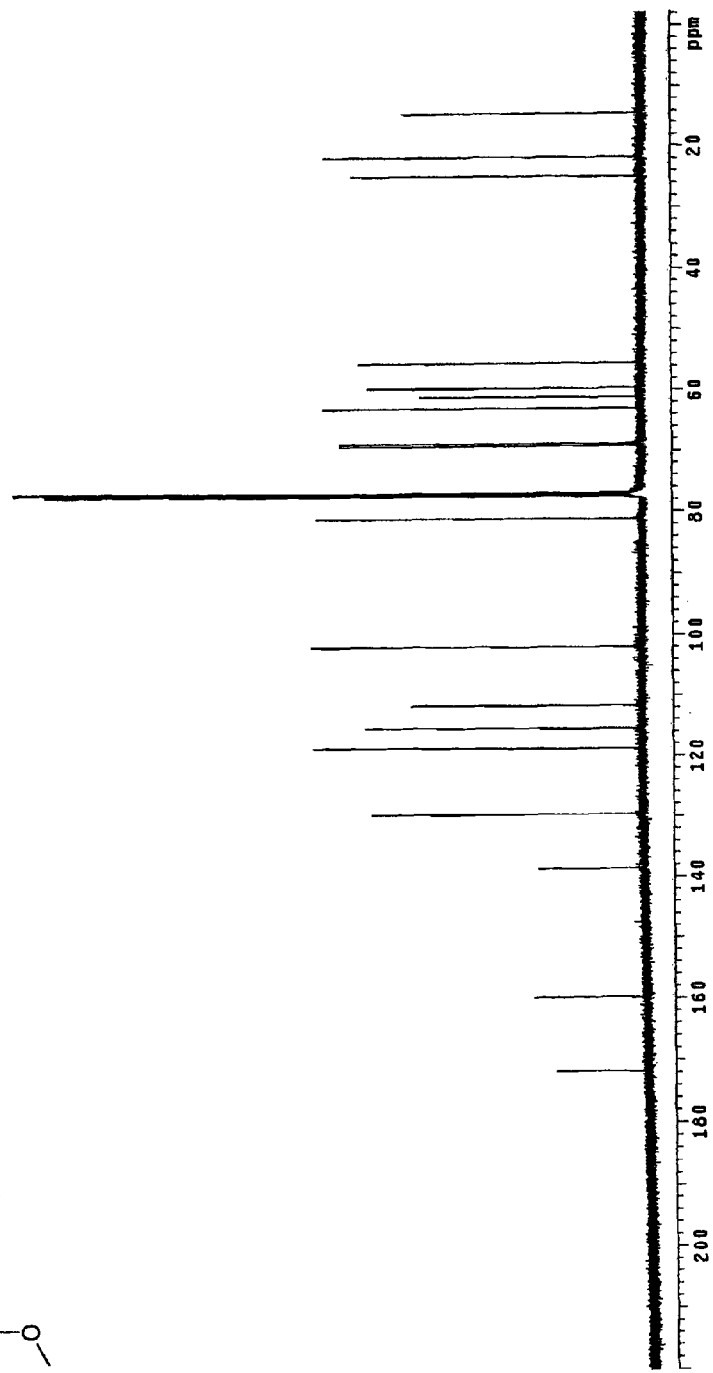

Treatment of Compound 6a (0.5 g, 2.2 mmol) with zinc chloride (1.5 g, 10.8 mmol) and m-methoxybenzaldehyde (1.7 mL, 14.0 mmol) yielded a crude mixture. Column chromatography ($SiO_2$, a gradient of pure dichloromethane to a 3:17 ratio of ethyl acetate in dichloromethane) followed by preparative TLC ($SiO_2$, a ratio of 1:9 ethyl acetate in DCM) on the crude mixture afforded a white solid (0.30 g, 1.36 mmol) 63% yield: mp=107° C. $^1$H NMR (500 MHz, $CDCl_3$): (57.29 (apparent t, 1H, J=7.0 Hz), 7.04 (d, 1H, J=7.5 Hz), 7.02 (5, 1H), 6.92-6.90 (m, 1H), 5.50 (5, 1H), 4.26 (dd, 1H, J=10.5, 5.0 Hz), 4.14 (q, 2H, 7.0 Hz), 4.05 (d, 1H, J=7.5 Hz), 4.02 (dd, 1H, J=8.0, 3.0 Hz), 3.82 (5, 3H, OMe), 3.64, (apparent t, 1H, J=10.0 Hz), 3.56 (apparent t, 1H, J=8.5 Hz), 3.30 (ddd, 1H, J=10.0, 10.0, 5.5 Hz), 2.62 (d, 1H, J=2.5 Hz), 2.07 (dd, 1H, J=5.5, 2.5 Hz), 1.78-1.75 (m, 1H), 1.27 (t, 3H, J=7.5 Hz) (FIG. 38) $^{13}$C NMR (500 MHz, $CDCl_3$): δ 171.5, 159.6, 138.3, 129.5, 118.6, 115.2, 111.4, 101.7, 80.9, 69.0, 68.6, 62.8, 61.0, 59.5, 55.3, 24.7, 21.6, 14.2 (FIG. 39). HRMS (m/z): [M+H]$^+$ calculated for $C_{18}H_{23}O_7$, 351.1438. found 351.1438.

Ethyl (2R,4aR,5aS,6aR,7R,7aS)-7-hydroxy-2-[4-(trifluoromethyl)phenyl]hexahydro-4H-cyclopropa[5,6]pyrano[3,2-d][1,3]dioxine-6-carboxylate (Compound 20f)

Figure 40:
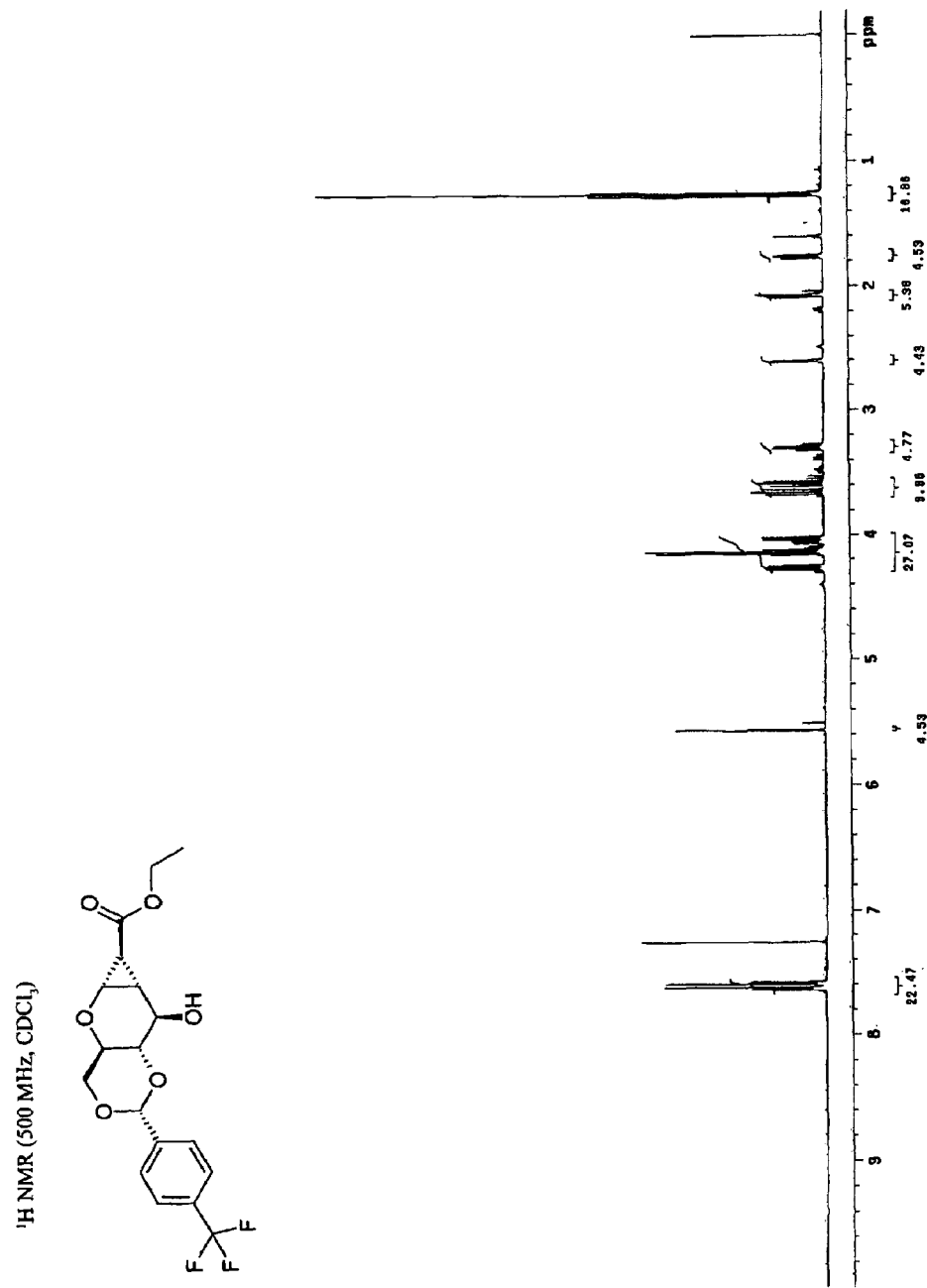
FIGS. 40 and 41 are NMR Spectra for Compound 20f.
Figure 41:
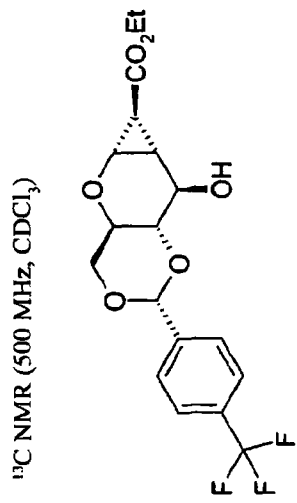
Figure 41:
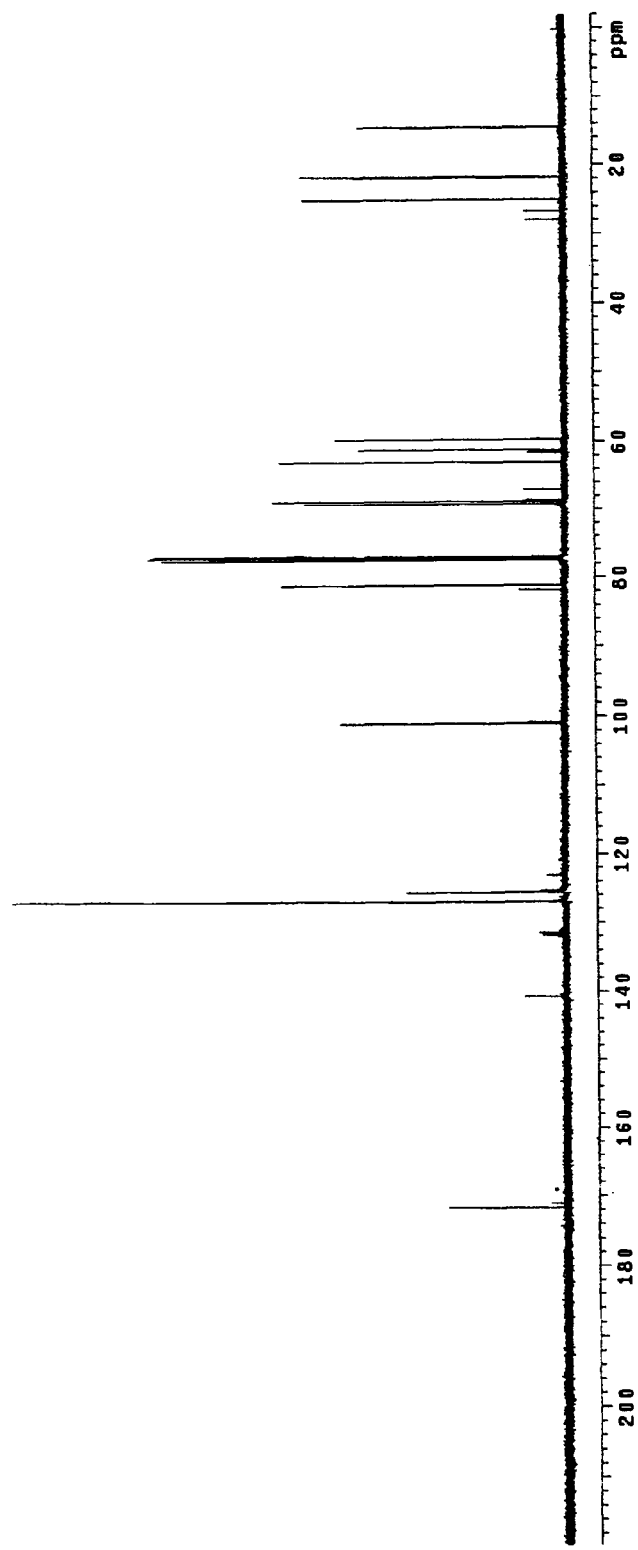

Treatment of Compound 6a (0.4 g, 1.7 mmol) with zinc chloride (1.2 g, 8.6 mmol) and 4(trifluoromethyl)benzaldehyde (3.0 g, 17.2 mmol) yielded a crude mixture. Column chromatography ($SiO_2$, a gradient of dichloromethane (1% TEA) to a 3:17 ratio of ethyl acetate in dichloromethane (1% TEA)) on the crude mixture afforded a white solid (0.42 g, 1.08 mmol) 63% yield: mp=128-131° C. $^1$H NMR (500 MHz, $CDCl_3$): δ 7.64 (d, 2H, J=8.0 Hz), 7.59 (d, 2H, J=8.5 Hz), 5.57 (5, 1H), 4.27 (dd, 1H, J=10.5, 5.5 Hz), 4.14 (q, 2H, J=7.0 Hz), 4.06 (dd, 1H, J=8.5, 2.0 Hz), 4.03 (dd, 1H, J=7.5, 3.0 Hz), 3.66 (dd, 1H, J=10.5, 10.0 Hz), 3.59 (dd, 1H, J=10.0, 9.0 Hz), 3.30 (ddd, 1H, J=10.0, 10.0, 5.5 Hz), 2.61 (d, 1H, J=2.5 Hz), 2.08 (dd, 1H, J=6.0, 2.5 Hz), 1.79-1.75 (m, 1H), 1.27 (t, 3H, J=7.0 Hz) (FIG. 41). $^{13}$C NMR (500 MHz, $CDCl_3$): δ 171.4, 140.5, 126.7 (4 C's), 125.3, 100.8, 81.0, 69.0, 68.6, 62.8, 61.0, 59.5, 24.8, 21.5, 14.2 (FIG. 40). HRMS (m/z): [M]$^+$ calculated for $C_{18}H_{19}F_3O_6$, 388.1134. found 388.1143 (Δ 0.9 mmu).

Example 12

Preparation of methyl (2R,4aR,5aS,6aR,7R,7aS)-7-hydroxy-2-(4-methoxyphenyl)hexahydro-4H-cyclopropa[5,6]pyrano[3,2-d][1 3]dioxine-6-carboxylate (Compound 19)

Figure 44:
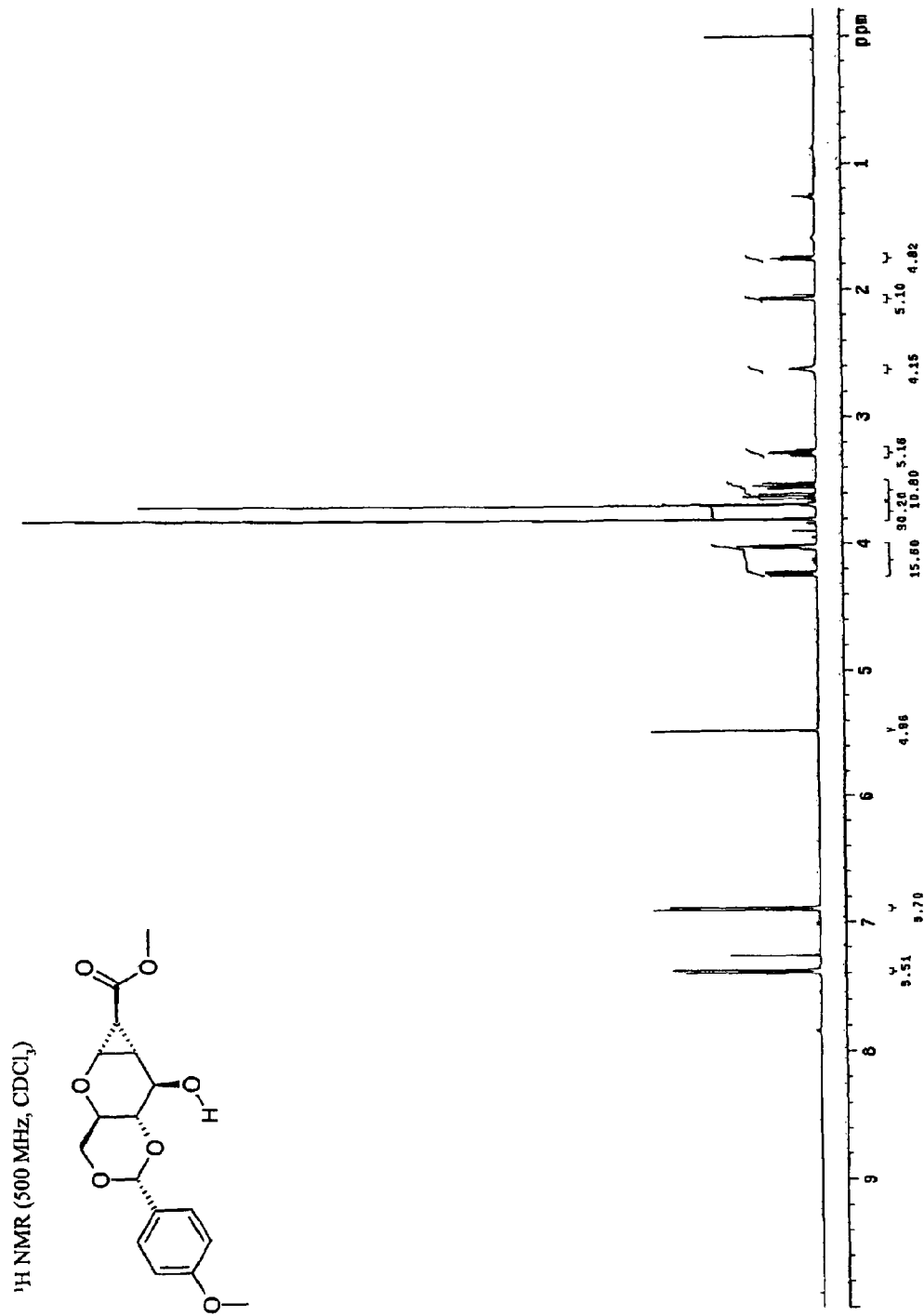
FIGS. 44 and 45 are NMR Spectra for Compound 19.
Figure 45:
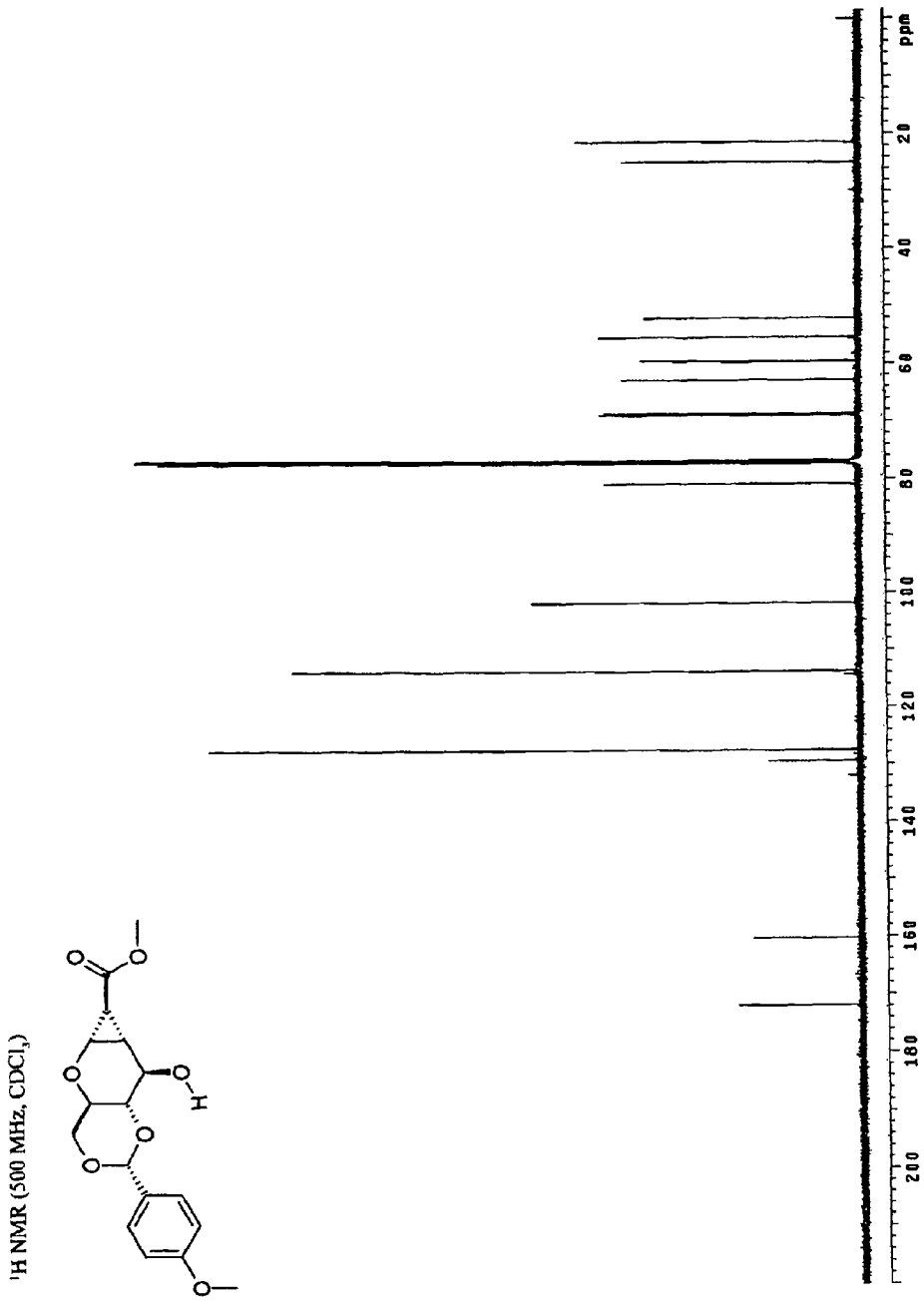

A solution of Compound 16 (0.73 g, 2.1 mmol) in 20 mL of 2M ammonia in methanol was stirred at room temperature for 7 days. The reaction mixture was concentrated in vacuo. Column chromatography (1:1 ratio of ethyl acetate in hexanes) on the crude mixture afforded a white solid (0.22 g, 0.65 mmol) 31% yield: mp=147-150° C. $^1$H NMR (500 MHz, $CDCl_3$): δ 7.41-7.39 (m, 2H), 6.92-6.89 (m, 2H), 5.50 (5, 1H), 4.25 (dd, 1H, J=10.5, 5.0 Hz), 4.07-4.03 (m, 2H), 3.82 (5, 3H), 3.71 (5, 3H), 3.64 (apparent t, 1H, J=10.0 Hz), 3.56 (dd, 1H, J=10.0, 8.5 Hz), 3.30 (ddd, 1H, J=10.0, 10.0, 5.5 Hz), 2.63 (5, broad, 1H), 2.09 (dd, 1H, J=5.5, 3.0 Hz), 1.79-1.76 (m, 1H) (FIG. 44). $^{13}$C NMR (500 MHz, $CDCl_3$) δ 171.9, 160.3, 129.4, 127.5 (2 C's), 113.8 (2 C's), 101.8, 80.8, 69.0, 68.6, 62.9, 59.5, 55.3, 52.0, 24.8, 21.4 (FIG. 45). HRMS (m/z): [M]$^+$ calculated for $C_{17}H_{20}O_7$, 336.1209. found 336.1213 (Δ 0.4 mmu).

Example 13

Screening for in vivo anticonvulsant activity in the MES, scMET, and minimal clonic seizure test in animal models (rat, mouse) were performed at the NINDS courtesy of James P. Stables, Dr. Tracy Chen, and Dr. Lauren Murphree. Toxicity was measured using the minimal motor impairment test described below.

Maximal Electroshock Seizure (MES) Test:

The MES test is a model for generalized tonic-clonic seizures. The seizures are highly reproducible and electrophysiologically consistent with human seizures. The test provides information about a compound's ability to prevent the spread of seizure when all neuronal circuits of the brain are maximally active. 60 Hz of alternating current (50 mA in mice, 150 mA in rats) is applied for 2 seconds via corneal electrodes that have been treated with an electrolyte solution containing an anesthetic (0.5% tetracaine HCl). Mice are tested at a variety of intervals after an i.p. injection of 0.01 mL/9 solution of the test compound (commonly in a 0.5% solution of methylcellulose) at 30, 100, and 300 mg/kg doses. Rats are examined after a 30 mg/kg (per os, p.o.) dose that is applied in a volume of 0.04 mL/g. An animal is considered "protected" from MES-induced seizures upon removal of the hind limb extensor component of the seizure.

Subcutaneous Metrazole Seizure Threshold Test (scMET):

The subcutaneous injection of metrazole, which is a convulsant, produces clonic seizures in laboratory animals. The scMET test is designed to identify compounds that raise the seizure threshold of an animal. Mice are pretreated with test compound at 30, 100, and 300 mg/kg doses in a similar manner to the MES test. Rats are treated with a 50 mg/kg dose (p.o.). At the previously determined TPE of the test compound, the dose of metrazole that will induce convulsions in 97% of animals ($CD_{97}$: 85 mg/kg mice) is injected into the loose fold of the skin in the midline of the neck. The animals are placed in isolation cages to minimize stress and observed for the next 30 minutes for the presence or absence of seizures. An episode of clonic spasms (approximately 3-5 seconds) of the fore and/or hindlimbs, jaws or vibrissae is taken as the endpoint. Animals which do not meet this criterion are considered protected.

Minimal Clonic Seizure (6 Hz) Test:

Sometimes clinically useful anticonvulsants are ineffective in the standard MES and scMET tests but still exhibit in vivo efficacy. The minimal clonic seizure (6 Hz) test, like the MES test, is used to assess a compound's ability to protect against electrically-induced seizures. The minimal clonic (6 Hz) seizure test uses a lower frequency (6 Hz) and a longer duration of stimulation (3 seconds) than the MES test. Test compounds are pre-administered to mice via i.p. injection. At varying times, individual mice (four per time point) are challenged with sufficient current via corneal electrodes to elicit a psychomotor seizure in 97% of animals (32 mA for 3 second). Untreated mice will display seizure characterized by a minimal clonic phase followed by stereotyped, automatistic behaviors described originally as being similar to the aura of human patients with partial seizures. Animals not displaying this behavior are considered to be protected.

Acute Toxicity—Minimal Motor Impairment:

Animals are monitored for overt signs of impaired neurological or muscular function to assess a compound's toxicity. In mice, the rotorod procedure is used to disclose minimal muscular or neurological impairment. When a mouse is placed on a rotating rod (6 rpm), the animal can maintain its equilibrium for long periods of time. The animal is considered toxic if it falls off the rotating rod three times during a 1 minute period. In rats, minimal motor deficit is indicated by ataxia, which is manifested by an abnormal, uncoordinated gait. Rats used for toxicity evaluation are examined before the test drug is given as individual animals may have peculiarities in gait, equilibrium, and pacing response which must be distinguished from potential effects of the test substance. Animals may also exhibit a circular or zigzag gait, abnormal body posture and spreading of legs, tremors, hyperactivity, lack of exploratory behavior, somnolence, stupor, catalepsy, and/or loss of placing response and changes in muscle tone.

Animals:

Male and female albino CF1 mice (18-25 g, Charles River, Portage, Mich.) and male albino Sprague-Dawley rats (275-300 g, kindling test; 100-150 g all other tests; Charles River, Raleigh, N.C.) were used as experimental animals.

The results for Mice and Rat MES, Minimal Clonic Seizure (6 Hz), and Toxicity Data MES Test are reported in Table 2 for various compounds of the invention.

TABLE 2

| | 14b | 4 | 5 | 6a | 15 | 7 | 8a | 8b | 10 | 9 |
|---|---|---|---|---|---|---|---|---|---|---|
| MES 30 0.5 h | 0/1 | 0/1 | 0/1 | 0/1 | | 0/1 | 0/1 | 0/1 | 0/1 | 0/1 |
| MES 100 0.5 h | 0/3 | 0/3 | 0/3 | 0/3 | | 0/3 | 0/3 | 0/3 | 0/3 | 0/3 |
| MES 300 0.5 h | 0/1 | 0/1 | 0/1 | 0/1 | | 0/1 | 0/1 | 0/1 | 0/1 | 0/1 |
| MES 30 4 h | 0/1 | 0/1 | 0/1 | 0/1 | | 0/1 | 0/1 | 0/1 | 0/1 | 0/1 |
| MES 100 4 h | 0/3 | 0/3 | 0/3 | 0/3 | | 0/3 | 0/3 | 0/3 | 0/3 | 0/3 |
| MES 300 4 h | 0/1 | 0/1 | 0/1 | 0/1 | | 0/1 | 0/1 | 0/1 | 0/1 | 0/1 |
| scMET 30 0.5 h | 0/1 | 0/1 | 0/1 | 0/1 | | 0/1 | 0/1 | 0/1 | 0/1 | 0/1 |
| scMET 100 0.5 h | 0/1 | 0/1 | 0/1 | 0/1 | | 0/1 | 0/1 | 0/1 | 0/1 | 0/1 |
| scMET 300 0.5 h | 0/1 | 0/1 | 0/1 | 0/1 | | 0/1 | 0/1 | 0/1 | 0/1 | 0/1 |
| scMET 30 0.4 h | 0/1 | 0/1 | 0/1 | 0/1 | | 0/1 | 0/1 | 0/1 | 0/1 | 0/1 |
| scMET 100 0.4 h | 0/1 | 0/1 | 0/1 | 0/1 | | 0/1 | 0/1 | 0/1 | 0/1 | 0/1 |
| scMET 300 0.4 h | 0/1 | 0/1 | 0/1 | 0/1 | | 0/1 | 0/1 | 0/1 | 0/1 | 0/1 |
| TOX 30 0.5 h | 0/4 | 0/4 | 0/4 | 0/4 | | 0/4 | 0/4 | 0/4 | 0/4 | 0/4 |
| TOX 100 0.5 h | 2/8 | 0/8 | 0/8 | 0/8 | | 1/8 | 0/8 | 1/8 | 0/8 | 0/8 |
| TOX 300 0.5 h | 4/4 | 0/4 | 1/4 | 0/4 | | 3/4 | 1/4 | 1/4 | 0/4 | 0/4 |
| TOX 30 4 h | 0/2 | 0/2 | 0/2 | 0/2 | | 0/2 | 0/2 | 0/2 | 0/2 | 0/2 |
| TOX 100 4 h | 0/4 | 1/4 | 0/4 | 0/4 | | 0/4 | 0/4 | 0/4 | 0/4 | 0/4 |
| TOX 300 4 h | 0/2 | 0/2 | 0/2 | 0/2 | | 1/2 | 0/2 | 0/2 | 0/2 | 0/2 |
| 6 Hz 100 0.25 h | — | — | — | — | | — | — | — | — | — |
| 6 Hz 100 0.5 h | — | — | — | — | | — | — | — | — | — |
| 6 Hz 100 2 h | — | — | — | — | | — | — | — | — | — |

| | 16 | 16 (rat) | 17a | 17b | 20a | 20b | 20c | 20d | 20e | 18 |
|---|---|---|---|---|---|---|---|---|---|---|
| MES 30 0.5 h | 0/1 | 0/4 | 0/1 | 0/1 | 0/1 | 1/5 | 0/1 | 0/1 | 0/1 | 0/1 |
| MES 100 0.5 h | 0/3 | — | 0/3 | 0/3 | 0/3 | 0/7 | 0/3 | 0/3 | 0/3 | 0/3 |
| MES 300 0.5 h | 0/1 | — | 0/1 | 0/1 | 0/1 | 0/1 | 0/1 | 0/1 | 0/1 | 0/1 |
| MES 30 4 h | 0/1 | 1/4 | 0/1 | 0/1 | 0/1 | 0/1 | 0/1 | 0/1 | 0/1 | 0/1 |
| MES 100 4 h | 0/3 | — | 0/3 | 0/3 | 0/3 | 0/3 | 0/3 | 0/3 | 0/3 | 0/3 |
| MES 300 | 0/1 | — | 0/1 | 0/1 | 0/1 | 0/1 | 0/1 | 0/1 | 0/1 | 0/1 |

TABLE 2-continued

| | | | | | | | | | | |
|---|---|---|---|---|---|---|---|---|---|---|
| 4 h | | | | | | | | | | |
| scMET 30 0.5 h | 0/1 | — | 0/1 | 0/1 | 0/1 | 0/1 | 0/1 | 0/1 | 0/1 | 0/1 |
| scMET 100 0.5 h | 0/1 | — | 0/1 | 0/1 | 0/1 | 0/1 | 0/1 | 0/1 | 0/1 | 0/1 |
| scMET 300 0.5 h | 0/1 | — | 0/1 | 0/1 | 0/1 | 0/1 | 0/1 | 0/1 | 0/1 | 0/1 |
| scMET 30 0.4 h | 0/1 | — | 0/1 | 0/1 | 0/1 | 0/1 | 0/1 | 0/1 | 0/1 | 0/1 |
| scMET 100 0.4 h | 0/1 | — | 0/1 | 0/1 | 0/1 | 0/1 | 0/1 | 0/1 | 0/1 | 0/1 |
| scMET 300 0.4 h | 0/1 | 0/4 | 0/1 | 0/1 | 0/1 | 0/1 | 0/1 | 0/1 | 0/1 | 0/1 |
| TOX 30 0.5 h | 0/4 | — | 0/4 | 0/4 | 0/4 | 1/4 | 0/4 | 1/4 | 0/4 | 0/4 |
| TOX 100 0.5 h | 2/8 | — | 0/8 | 0/8 | 0/8 | 0/8 | 0/8 | 1/8 | 0/8 | 0/8 |
| TOX 300 0.5 h | 3/4 | — | 0/4 | 2/4 | 0/4 | 0/4 | 0/4 | 2/4 | 0/4 | 0/4 |
| TOX 30 4 h | 0/2 | 0/4 | 0/2 | 0/2 | 0/2 | 0/2 | 0/2 | 0/2 | 0/2 | 0/2 |
| TOX 100 4 h | 0/4 | — | 0/4 | 0/4 | 0/4 | 0/4 | 0/4 | 0/4 | 0/4 | 0/4 |
| TOX 300 4 h | 1/2 | — | 0/2 | 0/2 | 0/2 | 0/2 | 0/2 | 1/2 | 0/2 | 0/2 |
| 6 Hz 100 0.25 h | — | — | — | 0/4 | — | — | — | 1/4 | — | — |
| 6 Hz 100 0.5 h | — | — | — | 1/4 | — | — | — | 0/4 | — | — |
| 6 Hz 100 2 h | — | — | — | 1/4 | — | — | — | 0/4 | — | — |

Benzylidene analogs at C4 and C6 (Compounds 16 and 17b) yielded anticonvulsant activity. To date, these are the first carboethoxy cyclopropanated glucopyranoses that have exhibited anticonvulsant prophylaxis. The p-isopropyl substituted Compound 20b showed activity, but the activity was accompanied by minimal motor impairment at the same time point. Thus, it was impossible to determine if the observed protection was true convulsant prophylaxis. The same held true for 2,4-difluoro analog Compound 20d, which exhibited activity, but which also exhibited minimal motor impairment at the same dose.

Example 14

Receptor binding profiles were provided by the National Institute of Mental Health's Psychoactive Drug Screening Program, Contract # N01 MH32004 (NIMH PDSP) The NIMH PDSP is directed by Bryan L. Roth M. D., Ph.D. at the University of North Carolina at Chapel Hill and Project Officer Jamie Driscol at NIMH, Bethesda Md., USA. Protocols for receptor-based assays by the PDSP may be found on the website: http://pdsp.med.unc.edu/pdspw/binding.php and http://pdsp.med.unc.edu/pdspw/function.php (Apr. 30, 2008).

FIG. 48 is a table showing the results of the PDSP screening for various compounds. Certain compounds exhibited greater than 50% inhibition of radioligand binding at the 5-HT5A, alpha2C, $Ca^{2+}$, D1, D4, D5, DAT, and NMDA (PCP site) receptors/channels. These suggest interesting receptor activity for the inventive compounds.

Radioligand competition binding assays were performed as previously described (Rothman, R. B., Baumann, M. H., Savage, J. E., Rauser, L., McBride, Hufeisen, S. J., Roth B. L. Circulation (2000) 102:2836-2841) for Compounds 7 and 16. Briefly, test compounds were dissolved to 10 mM in 100% DMSO, then diluted to the desired concentrations (spanning seven orders of magnitude) in Dopamine Binding Buffer (50 mM NaCl, 50 mM HEPES, 5 mM $MgCl_2$, 0.5 mM EDTA, pH 7.4). Diluted test and reference compounds were added to wells containing radioligand ([$^3$H]SCH23390, 0.3 nM final concentration) and buffer, then membrane fractions from cells stably expressing cloned, human D1 or D5 receptors were added and binding was allowed to equilibrate at room temperature for 1.5 hours. At equilibrium, reactions were filtered (using a FilterMate 96-well harvester, PerkinElmer) onto GF-A glass fiber filters (Wallac) and allowed to dry. Meltilex scintillant (Wallac) was melted onto the dry filters, and then allowed to cool. Filters were then sealed in plastic bags and counted on a Wallac TriLux microbeta counter.

Raw data (dpm) representing total radioligand binding (i.e., specific+non-specific binding) were plotted as a function of the logarithm of the molar concentration of the competitor (i.e., test or reference compound). Non-linear regression of the normalized (i.e., percent radioligand binding compared to that observed in the absence of test or reference compound) raw data is performed in Prism 4.0 (GraphPad Software) using the built-in three parameter logistic model describing ligand competition binding to radioligand-labeled sites:

$$y = \text{bottom} + [(\text{top} - \text{bottom})/(1 + 10^{x - \log IC_{50}})]$$

where bottom equals the residual radioligand binding measured in the presence of 10 μM reference compound (i.e., non-specific binding) and top equals the total radioligand binding observed in the absence of competitor. The log $IC_{50}$ (i.e., the log of the ligand concentration that reduces radioligand binding by 50%) is thus estimated from the data and used to obtain the $K_i$ by applying the Cheng-Prusoff approximation:

$$K_i = IC_{50}/(1 + [\text{ligand}]/K_D)$$

where [ligand] equals the assay radioligand concentration and $K_D$ equals the affinity constant of the radioligand for the target receptor.

Compounds 7 and 16 demonstrated significant inhibition of the D1 dopamine receptor. Compound 7 had a $K_i$ of 6.227 μM and Compound 16 had a $K_i$ of 4.74 μM.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A compound of formula I or formula II:

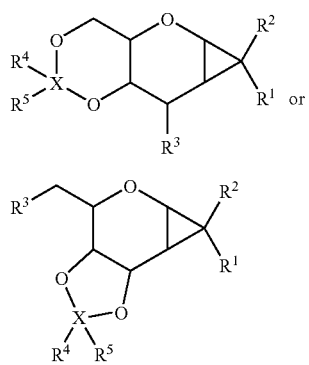

wherein $R^1$ represents hydrogen or a halogen;
$R^2$ represents a halogen, an ester group or a —$CH_2R^6$ group and $R^6$ represents —OH, a halogen, a —$SR^7$ group, an amino group, or a —$NR^8R^9$ group and $R^7$, $R^8$, and $R^9$ each independently represent hydrogen, an alkyl group, an aryl group, or a heteroaryl group, provided that when $R^1$ represents hydrogen, $R^2$ is an ester group or a —$CH_2R^6$ group, and when $R^1$ represents a halogen, $R^2$ is a halogen;
$R^3$ represents —OH, a methyl ether, an oxime, or a sulfonamide; and
X represents a silicon or carbon, provided that when X represents a silicon, $R^4$ and $R^5$ each independently represent a substituted or unsubstituted, branched or unbranched, $C_1$-$C_4$ alkyl group, and when X represents a carbon, i) $R^4$ and $R^5$ are each independently a substituted or unsubstituted, branched or unbranched, $C_1$-$C_4$ alkyl group, or ii) $R^4$ represents H and $R^5$ represents a substituted or unsubstituted phenyl group.

2. A compound according to claim 1, wherein $R^1$ represents hydrogen and $R^2$ represents a methyl ester group or an ethyl ester group.

3. A compound according to claim 1, wherein $R^1$ and $R^2$ are the same and represent either chlorine or bromine.

4. A compound according to claim 1, wherein X represents silicon and $R^4$ and $R^5$ each represent a tert-butyl group.

5. A compound according to claim 1, wherein X represents a carbon and $R^4$ and $R^5$ each represent a methyl group.

6. A compound according to claim 1, wherein X represents a carbon, $R^4$ represents hydrogen, and $R^5$ represents an unsubstituted phenyl group or a phenyl group substituted with at least one substituent selected from the group consisting of a methoxy group, a tert-butyl group, a trifluoromethyl group, an isopropyl group, a halogen, —OH, —$SCH_3$, and —$N(CH_3)_2$.

7. A compound according to claim 6, wherein $R^5$ is selected from the group consisting of an unsubstituted phenyl group, a p-methoxyphenyl group, a p-tert-butylphenyl group, a m-methoxyphenyl group, a trifluoromethylphenyl group, a p-isopropylphenyl group, and a difluorophenyl group.

8. A compound according to claim 1, wherein $R^3$ represents —OH, an oxime group, a methyl ether group, or a sulfonamide group which is a N,N'-dimethylsulfonamide group.

9. A compound according to claim 1 selected from the group consisting of:

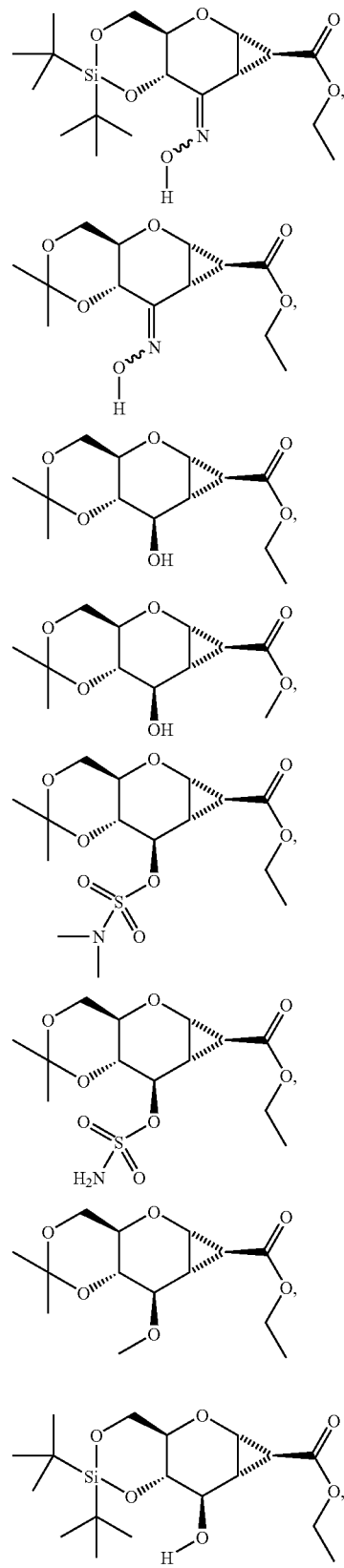

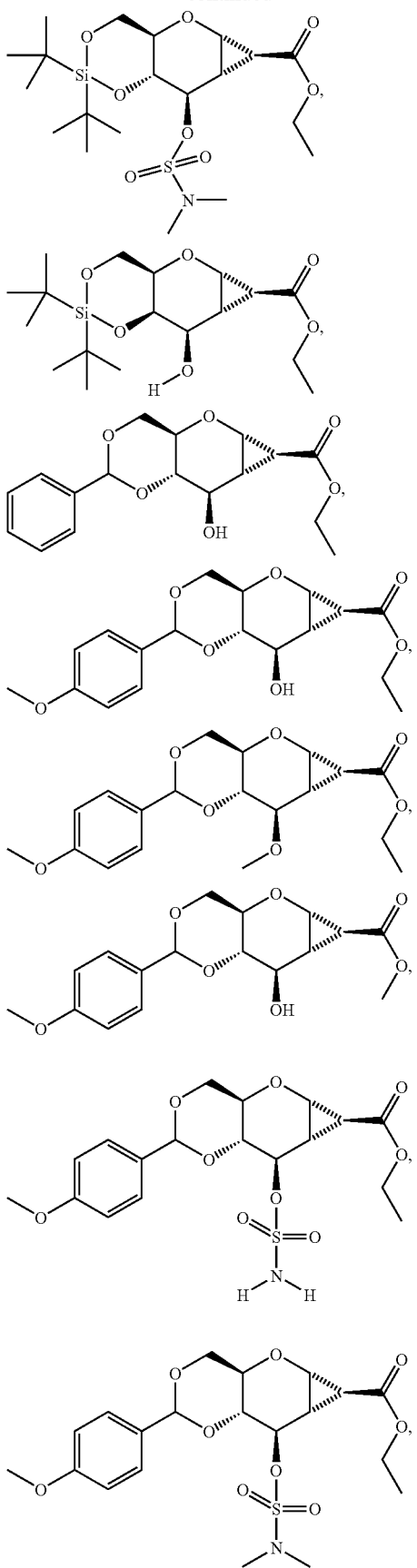
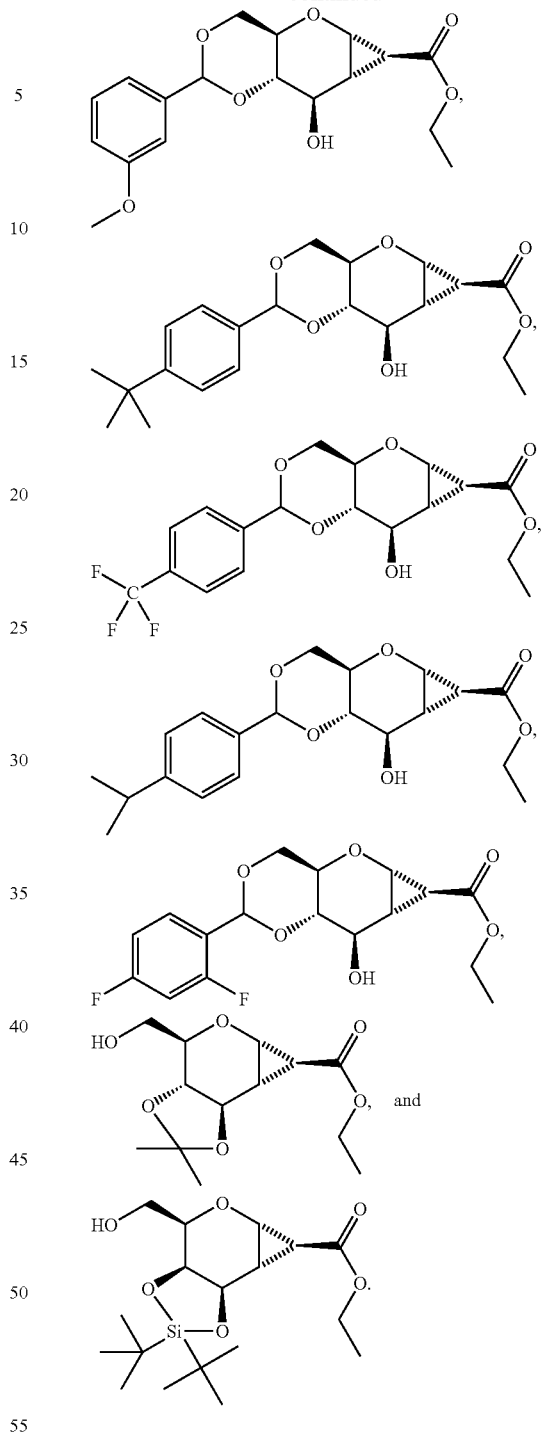

10. A method of treating seizures in an organism comprising administering an effective amount of a compound according to claim 1 to an organism in need thereof.

11. A method according to claim 10, wherein about 0.1 to about 500 milligrams per kilogram body weight per day of the compound is administered.

12. A pharmaceutical composition comprising an effective amount of a compound according to claim 1 and a pharmaceutically acceptable excipient.

13. A pharmaceutical composition according to claim 12, wherein the amount of the compound present in the composition is from about 0.1 to about 500 mg.

14. A pharmaceutical composition comprising an effective amount of a compound according to claim 9 and a pharmaceutically acceptable excipient.

15. A pharmaceutical composition according to claim 14, wherein the amount of the compound present in the composition is from about 0.1 to about 500 mg.

16. The compound of claim 1, which is

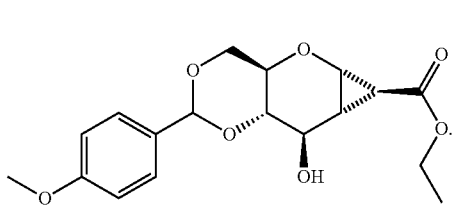

17. The compound of claim 1, which is

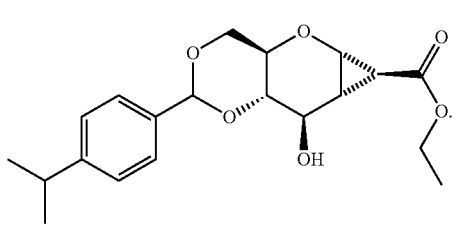

18. The compound of claim 1, which is

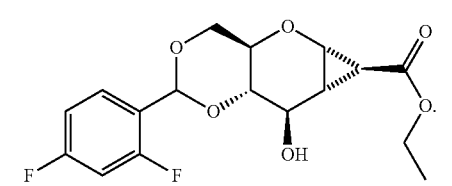

19. The pharmaceutical composition of claim 12, wherein the compound is

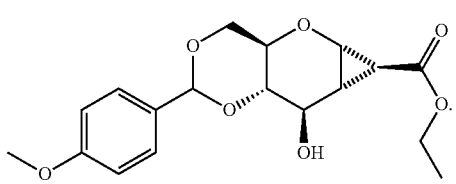

20. The pharmaceutical composition of claim 12, wherein the compound is

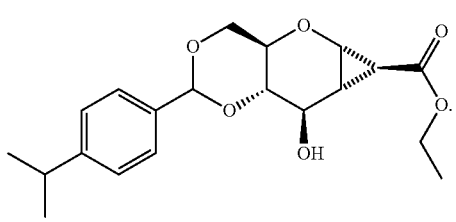

21. The pharmaceutical composition of claim 12, wherein the compound is

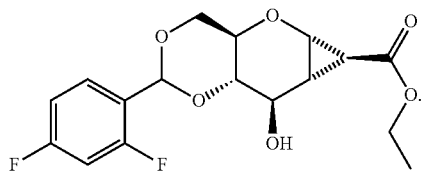

22. The method of claim 10, wherein the compound is

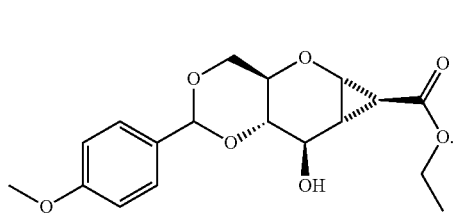

23. The method of claim 12, wherein the compound is

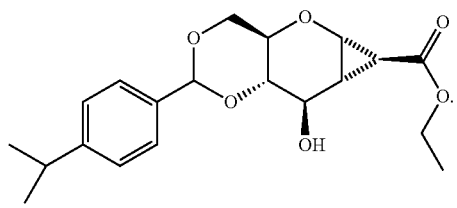

24. The method of claim 12, wherein the compound is

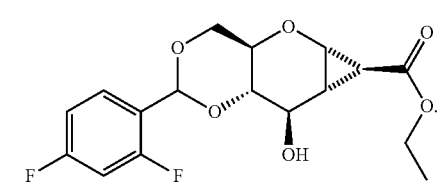

25. The method of claim 12, wherein the organism is a human.

26. The method of claim 12, wherein the compound is administered parenterally.

* * * * *